US006077833A

United States Patent [19]
Bennett et al.

[11] Patent Number: 6,077,833
[45] Date of Patent: Jun. 20, 2000

[54] OLIGONUCLEOTIDE COMPOSITIONS AND METHODS FOR THE MODULATION OF THE EXPRESSION OF B7 PROTEIN

[75] Inventors: C. Frank Bennett, Carlsbad; Timothy A. Vickers, Oceanside, both of Calif.

[73] Assignee: Isis Pharmaceuticals, Inc., Carlsbad, Calif.

[21] Appl. No.: 08/777,266

[22] Filed: Dec. 31, 1996

[51] Int. Cl.$^7$ .............................. A61K 31/70; C07H 2/00; C12N 5/06
[52] U.S. Cl. ............................ 514/44; 435/375; 536/24.5
[58] Field of Search ...................... 435/6, 172.1, 172.3, 435/375, 325; 514/44, 23.1; 536/24.3, 24.31, 24.5; 935/34

[56] References Cited

U.S. PATENT DOCUMENTS

| | | | |
|---|---|---|---|
| 4,689,320 | 8/1987 | Kaji | 514/44 |
| 4,806,463 | 2/1989 | Goodchild et al. | 435/5 |
| 5,004,810 | 4/1991 | Draper | 536/24.5 |
| 5,034,506 | 7/1991 | Summerton et al. | 528/391 |
| 5,087,617 | 2/1992 | Smith | 514/44 |
| 5,098,890 | 3/1992 | Gewirtz et al. | 514/44 |
| 5,135,917 | 8/1992 | Burch | 514/44 |
| 5,138,045 | 8/1992 | Cook et al. | 536/24.5 |
| 5,166,195 | 11/1992 | Ecker | 514/44 |
| 5,194,428 | 3/1993 | Agrawal et al. | 514/44 |
| 5,218,105 | 6/1993 | Cook et al. | 536/25.31 |
| 5,242,906 | 9/1993 | Pagano et al. | 514/44 |
| 5,264,423 | 11/1993 | Cohen et al. | 514/44 |
| 5,276,019 | 1/1994 | Cohen et al. | 514/44 |
| 5,286,717 | 2/1994 | Cohen et al. | 514/44 |
| 5,434,131 | 7/1995 | Linsley et al. | 514/2 |
| 5,459,255 | 10/1995 | Cook et al. | 536/27.13 |
| 5,512,438 | 4/1996 | Ecker | 435/6 |
| 5,514,788 | 5/1996 | Bennett et al. | 536/23.1 |
| 5,539,082 | 7/1996 | Nielsen et al. | 530/300 |
| 5,585,479 | 12/1996 | Hoke et al. | 536/24.5 |
| 5,667,998 | 9/1997 | Dougherty et al. | 435/172.3 |

FOREIGN PATENT DOCUMENTS

| | | |
|---|---|---|
| 0 600 591 A2 | 10/1993 | European Pat. Off. . |
| 0 643 077 A1 | 9/1994 | European Pat. Off. . |
| 92/20823 | 11/1992 | WIPO . |
| 95/03408 | 2/1995 | WIPO . |
| 95/05464 | 2/1995 | WIPO . |
| 95/06738 | 3/1995 | WIPO . |
| 95/22619 | 8/1995 | WIPO . |
| 95/32734 | 12/1995 | WIPO . |
| 95/34320 | 12/1995 | WIPO . |
| 96/11279 | 4/1996 | WIPO . |

OTHER PUBLICATIONS

Antisense '97: A roundtable;e on the industry. Nature Biotechnol. 15: 519–524, Jun. 1997.
Gewirtz et al. Facilitating oligonucleotide delivery: Helping antisense deliver on its promise. Proc. Natl. Acad. Sci. USA 93: 3161–3163, Apr. 1996.
Gura. Antisense has Growing Pains. Science 270: 575–577, Oct. 1995.
Rojanasakul. Antisense therapeutics: drug delivery and targeting. Adv. Drug Delivery Rev. 18: 115–131, 1996.
Stull et al. Antigene, ribozyme and aptamer nucleic acid drugs: Progress and prospects. Pharm. Res. 12: 465–483, 1995.
Christoffersen et al. Ribozymes as human therapeutic agents. J. Med. Chem. 38(12): 2023–2037, Jun. 1995.
Uhlmann et al. Antisense oligonucleotides: A new therapeutic principle. 90(4): 543–584, Jun. 1990.
Alberts et al., "*Molecular Biology of the Cell*", 1983, Garland Publishing Inc., New York, pp. 411–415.
Allison et al., "The Yin and Yang of T Cell Costimulation", *Science*, 1995, 270, 932–933.
Allison, J.P, "CD28–B7 interactions in T–cell activation", *Curr. Opin. Immunol.*, 1994, 6, 414.
Azuma et al., "B70 antigen is a second ligand for CTLA–4 and CD28", *Nature*, 1993, 366, 76–79.
Berkow et al., eds., "*The Merck Manual of Diagnosis and Therapy*", 15th Ed., 1987, Rahway, N.J., pp. 302–336 and 2516–2522.
Borriello et al., "Characterization of the Murine B7–1 Genomic Locus Reveals an Additional Exon Encoding an Alternative Cytoplasmic Domain and a Chromosomal Location of Chromosome 16, Band 15", *J. Immunol.*, 1994, 153.
Borriello et al., "Differential Expression of Alternate mB7–2 Transcripts", *J. Immunol.*, 1995, 155, 5490–5497.
Brigstock et al., "Species–Specific High Molecular Weight Forms of Basic Fibroblast Growth Factors", *Growth Factors*, 1990, 4, 45–52.
Charachon et al., "Phosphorothioate Analogues of $(2'-5')(A)_4$: Agonist and Antagonist Activities in Intact Cells", *Biochemistry*, 1990, 29, 2550–2555.
Chen et al., "Monoclonal Antibody 2D10 Recognizes a Novel T Cell Costimulatory Molecule on Activated Murine B Lymphocytes", *J. Immunol.*, 1994, 152, 2105–2114.
Chen et al., "Molecular Cloning and Expression of Early T Cell Costimulatory Molecule–1 and its Characterization as B7–2 Molecule", *J. Immunol.*, 1994, 152, 4929–4936.
Crooke et al., eds., "Antisense Research and Applications", CRC Press, Boca Raton, 1993, pp. 171–172.
Crooke et al., "Pharmokinetic Properties of Several Novel Oligonucleotide Analogs in mice", *J. Pharmacol. Exp. Ther.*, 1996, 277, 923–937.
DeVirgilio et al., "Cloning and Disruption of a Gene Required for Growth on Acetate but not on Ethanol: the Acetyl–Coenzyme A Synthetase Gene of *Saccharomyces cerevisiae*", *Yeast*, 1992, 8, 1043–1051.

(List continued on next page.)

Primary Examiner—George C. Elliott
Assistant Examiner—Thomas G. Larson
Attorney, Agent, or Firm—Law Offices of Jane Massey Licata

[57] ABSTRACT

Compositions and methods for the diagnosis, prevention and treatment of immune states and disorders amenable to treatment through modulation of T cell activation are provided. In accordance with preferred embodiments, oligonucleotides are provided which are specifically hybridizable with nucleic acids encoding B7 proteins.

46 Claims, 9 Drawing Sheets

OTHER PUBLICATIONS

Dulbecco et al., "Plaque Production by the Polyoma Virus", *Virol.*, 1959, 8, 396–397.

Freeman et al., "Cloning of B7–2: A CTLA–4 Counter–Receptor That Costimulates Human T Cell Proliferation", *Science*, 1993, 262, 909–911.

Freeman et al., "B7, A New Member of the Ig Superfamily with Unique Expression on Activated and Neoplastic B Cells", *J. Immunol.*, 1989, 143, 2714–2722.

Freeman et al., "Structure, Expression, and T Cell Costimulatory Activity of the Murine Homologue of the Human B Lymphocyte Activation Antigen B7", *J. Exp. Med.*, 1991, 174, 625–631.

French et al., "Express of Two Related Nonstructural Proteins of Bluetongue Virust (BTV) Type 10 in Insect Cells by a Recombinant Baculovirus: Production of Polyclonal Ascitic Fluid and Characterization of the Gene Product in BTV–Infected BHK Cells", *J. Virol.*, 1989, 63, 3270–3278.

Gebeyehu, G., et al., "Novel biotinylated nucleotide—analogs for labeling and colorimetric detection of DNA", *Nucleic Acids Res.*, 1987, 15, 4513–4534.

Gelbert et al., "Analysis of GPT Activity in Mammalian Cells with a Chromosomally Integrated Shuttle Vector Containing Altered gpt Genes", *Somat. Cell. Mol. Genet.*, 1990, 16, 173–184.

Gold and Stormo, in: *Escherichia coli and Salmonella typhimurium: Cellular and Molecular Biology*, vol. 2, 1987.

Hakim et al., "Acute Graft–Versus–Host Reaction Can be Aborted by Blockade of Costimulatory Molecules", *J. Immun.*, 1995, 155, 1760–1766.

Harlan et al., "Mice expressing both B7–1 and viral glycoprotein on pancreatic beta cells along with glycoprotein-specific transgenic T cells develop diabetes due to a breakdown T–lymphocyte unresponsiveness", *Proc. Natl. Acad. Sci. U.S.A.*, 1994, 91, 3137–3141.

Hathcock et al., "Identification of an Alternative CTLA–4 Ligand Costimulatory for T Cell Activation", *Science*, 1993, 262, 905–907.

Inobe et al., "The Role of the B7–1a Molecule, an Alternatively Spliced Form of Murine B7–1 (CD80), on T Cell Activation", *J. Immun.*, 1996, 157, 582–588.

Jellis et al., "Genomic Organization of the gene coding for the costimulatory human B–lymphocyte antigen B7–2 (CD86)", *Immunogenet.*, 1995, 42, 85.

June et al., "The B7 and CD28 receptor families", *Immunol. Today*, 1994, 15, 321–331.

Kabanov et al., "A new class of antivirals: antisense oligonucleotides combined with a hydrophobic substituent effectively inhibit influenza virus reproduction and synthesis of virus–specific proteins in MDCK cells", *FEBS Lett.*, 1990, 259.

Kanagasundaram et al., "Isolation and characterization of the gene encoding gluconolactonase from *Zymomonas mobilis*", *Biochim. Biophys. Acta*, 1992, 1171, 198–200.

Kornberg, A., DNA Replication, 1974, W.H. Freeman & Co., San Francisco, 1974, pp. 75–77.

Lenschow et al., "Long–Term Survival of Xenogeneic Pancreatic Islet Grafts Induced by CTLA4Ig", 1992, *Science*, 257, 789–792.

Lenschow et al., *Curr. Opin. Immunol.*, 1993, 5(5), 747–52.

Lenschow et al., "Expression and functional significance of an additional ligand for CTLA–4", *Proc. Natl. Acad. Sci. U.S.A.*, 1993, 90, 11054–11058.

Letsinger et al., "Cholesteryl–conjugated oligonucleotides: Synthesis, properties, and activity as inhibitors or replication of human immunodeficiency virus in cell culture", *Proc. Natl. Acad. Sci. USA*, 1989, 86, 6553–6556.

Levine et al., "Antiviral Effect and Ex Vivo $CD4^+$ T Cell Proliferation in HIV–Positive Patients as a Result of CD28 Costimulation", *Science*, 1996, 272, 1939–1942.

Lin et al., "Long–Term Acceptance of Major Histocompatibility Complex Mismatched Cardiac Allografts Induced by CTLA4Ig Plus Donor–specific Transfusion", *J. Exp. Med.*, 1993, 178, 1801–1806.

Linsley et al., "CTLA–4 Is a Second Receptor for the B Cell Activation Antigen B7", *J. Exp. Med.*, 1991, 174, 561–569.

Linsley et al., "Immunosuppression in Vivo by a Soluble Form of the CTLA–4 T Cell Activation Molecule", *Science*, 1992, 257, 792–795.

Linsley and Ledbetter, "The Role of the CD28 Receptor During T Cell Responses to Antigen", *Annu. Rev. Immunol.*, 1993, 11, 191–212.

Liu and Linsley, "Costimulation of T–cell growth", *Curr. Opin. Immunol.*, 1992, 4, 265–270.

Manoharan et al., "Cholic Acid–Oligonucleotide Conjugates for Antisense Applications", *Bioorg. Med. Chem. Let.*, 1994, 4, 1053–1060.

Manoharan et al., "Oligonucleotide Conjugates: Alteration of the Pharmacokinetic Properties of Antisense Agents", *Nucleosides & Nucleotides*, 1995, 14, 969.

Manoharan et al., "Chemical Modifications to Improve Uptake and Bioavailability of Antisense Oligonucleotides", *Ann. N.Y. Acad. Sci.*, 1992, 660, 306–309.

Manoharan et al., "Lipidic Nucleic Acids", *Tetrahedron Lett.*, 1995, 36, 3651–3654.

Manoharan et al., Introduction of a Lipophilic Thioether Tether in the Minor Groove of Nucleic Acids for Antisense Applications:, *Bioorg. Med. Chem. Let.*, 1993, 3, 2765–2770.

Markussen et al., "Translation control of oskar generates Short OSK, the isoform that induces pole plasm assembly", *Development*, 1995, 121, 3723–3732.

Martin et al., "Ein neuer Zugang zu 2'–O–Alkyribonucleosiden und Eigenschaften deren Oligonucleotide", *Helv. Chim. Acta*, 1995, 78, 486–504.

McDermott et al., "Structure and lens expression of the gene encoding chicken βA3/A1–crystallin", *Gene*, 1992, 117, 193.

Mishra et al., "Improved leishmanicidal effect of phosphorotioate antisense oligonucleotides by LDL–mediated delivery", *Biochim. Biophys. Acta*, 1995, 1264, 229–237.

Monaco et al., "Structure of Two Rat Genes Coding for Closely Related Rolipram–sensitive cAMP Phosphodiesterases", *J. Biol. Chem.*, 1994, 269, 347–357.

Moore et al., "Cell Line Derived from Patient with Myeloma", *N.Y. J. Med.*, 1968, 68, 2054–2060.

Nabavi et al., "Signalling through the MHC class II cytoplasmic domain is required for antigen presentation and induces B7 expression", *Nature*, 1992, 360, 266–268.

Gao et al., "Cloning and Characterization of a Mouse Gene with Homology to the Human von Hippel–Lindau Disease Tumor Suppressor Gene: Implications for the Potential Organization of the Human von Hippel–Lindau Disease Gene", *Cancer Res.*, 1995, 55, 743–747.

Nielsen et al., "Sequence–Selective Recognition of DNA by Strand Displacement with a Thymine–Substituted Polyamide", *Science*, 1991, 254, 1497–1500.

Oberhauser et al., "Effective incorporation of 2'-O-methyl-oligoribonucleotides into liposomes and enhanced cell association through modification with thiocholesterol", *Nucl. Acids Res.*, 1992, 20, 533–538.

Olsen et al., "Inhibition of Protein Kinase–A by Overexpression of the Cloned Human Protein Kinase Inhibitor", *Mol. Endocrinol.*, 1991, 5, 1246–1256.

Perri et al., "Interactions of Plasmid–encoded Replication Initiation Proteins with the Origin of DNA Replication in the Broad Host Range Plasmid RK2", *J. Biol. Chem.*, 1991, 266, 12536–12543.

Pushpa–Rekha et al., "Rat Phospholipid–hydroperoxide Glutathione Peroxidase", *J. Biol. Chem.*, 1995, 270, 26993.

Reiser et al., "Murine B7 antigen provides an efficient costimulatory signal for activation of murine T lymphocytes via the T–cell", *Proc. Natl. Acad. Sci. U.S.A.*, 1992, 89, 271–275.

Rogers et al., "Alternative splicing dictates translational start in Epstein–Barr virus transcripts", *EMBO J.*, 1990, 9, 2273–2277.

Romani et al., "Proliferating Dendritic Cell Progenitors in Human Blood", *J. Exp. Med.*, 1994, 180, 83–93.

Saison–Behmoaras et al., "Short modified antisense oligonucleotides directed against Ha–ras point mutation induce selective cleavage of the mRNA and inhibit T24 cells proliferation", *EMBO J.*, 1991, 10, 111–1118.

Sambrook et al., *Molecular Cloning. A Laboratory Manual*, Cold Spring Harbor Laboratory Press, 1989, vol. 2, pp. 10.59–10.61.

Sambrook et al., "Molecular Cloning. A Laboratory Manual," Cold Spring Harbor Laboratory Press, 1989, vol. 2, pp. 11.31–11.32.

Saul et al., "celB, a Gene Coding for a Bifunctional Cellulase from the Extreme Thermophile *Caldocellum saccharolyticum*", *Appl. Environ. Microbiol.*, 1990, 56, 3117–3124.

Sawai, H., "Synthesis and Properties of Some New 2–5A Analogues", *Chemica Scripta*, 1986, 21, 169–172.

Shea et al., "Synthesis, hybridization properties and antiviral activity of lipid–oligodeoxynucleotide conjugates", *Nucl. Acids Res.*, 1990, 18, 3777–3783.

Smith et al., "The Nucleic Acid of Polyoma Virus" *Virol.*, 1960, 12, 185–196.

Stepkowski et al., "Blocking of Heart Allograft Rejection by Intercellular Adhesion Molecule–1 Antisense Oligonucleotides Alone or in Combination with Other Immunosuppressive Modalities", *J. Immunol.*, 1994, 153, 5336–5346.

Svinarchuk et al., "Inhibition of HIV proliferation in MT–4 cells by antisense oligonucleotide conjugated to lipophilic groups", *Biochimie*, 1993, 75, 49–54.

Wu et al., "A Major Costimulatory Molecule on Antigen–presenting Cells, CTLA4 Ligand A, Is Distinct from B7", *J. Exp. Med.*, 1993, 178, 1789–1793.

Yang et al., "CD40 Ligand–Dependent T Cell Activation: Requirement of B7–CD28 Signaling Through CD40", *Science*, 1996, 273, 1862–1864.

Yaoita et al., "*Xenopus laevis* α and β thyroid hormone receptors", *Proc. Natl. Acad. Sci. USA*, 1990, 87, 7090–7094.

OLIGONUCLEOTIDE COMPOSITIONS AND METHODS FOR THE MODULATION OF THE EXPRESSION OF B7 PROTEIN

FIELD OF THE INVENTION

This invention relates to diagnostics, research reagents and therapeutics for disease states which respond to modulation of T cell activation. In particular, this invention relates to antisense oligonucleotide interactions with certain messenger ribonucleic acids (mRNAs) or DNAs involved in the synthesis of proteins that modulate T cell activation. Antisense oligonucleotides designed to hybridize to nucleic acids encoding B7 proteins are provided. These oligonucleotides have been found to lead to the modulation of the activity of the RNA or DNA, and thus to the modulation of T cell activation. Palliative, therapeutic and prophylactic effects result. The invention also relates to pharmaceutical compositions which comprise an antisense oligonucleotide to a B7 protein in combination with a second anti-inflammatory agent, such as a second antisense oligonucleotide to a protein which mediates intercellular interactions, e.g., an intercellular adhesion molecule (ICAM) protein.

BACKGROUND OF THE INVENTION

Inflammation is a localized protective response mounted by tissues in response to injury, infection, or tissue destruction resulting in the destruction of the infectious or injurious agent and isolation of the injured tissue. A typical inflammatory response proceeds as follows: recognition of an antigen as foreign or recognition of tissue damage, synthesis and release of soluble inflammatory mediators, recruitment of inflammatory cells to the site of infection or tissue damage, destruction and removal of the invading organism or damaged tissue, and deactivation of the system once the invading organism or damage has been resolved. In many human diseases with an inflammatory component, the normal, homeostatic mechanisms which attenuate the inflammatory responses are defective, resulting in damage and destruction of normal tissue.

Cell-cell interactions are involved in the activation of the immune response at each of the stages described above. One of the earliest detectable events in a normal inflammatory response is adhesion of leukocytes to the vascular endothelium, followed by migration of leukocytes out of the vasculature to the site of infection or injury. In general, the first inflammatory cells to appear at the site of inflammation are neutrophils, followed by monocytes and lymphocytes. Cell-cell interactions are also critical for activation of both B-lymphocytes (B cells) and T-lymphocytes (T cells) with resulting enhanced humoral and cellular immune responses, respectively.

The hallmark of the immune system is its ability to distinguish between self (host) and nonself (foreign invaders). This remarkable specificity exhibited by the immune system is mediated primarily by T cells. T cells participate in the host's defense against infection but also mediate organ damage of transplanted tissues and contribute to cell attack in graft-versus-host disease (GVHD) and some autoimmune diseases. In order to induce an antigen-specific immune response, a T cell must receive signals delivered by an antigen-presenting cell (APC). T cell-APC interactions can be divided into three stages: cellular adhesion, T cell receptor (TCR) recognition, and costimulation. At least two discrete signals are required from an APC for induction of T cell activation. The first signal is antigen-specific and is provided when the TCR interacts with an antigen in the context of a major histocompatibility complex (MHC) protein, or an MHC-related CD1 protein, expressed on the surface of an APC ("CD," standing for "cluster of differentiation," is a term used to denote different T cell surface molecules). The second (costimulatory) signal involves the interaction of the T cell surface antigen, CD28, with its ligand on the APC, which is a member of the B7 family of proteins.

CD28, a disulfide-linked homodimer of a 44 kilodalton polypeptide and a member of the immunoglobulin superfamily, is one of the major costimulatory signal receptors on the surface of a resting T cell for T cell activation and cytokine production (Allison, Curr. Opin. Immunol., 1994, 6, 414; Linsley and Ledbetter, Annu. Rev. Immunol., 1993, 11, 191; June et al., Immunol. Today, 1994, 15, 321). Signal transduction through CD28 acts synergistically with TCR signal transduction to augment both interleukin-2 (IL-2) production and proliferation of naive T cells. B7-1 (also known as CD80) was the first ligand identified for CD28 (Liu and Linsley, Curr. Opin. Immunol., 1992, 4, 265). B7-1 is normally expressed at low levels on APCs, however, it is upregulated following activation by cytokines or ligation of cell surface molecules such as CD40 (Lenschow et al., Proc. Natl. Acad. Sci. U.S.A., 1993, 90, 11054; Nabavi et al., Nature, 1992, 360, 266) Initial studies suggested that B7-1 was the CD28 ligand that mediated costimulation (Reiser et al., Proc. Natl. Acad. Sci. U.S.A., 1992, 89, 271; Wu et al., J. Exp. Med., 1993, 178, 1789; Harlan et al., Proc. Natl. Acad. Sci. U.S.A., 1994, 91, 3137). However, the subsequent demonstration that anti-B7-1 monoclonal antibodies (mAbs) had minimal effects on primary mixed lymphocyte reactions and that B7-1-deficient mice responded normally to antigens (Lenschow et al., Proc. Natl. Acad. Sci. U.S.A., 1993, 90, 11054; Freeman et al., Science, 1993, 262, 909) resulted in the discovery of a second ligand for the CD28 receptor, B7-2 (also known as CD86). In contrast with anti-B7-1 mAbs, anti-B7-2 mAbs are potent inhibitors of T cell proliferation and cytokine production (Wu et al., J. Exp. Med., 1993, 178, 1789; Chen et al., J. Immunol., 1994, 152, 2105; Lenschow et al., Proc. Natl. Acad. Sci. U.S.A., 1993, 90, 11054). B7:CD28 signaling may be a necessary component of other T cell costimulatory pathways, such as CD40:CD40L (CD40 ligand) signaling (Yang et al., Science, 1996, 273, 1862).

In addition to binding CD28, B7-1 and B7-2 bind the cytolytic T-lymphocyte associated protein CTLA4. CTLA4 is a protein that is structurally related to CD28 but is expressed on T cells only after activation (Linsley et al., J. Exp. Med., 1991, 174, 561). A soluble recombinant form of CTLA4, CTLA4-Ig, has been determined to be a more efficient inhibitor of the B7:CD28 interaction than monoclonal antibodies directed against CD28 or a B7 protein. In vivo treatment with CTLA4-Ig results in the inhibition of antibody formation to sheep red blood cells or soluble antigen (Linsley et al., Science, 1992, 257, 792), prolongation of cardiac allograft and pancreatic islet xenograft survival (Lin et al., J. Exp. Med., 1993, 178, 1801; Lenschow et al., 1992, Science, 257, 789; Lenschow et al., Curr. Opin. Immunol., 1993, 5(5) 747–52, and significant suppression of immune responses in GVHD (Hakim et al., J. Immun., 1995, 155, 1760). It has been proposed that CD28 and CTLA4, although both acting through common B7 receptors, serve opposing costimulatory and inhibitory functions, respectively (Allison et al., Science, 1995, 270, 932).

European Patent Application No. EP 0 600 591, published Jun. 8, 1994 (A2), discloses a method of inhibiting tumor cell growth in which tumor cells from a patient are recombinantly engineered ex vivo to express a B7-1 protein and then reintroduced into a patient. As a result, an immunologic response is stimulated against both B7-transfected and non-transfected tumor cells.

International Publication No. WO 95/03408, published Feb. 2, 1995, discloses nucleic acids encoding novel CTLA4/CD28 ligands which costimulate T cell activation, including B7-2 proteins. Also disclosed are antibodies to B7-2 proteins and methods of producing B7-2 proteins.

International Publication No. WO 95/05464, published Feb. 23, 1995, discloses a polypeptide, other than B7-1, that binds to CTLA4, CD28 or CTLA4-Ig. Also disclosed are methods for obtaining a nucleic acid encoding such a polypeptide.

International Publication No. WO 95/06738, published Mar. 9, 1995, discloses nucleic acids encoding B7-2 (also known as B70) proteins. Also disclosed are antibodies to B7-2 proteins and methods of producing B7-2 proteins.

European Patent Application No. EP 0 643 077, published Mar. 15, 1995 (A1), discloses a monoclonal antibody which specifically binds a B7-2 (also known as B70) protein. Also disclosed are methods of producing monoclonal antibodies which specifically bind a B7-2 protein.

U.S. Pat. No. 5,434,131, issued Jul. 18, 1995, discloses the CTLA4 protein as a ligand for B7 proteins. Also disclosed are methods of producing CTLA4 fusion proteins (e.g., CTLA4-Ig) and methods of regulating immune responses using antibodies to B7 proteins or CTLA4 proteins.

International Publication No. WO 95/22619, published Aug. 24, 1995, discloses antibodies specific to B7-1 proteins which do not bind to B7-2 proteins. Also disclosed are methods of regulating immune responses using antibodies to B7-1 proteins.

International Publication No. WO 95/34320, published Dec. 21, 1995, discloses methods for inhibiting T cell responses using a first agent which inhibits a costimulatory agent, such as an CTLA4-Ig fusion protein, and a second agent which inhibits cellular adhesion, such as an anti-LFA-1 antibody. Such methods are indicated to be particularly useful for inhibiting the rejection of transplanted tissues or organs.

International Publication No. WO 95/32734, published Dec. 7, 1995, discloses FcγRII bridging agents which either prevent the upregulation of B7 molecules or impair the expression of ICAM-3 on antigen presenting cells. Such FcγRII bridging agents include proteins such as aggregated human IgG molecules or aggregated Fc fragments of human IgG molecules.

International Publication No. WO 96/11279, published Apr. 18, 1996 (A2) and May 17, 1996 (A3), discloses recombinant viruses comprising genetic sequences encoding (1) one or more immunostimulatory agents, including B7-1 and B7-2, and (2) and antigens from a disease causing agent. Also disclosed are methods of treating diseases using such recombinant viruses.

To date, there are no known therapeutic agents which effectively regulate and prevent the expression of B7 proteins such as B7-1 and B7-2. Thus, there is a long-felt need for compounds and methods which effectively modulate critical costimulatory molecules such as the B7 proteins. It is anticipated that oligonucleotides capable of modulating the expression of B7 proteins provide for a novel therapeutic class of anti-inflammatory agents with activity towards a variety of inflammatory or autoimmune diseases, or disorders or diseases with an inflammatory component such as asthma, juvenile diabetes mellitus, myasthenia gravis, Graves' disease, rheumatoid arthritis, allograft rejection, inflammatory bowel disease, multiple sclerosis, psoriasis, lupus erythematosus, systemic lupus erythematosus, diabetes, multiple sclerosis, contact dermatitis, rhinitis and various allergies. In addition, oligonucleotides capable of modulating the expression of B7 proteins would provide a novel means of manipulating the ex vivo proliferation of T cells.

SUMMARY OF THE INVENTION

In accordance with the present invention, oligonucleotides are provided which specifically hybridize with nucleic acids encoding B7-1 or B7-2. Certain oligonucleotides of the invention are designed to bind either directly to mRNA transcribed from, or to a selected DNA portion of, the B7-1 or B7-2 gene, thereby modulating the amount of protein translated from a B7-1 or B7-2 mRNA or the amount of mRNA transcribed from a B7-1 or B7-2 gene, respectively.

Oligonucleotides may comprise nucleotide sequences sufficient in identity and number to effect specific hybridization with a particular nucleic acid. Such oligonucleotides are commonly described as "antisense." Antisense oligonucleotides are commonly used as research reagents, diagnostic aids, and therapeutic agents.

It has been discovered that the B7-1 and B7-2 genes, encoding B7-1 and B7-2 proteins, respectively, are particularly amenable to this approach. As a consequence of the association between B7 expression and T cell activation and proliferation, inhibition of the expression of B7-1 or B7-2 leads to inhibition of the synthesis of B7-1 or B7-2, respectively, and thereby inhibition of T cell activation and proliferation. Additionally, the oligonucleotides of the invention may be used to inhibit the expression of one of several alternatively spliced mRNAs of a B7 transcript, resulting in the enhanced expression of other alternatively spliced B7 mRNAs. Such modulation is desirable for treating various inflammatory or autoimmune disorders or diseases, or disorders or diseases with an inflammatory component such as asthma, juvenile diabetes mellitus, myasthenia gravis, Graves' disease, rheumatoid arthritis, allograft rejection, inflammatory bowel disease, multiple sclerosis, psoriasis, lupus erythematosus, systemic lupus erythematosus, diabetes, multiple sclerosis, contact dermatitis, rhinitis, various allergies, and cancers and their metastases. Such modulation is further desirable for preventing or modulating the development of such diseases or disorders in an animal suspected of being, or known to be, prone to such diseases or disorders.

Methods comprising contacting animals with oligonucleotides specifically hybridizable with nucleic acids encoding B7 proteins are herein provided. These methods are useful as tools, for example, in the detection and determination of the role of B7 protein expression in various cell functions and physiological processes and conditions, and for the diagnosis of conditions associated with such expression. Such methods can be used to detect the expression of B7 genes (i.e., B7-1 or B7-2) and are thus believed to be useful both therapeutically and diagnostically. Methods of modulating the expression of B7 proteins comprising contacting animals with oligonucleotides specifically hybridizable with a B7 gene are herein provided. These methods are believed to be useful both therapeutically and diagnostically as a consequence of the association between B7 expression and T cell activation and proliferation. The present invention also comprises methods of inhibiting B7-associated activation of T cells using the oligonucleotides of the invention. Methods of treating conditions in which abnormal or excessive T cell activation and proliferation occurs are also provided. These methods employ the oligonucleotides of the invention and are believed to be useful both therapeutically and as clinical research and diagnostic tools. The oligonucleotides of the present invention may also be used for research purposes. Thus, the specific hybridization exhibited by the oligonucleotides of the present invention may be used for assays, purifications, cellular product preparations and in other methodologies which may be appreciated by persons of ordinary skill in the art.

The methods disclosed herein are also useful, for example, as clinical research tools in the detection and determination of the role of B7-1 or B7-2 expression in various immune system functions and physiological processes and conditions, and for the diagnosis of conditions associated with their expression. The specific hybridization exhibited by the oligonucleotides of the present invention may be used for assays, purifications, cellular product preparations and in other methodologies which may be appreciated by persons of ordinary skill in the art. For example, because the oligonucleotides of this invention specifically hybridize to nucleic acids encoding B7 proteins, sandwich and other assays can easily be constructed to exploit this fact. Detection of specific hybridization of an oligonucleotide of the invention with a nucleic acid encoding a B7 protein present in a sample can routinely be accomplished. Such detection may include detectably labeling an oligonucleotide of the invention by enzyme conjugation, radiolabeling or any other suitable detection system. A number of assays may be formulated employing the present invention, which assays will commonly comprise contacting a tissue or cell sample with a detectably labeled oligonucleotide of the present invention under conditions selected to permit hybridization and measuring such hybridization by detection of the label, as is appreciated by hose of ordinary skill in the art.

DETAILED DESCRIPTION OF THE INVENTION

Figure 1:
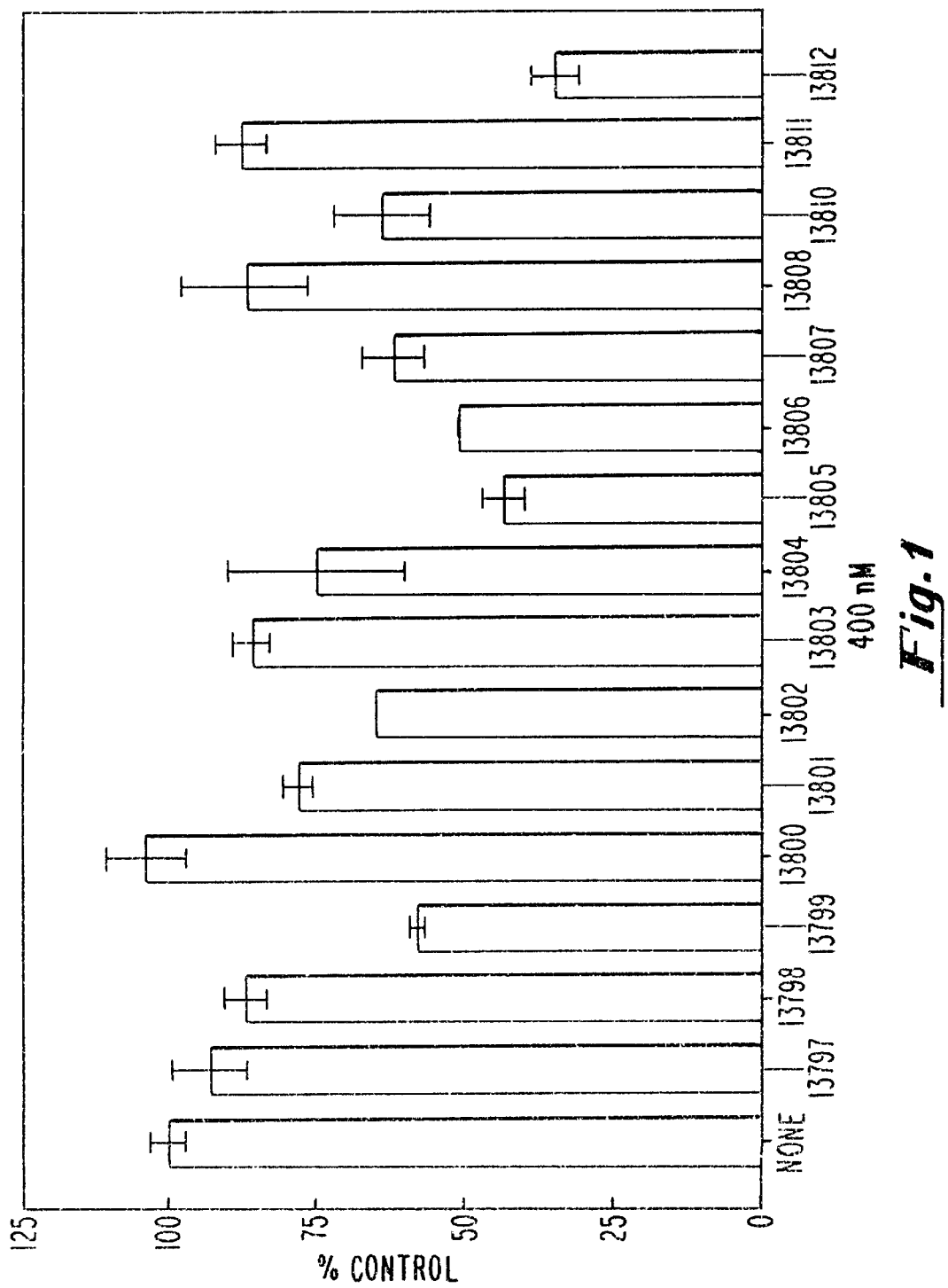
FIG. 1 is a bar graph showing the inhibitory effect of the indicated oligonucleotides on B7-1 protein expression in COS-7 cells.

The present invention employs oligonucleotides for use in antisense inhibition of the function of RNA and DNA encoding B7 proteins including B7-1 and B7-2. The present invention also employs oligonucleotides which are designed to be specifically hybridizable to DNA or messenger RNA (mRNA) encoding such proteins and ultimately to modulate the amount of such proteins transcribed from their respective genes. Such hybridization with mRNA interferes with the normal role of mRNA and causes a modulation of its function in cells. The functions of mRNA to be interfered with include all vital functions such as translocation of the RNA to the site for protein translation, actual translation of protein from the RNA, splicing of the RNA to yield one or more mRNA species, and possibly even independent catalytic activity which may be engaged in by the RNA. The overall effect of such interference with mRNA function is modulation of the expression of a B7 protein, wherein "modulation" means either an increase (stimulation) or a decrease (inhibition) in the expression of a B7 protein. In the context of the present invention, inhibition is the preferred form of modulation of gene expression.

Oligonucleotides may comprise nucleotide sequences sufficient in identity and number to effect specific hybridization with a particular nucleic acid. Such oligonucleotides which specifically hybridize to a portion of the sense strand of a gene are commonly described as "antisense." Antisense oligonucleotides are commonly used as research reagents, diagnostic aids, and therapeutic agents. For example, antisense oligonucleotides, which are able to inhibit gene expression with exquisite specificity, are often used by those of ordinary skill to elucidate the function of particular genes, for example to distinguish between the functions of various members of a biological pathway. This specific inhibitory effect has, therefore, been harnessed by those skilled in the art for research uses.

The specificity and sensitivity of oligonucleotides is also harnessed by those of skill in the art for therapeutic uses. For example, the following U.S. patents demonstrate palliative, therapeutic and other methods utilizing antisense oligonucleotides. U.S. Pat. No. 5,135,917 provides antisense oligonucleotides that inhibit human interleukin-1 receptor expression. U.S. Pat. No. 5,098,890 is directed to antisense oligonucleotides complementary to the c-myb oncogene and antisense oligonucleotide therapies for certain cancerous conditions. U.S. Pat. No. 5,087,617 provides methods for treating cancer patients with antisense oligonucleotides. U.S. Pat. No. 5,166,195 provides oligonucleotide inhibitors of HIV. U.S. Pat. No. 5,004,810 provides oligomers capable of hybridizing to herpes simplex virus Vmw65 mRNA and inhibiting replication. U.S. Pat. No. 5,194,428 provides antisense oligonucleotides having antiviral activity against influenzavirus. U.S. Pat. No. 4,806,463 provides antisense oligonucleotides and methods using them to inhibit HTLV-III replication. U.S. Pat. No. 5,286,717 provides oligonucleotides having a complementary base sequence to a portion of an oncogene. U.S. Pat. No. 5,276,019 and U.S. Pat. No. 5,264,423 are directed to phosphorothioate oligonucleotide analogs used to prevent replication of foreign nucleic acids in cells. U.S. Pat. No. 4,689,320 is directed to antisense oligonucleotides as antiviral agents specific to CMV. U.S. Pat. No. 5,098,890 provides oligonucleotides complementary to at least a portion of the mRNA transcript of the human c-myb gene. U.S. Pat. No. 5,242,906 provides antisense oligonucleotides useful in the treatment of latent EBV infections.

It is preferred to target specific genes for antisense attack. "Targeting" an oligonucleotide to the associated nucleic acid, in the context of this invention, is a multistep process. The process usually begins with the identification of a nucleic acid sequence whose function is to be modulated. This may be, for example, a cellular gene (or mRNA transcribed from the gene) whose expression is associated with a particular disorder or disease state, or a foreign nucleic acid from an infectious agent. In the present invention, the target is a cellular gene associated with several immune system disorders and diseases (such as inflammation and autoimmune diseases), as well as with ostensibly "normal" immune reactions (such as a host animal's rejection of transplanted tissue), for which modulation is desired in certain instances. The targeting process also includes determination of a region (or regions) within this gene for the oligonucleotide interaction to occur such that the desired effect, either detection or modulation of expression of the protein, will result. Once the target region have been identified, oligonucleotides are chosen which are sufficiently complementary to the target, i.e., hybridize sufficiently well and with sufficient specificity to give the desired effect.

Generally, there are five regions of a gene that may be targeted for antisense modulation: the 5' untranslated region (hereinafter, the "5'-UTR"), the translation initiation codon region (hereinafter, the "tIR"), the open reading frame (hereinafter, the "ORF"), the translation termination codon region (hereinafter, the "tTR") and the 3' untranslated region (hereinafter, the "3'-UTR"). As is known in the art, these regions are arranged in a typical messenger RNA molecule in the following order (left to right, 5' to 3'): 5'-UTR, tIR, ORF, tTR, 3'-UTR. As is known in the art, although some eukaryotic transcripts are directly translated, many ORFs contain one or more sequences, known as "introns," which are excised from a transcript before it is translated; the expressed (unexcised) portions of the ORF are referred to as "exons" (Alberts et al., *Molecular Biology of the Cell*, 1983, Garland Publishing Inc., New York, pp. 411–415). Furthermore, because many eukaryotic ORFs are a thousand nucleotides or more in length, it is often convenient to subdivide the ORF into, e.g., the 5' ORF region, the central ORF region, and the 3' ORF region. In some instances, an ORF contains one or more sites that may be targeted due to some functional significance in vivo. Examples of the latter types of sites include intragenic stem-loop structures (see, e.g., U.S. Pat. No. 5,512,438) and, in unprocessed mRNA molecules, intron/exon splice sites. Within the context of the present invention, one preferred intragenic site is the region encompassing the translation initiation codon of the open reading frame (ORF) of the gene. Because, as is known in the art, the translation initiation codon is typically 5'-AUG (in transcribed mRNA molecules; 5'-ATG in the corresponding DNA molecule), the translation initiation codon is also referred to as the "AUG codon," the "start codon" or the "AUG start codon." A minority of genes have a translation initiation codon having the RNA sequence 5'-GUG, 5'-UUG or 5'-CUG, and 5'-AUA, 5'-ACG and 5'-CUG have been shown to function in vivo. Furthermore, 5'-UUU functions as a translation initiation codon in vitro (Brigstock et al., *Growth Factors*, 1990, 4, 45; Gelbert et al., *Somat. Cell. Mol. Genet.*, 1990, 16, 173; Gold and Stormo, in: *Escherichia coli and Salmonella typhimurium: Cellular and Molecular Biology*, Vol. 2, 1987, Neidhardt et al., eds., American Society for Microbiology, Washington, D.C., p. 1302). Thus, the terms "translation initiation codon" and "start codon" can encompass many codon sequences, even though the initiator amino acid in each instance is typically methionine (in eukaryotes) or formylmethionine (prokaryotes). It is also known in the art that eukaryotic and prokaryotic genes may have two or more alternative start codons, any one of which may be preferentially utilized for translation initiation in a particular cell type or tissue, or under a particular set of conditions, in order to generate related polypeptides having different amino terminal sequences (Markussen et al., *Development*, 1995, 121, 3723; Gao et al., *Cancer Res.*, 1995, 55, 743; McDermott et al., *Gene*, 1992, 117, 193; Perri et al., *J. Biol. Chem.*, 1991, 266, 12536; French et al., *J. Virol.*, 1989, 63, 3270; Pushpa-Rekha et al., *J. Biol. Chem.*, 1995, 270, 26993; Monaco et al., *J. Biol. Chem.*, 1994, 269, 347; DeVirgilio et al., *Yeast*, 1992, 8, 1043; Kanagasundaram et al., *Biochim. Biophys. Acta*, 1992, 1171, 198; Olsen et al., *Mol. Endocrinol.*, 1991, 5, 1246; Saul et al., *Appl. Environ. Microbiol.*, 1990, 56, 3117; Yaoita et al., *Proc. Natl. Acad. Sci. USA*, 1990, 87, 7090; Rogers et al., *EMBO J.*, 1990, 9, 2273). In the context of the invention, "start codon" and "translation initiation codon" refer to the codon or codons that are used in vivo to initiate translation of an mRNA molecule transcribed from a gene encoding a B7 protein, regardless of the sequence(s) of such codons. It is also known in the art that a translation termination codon (or "stop codon") of a gene may have one of three sequences, i.e., 5'-UAA, 5'-UAG and 5'-UGA (the corresponding DNA sequences are 5'-TAA, 5'-TAG and 5'-TGA, respectively). The terms "start codon region" and "translation initiation region" refer to a portion of such an mRNA or gene that encompasses from about 25 to about 50 contiguous nucleotides in either direction (i.e., 5' or 3') from a translation initiation codon. Similarly, the terms "stop codon region" and "translation termination region" refer to a portion of such an mRNA or gene that encompasses from about 25 to about 50 contiguous nucleotides in either direction (i.e., 5' or 3') from a translation termination codon.

In the context of this invention, the term "oligonucleotide" refers to an oligomer or polymer of ribonucleic acid or deoxyribonucleic acid. This term includes oligonucleotides composed of naturally-occurring nucleobases, sugars and covalent intersugar (backbone) linkages as well as oligonucleotides having non-naturally-occurring portions which function similarly. Such modified or substituted oligonucleotides are often preferred over native forms because of desirable properties such as, for example, enhanced cellular uptake, enhanced binding to target and increased stability in the presence of nucleases.

Specific examples of some preferred modified oligonucleotides envisioned for this invention include those containing phosphorothioates, phosphotriesters, methyl phosphonates, short chain alkyl or cycloalkyl intersugar linkages or short chain heteroatomic or heterocyclic intersugar linkages. Most preferred are oligonucleotides with phosphorothioates and those with $CH_2$—NH—O—$CH_2$, $CH_2$—N($CH_3$)—O—$CH_2$

[known as a methylene(methylimino) or MMI backbone], $CH_2$—O—$N(CH_3)$ —$CH_2$, $CH_2$—$N(CH_3)$ —$N(CH_3)$ —$CH_2$ and O—$N(CH_3)$ —$CH_2$—$CH_2$ backbones, wherein the native phosphodiester backbone is represented as O—P—O—$CH_2$). Also preferred are oligonucleotides having morpholino backbone structures (Summerton and Weller, U.S. Pat. No. 5,034,506). Further preferred are oligonucleotides with NR—C(*)—$CH_2$—$CH_2$, $CH_2$—NR—C(*)—$CH_2$, $CH_2$—$CH_2$—NR—C(*), C(*)—NR—$CH_2$—$CH_2$ and $CH_2$—C(*)—NR—$CH_2$ backbones, wherein "*" represents O or S (known as amide backbones; DeMesmaeker et al., WO 92/20823, published Nov. 26, 1992). In other preferred embodiments, such as the peptide nucleic acid (PNA) backbone, the phosphodiester backbone of the oligonucleotide is replaced with a polyamide backbone, the nucleobases being bound directly or indirectly to the aza nitrogen atoms of the polyamide backbone (Nielsen et al., *Science*, 1991, 254, 1497; U.S. Pat. No. 5,539,082). Other preferred modified oligonucleotides may contain one or more substituted sugar moieties comprising one of the following at the 2' position: OH, SH, $SCH_3$, F, OCN, $OCH_3OCH_3$, $OCH_3O(CH_2)_nCH_3$, $O(CH_2)_nNH_2$ or $O(CH_2)_nCH_3$ where n is from 1 to about 10; $C_1$ to $C_{10}$ lower alkyl, alkoxyalkoxy, substituted lower alkyl, alkaryl or aralkyl; Cl; Br; CN; $CF_3$; $OCF_3$; O—, S—, or N-alkyl; O—, S—, or N-alkenyl; $SOCH_3$; $SO_2CH_3$; $ONO_2$; $NO_2$; $N_3$; $NH_2$; heterocycloalkyl; heterocycloalkaryl; aminoalkylamino; polyalkylamino; substituted silyl; an RNA cleaving group; a reporter group; an intercalator; a group for improving the pharmacokinetic properties of an oligonucleotide; or a group for improving the pharmacodynamic properties of an oligonucleotide and other substituents having similar properties. A preferred modification includes 2'-methoxyethoxy [2'-O—$CH_2CH_2OCH_3$, also known as 2'-O-(2-methoxyethyl)] (Martin et al., *Helv. Chim. Acta*, 1995, 78, 486). Other preferred modifications include 2'-methoxy (2'-O—$CH_3$), 2'-propoxy (2'-O—$CH_2CH_2CH_3$) and 2'-fluoro (2'-F). Similar modifications may also be made at other positions on the oligonucleotide, particularly the 3' position of the sugar on the 3' terminal nucleotide and the 5' position of the 5' terminal nucleotide. Oligonucleotides may also have sugar mimetics such as cyclobutyls in place of the pentofuranosyl group.

The oligonucleotides of the invention may additionally or alternatively include nucleobase modifications or substitutions. As used herein, "unmodified" or "natural" nucleobases include adenine (A), guanine (G), thymine (T), cytosine (C) and uracil (U). Modified nucleobases include nucleobases found only infrequently or transiently in natural nucleic acids, e.g., hypoxanthine, 6-methyladenine, 5-methylcytosine, 5-hydroxymethylcytosine (HMC), glycosyl HMC and gentiobiosyl HMC, as well synthetic nucleobases, e.g., 5-bromouracil, 5-hydroxymethyluracil, 8-azaguanine, 7-deazaguanine, $N^6$(6-aminohexyl)adenine and 2,6-diaminopurine (Kornberg, A., DNA Replication, 1974, W. H. Freeman & Co., San Francisco, 1974, pp. 75–77; Gebeyehu, G., et al., *Nucleic Acids Res.*, 1987, 15, 4513).

Another preferred additional or alternative modification of the oligonucleotides of the invention involves chemically linking to the oligonucleotide one or more lipophilic moieties which enhance the cellular uptake of the oligonucleotide. Such lipophilic moieties may be linked to an oligonucleotide at several different positions on the oligonucleotide. Some preferred positions include the 3' position of the sugar of the 3' terminal nucleotide, the 5' position of the sugar of the 5' terminal nucleotide, and the 2' position of the sugar of any nucleotide. The $N^6$ position of a purine nucleobase may also be utilized to link a lipophilic moiety to an oligonucleotide of the invention (Gebeyehu, G., et al., *Nucleic Acids Res.*, 1987, 15, 4513). Such lipophilic moieties include but are not limited to a cholesteryl moiety (Letsinger et al., *Proc. Natl. Acad. Sci. USA*, 1989, 86, 6553), cholic acid (Manoharan et al., *Bioorg. Med. Chem. Let.*, 1994, 4, 1053), a thioether, e.g., hexyl-S-tritylthiol (Manoharan et al.,*Ann. N.Y. Acad. Sci.*, 1992, 660, 306; Manoharan et al., *Bioorg. Med. Chem. Let.*, 1993, 3, 2765), a thiocholesterol (Oberhauser et al., *Nucl. Acids Res.*, 1992, 20, 533), an aliphatic chain, e.g., dodecandiol or undecyl residues (Saison-Behmoaras et al., *EMBO J.*, 1991, 10, 111; Kabanov et al., *FEBS Lett.*, 1990, 259, 327; Svinarchuk et al., *Biochimie*, 1993, 75, 49), a phospholipid, e.g., di-hexadecyl-rac-glycerol or triethylammonium 1,2-di-O-hexadecyl-rac-glycero-3-H-phosphonate (Manoharan et al., *Tetrahedron Lett.*, 1995, 36, 3651; Shea et al., *Nucl. Acids Res.*, 1990, 18, 3777), a polyamine or a polyethylene glycol chain (Manoharan et al., *Nucleosides & Nucleotides*, 1995, 14, 969), or adamantane acetic acid (Manoharan et al., *Tetrahedron Lett.*, 1995, 36, 3651), a palmityl moiety (Mishra et al., *Biochim. Biophys. Acta*, 1995, 1264, 229), or an octadecylamine or hexylamino-carbonyl-oxycholesterol moiety (Crooke et al., *J. Pharmacol. Exp. Ther.*, 1996, 277, 923). Oligonucleotides comprising lipophilic moieties, and methods for preparing such oligonucleotides, as disclosed in U.S. Pat. No. 5,138,045, No. 5,218,105 and No. 5,459,255, the contents of which are hereby incorporated by reference.

The present invention also includes oligonucleotides which are chimeric oligonucleotides. "Chimeric" oligonucleotides or "chimeras," in the context of this invention, are oligonucleotides which contain two or more chemically distinct regions, each made up of at least one nucleotide. These oligonucleotides typically contain at least one region wherein the oligonucleotide is modified so as to confer upon the oligonucleotide increased resistance to nuclease degradation, increased cellular uptake, and/or increased binding affinity for the target nucleic acid. An additional region of the oligonucleotide may serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of antisense inhibition of gene expression. Cleavage of the RNA target can be routinely detected by gel electrophoresis and, if necessary, associated nucleic acid hybridization techniques known in the art. By way of example, such "chimeras" may be "gapmers," i.e., oligonucleotides in which a central portion (the "gap") of the oligonucleotide serves as a substrate for, e.g., RNase H, and the 5' and 3' portions (the "wings") are modified in such a fashion so as to have greater affinity for the target RNA molecule but are unable to support nuclease activity (e.g., 2'-fluoro- or 2'-methoxyethoxy substituted). Other chimeras include "wingmers," that is, oligonucleotides in which the 5' portion of the oligonucleotide serves as a substrate for, e.g., RNase H, whereas the 3' portion is modified in such a fashion so as to have greater affinity for the target RNA molecule but is unable to support nuclease activity (e.g., 2'-fluoro- or 2' methoxyethoxy substituted), or vice-versa.

The oligonucleotides in accordance with this invention preferably comprise from about 8 to about 30 nucleotides. It is more preferred that such oligonucleotides comprise from about 15 to 25 nucleotides. As is known in the art, a nucleotide is a base-sugar combination suitably bound to an adjacent nucleotide through a phosphodiester, phosphorothioate or other covalent linkage.

The oligonucleotides used in accordance with this invention may be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is also known to use similar techniques to prepare other oligonucleotides such as the phosphorothioates and alkylated derivatives.

The oligonucleotides of the present invention can be utilized as therapeutic compounds, diagnostic tools and as research reagents and kits. The term "therapeutic uses" is intended to encompass prophylactic, palliative and curative uses wherein the oligonucleotides of the invention are contacted with animal cells either in vivo or ex vivo. When contacted with animal cells ex vivo, a therapeutic use includes incorporating such cells into an animal after treatment with one or more oligonucleotides of the invention. While not intending to be bound to a particular utility, the ex vivo modulation of, e.g., T cell proliferation by the oligonucleotides of the invention can be employed in, for example, potential therapeutic modalities wherein it is desired to modulate the expression of a B7 protein in APCs. As an example, oligonucleotides that inhibit the expression of B7-1 proteins are expected to enhance the availability of B7-2 proteins on the surface of APCs, thus increasing the costimulatory effect of B7-2 on T cells ex vivo (Levine et al., *Science*, 1996, 272, 1939).

For therapeutic uses, an animal suspected of having a disease or disorder which can be treated or prevented by modulating the expression or activity of a B7 protein is, for example, treated by administering oligonucleotides in accordance with this invention. The oligonucleotides of the invention can be utilized in pharmaceutical compositions by adding an effective amount of an oligonucleotide to a suitable pharmaceutically acceptable diluent or carrier. Workers in the field have identified antisense, triplex and other oligonucleotide compositions which are capable of modulating expression of genes implicated in viral, fungal and metabolic diseases. Antisense oligonucleotides have been safely administered to humans and several clinical trials are presently underway. It is thus established that oligonucleotides can be useful therapeutic instrumentalities that can be configured to be useful in treatment regimes for treatment of cells, tissues and animals, especially humans.

The oligonucleotides of the present invention can be further used to detect the presence of B7-specific nucleic acids in a cell or tissue sample. For example, radiolabeled oligonucleotides can be prepared by $^{32}P$ labeling at the 5' end with polynucleotide kinase (Sambrook et al., *Molecular Cloning. A Laboratory Manual*, Cold Spring Harbor Laboratory Press, 1989, Volume 2, pg. 10.59). Radiolabeled oligonucleotides are then contacted with cell or tissue samples suspected of containing B7 message RNAs (and thus B7 proteins), and the samples are washed to remove unbound oligonucleotide. Radioactivity remaining in the sample indicates the presence of bound oligonucleotide, which in turn indicates the presence of nucleic acids complementary to the oligonucleotide, and can be quantitated using a scintillation counter or other routine means. Expression of nucleic acids encoding these proteins is thus detected.

Radiolabeled oligonucleotides of the present invention can also be used to perform autoradiography of tissues to determine the localization, distribution and quantitation of B7 proteins for research, diagnostic or therapeutic purposes. In such studies, tissue sections are treated with radiolabeled oligonucleotide and washed as described above, then exposed to photographic emulsion according to routine autoradiography procedures. The emulsion, when developed, yields an image of silver grains over the regions expressing a B7 gene. Quantitation of the silver grains permits detection of the expression of mRNA molecules encoding these proteins and permits targeting of oligonucleotides to these areas.

Analogous assays for fluorescent detection of expression of B7 nucleic acids can be developed using oligonucleotides of the present invention which are conjugated with fluorescein or other fluorescent tags instead of radiolabeling. Such conjugations are routinely accomplished during solid phase synthesis using fluorescently-labeled amidites or controlled pore glass (CPG) columns. Fluorescein-labeled amidites and CPG are available from, e.g., Glen Research, Sterling Va.

The present invention employs oligonucleotides targeted to nucleic acids encoding B7 proteins and oligonucleotides targeted to nucleic acids encoding such proteins. Kits for detecting the presence or absence of expression of a B7 protein may also be prepared. Such kits include an oligonucleotide targeted to an appropriate gene, i.e., a gene encoding a B7 protein. Appropriate kit and assay formats, such as, e.g., "sandwich" assays, are known in the art and can easily be adapted for use with the oligonucleotides of the invention. Hybridization of the oligonucleotides of the invention with a nucleic acid encoding a B7 protein can be detected by means known in the art. Such means may include conjugation of an enzyme to the oligonucleotide, radiolabelling of the oligonucleotide or any other suitable detection systems. Kits for detecting the presence or absence of a B7 protein may also be prepared.

In the context of this invention, "hybridization" means hydrogen bonding, which may be Watson-Crick, Hoogsteen or reversed Hoogsteen hydrogen bonding, between complementary nucleotides. For example, adenine and thymine are complementary nucleobases which pair through the formation of hydrogen bonds. "Complementary," as used herein, refers to the capacity for precise pairing between two nucleotides. For example, if a nucleotide at a certain position of an oligonucleotide is capable of hydrogen bonding with a nucleotide at the same position of a DNA or RNA molecule, then the oligonucleotide and the DNA or RNA are considered to be complementary to each other at that position. The oligonucleotide and the DNA or RNA are complementary to each other when a sufficient number of corresponding positions in each molecule are occupied by nucleotides which can hydrogen bond with each other. Thus, "specifically hybridizable" and "complementary" are terms which are used to indicate a sufficient degree of complementarity or precise pairing such that stable and specific binding occurs between the oligonucleotide and the DNA or RNA target. It is understood in the art that an oligonucleotide need not be 100% complementary to its target DNA sequence to be specifically hybridizable. An oligonucleotide is specifically hybridizable when binding of the oligonucleotide to the target DNA or RNA molecule interferes with the normal function of the target DNA or RNA to cause a decrease or loss of function, and there is a sufficient degree of complementarity to avoid non-specific binding of the oligonucleotide to non-target sequences under conditions in which specific binding is desired, i.e., under physiological conditions in the case of in vivo assays or therapeutic treatment, or in the case of in vitro assays, under conditions in which the assays are performed.

The formulation of therapeutic compositions and their subsequent administration is believed to be within the skill of those in the art. In general, for therapeutics, a patient in need of such therapy is administered an oligonucleotide in accordance with the invention, commonly in a pharmaceutically acceptable carrier, in doses ranging from 0.01 μg to 100 g per kg of body weight depending on the age of the patient and the severity of the disorder or disease state being treated. Further, the treatment regimen may last for a period of time which will vary depending upon the nature of the particular disease or disorder, its severity and the overall condition of the patient, and may extend from once daily to once every 20 years. Following treatment, the patient is monitored for changes in his/her condition and for alleviation of the symptoms of the disorder or disease state. The dosage of the oligonucleotide may either be increased in the event the patient does not respond significantly to current dosage levels, or the dose may be decreased if an alleviation of the symptoms of the disorder or disease state is observed, or if the disorder or disease state has been ablated.

In some cases, it may be more effective to treat a patient with an oligonucleotide of the invention in conjunction with other therapeutic modalities in order to increase the efficacy of a treatment regimen. In the context of the invention, the term "treatment regimen" is meant to encompass therapeutic, palliative and prophylactic modalities. In a preferred embodiment, the oligonucleotides of the invention are used in conjunction with one or more antisense oligonucleotides targeted to an intercellular adhesion molecule (ICAM), preferably to ICAM-1. Other anti-inflammatory and/or immunosuppressive agents that may be used in combination with the oligonucleotides of the invention include, but are not limited to, soluble ICAM proteins (e.g., sICAM-1), antibody-toxin conjugates, prednisone, methylprednisolone, azathioprine, cyclophosphamide, cyclosporine, interferons, sympathomimetics, conventional antihistamines (histamine $H_1$ receptor antagonists, including, for example, brompheniramine maleate, chlorpheniramine maleate, dexchlorpheniramine maleate, tripolidine HCl, carbinoxamine maleate, clemastine fumarate, dimenhydrinate, diphenhydramine HCl, diphenylpyraline HCl, doxylamine succinate, tripelennamine citrate, tripelennamine HCl, cyclizine HCl, hydroxyzine HCl, meclizine HCl, methdilazine HCl, promethazine HCl, trimeprazine tartrate, azatadine maleate, cyproheptadine HCl, terfenadine, etc.), histamine $H_2$ receptor antagonists (e.g., ranitidine). See, generally, *The Merck Manual of Diagnosis and Therapy*, 15th Ed., Berkow et al., eds., 1987, Rahway, N.J., pages 302–336 and 2516–2522). When used with the compounds of the invention, such agents may be used individually, sequentially, or in combination with one or more other such agents.

In another preferred embodiment of the invention, an antisense oligonucleotide targeted to one B7 mRNA species (e.g., B7-1) is used in combination with an antisense oligonucleotide targeted to a second B7 mRNA species (e.g., B7-2) in order to inhibit the costimulatory effect of B7 molecules to a more extensive degree than can be achieved with either oligonucleotide used individually. In a related version of this embodiment, two or more oligonucleotides of the invention, each targeted to an alternatively spliced B7-1 or B7-2 mRNA, are combined with each other in order to inhibit expression of both forms of the alternatively spliced mRNAs. It is known in the art that, depending on the specificity of the modulating agent employed, inhibition of one form of an alternatively spliced mRNA may not result in a sufficient reduction of expression for a given condition to be manifest. Thus, such combinations may, in some instances, be desired to inhibit the expression of a particular B7 gene to an extent necessary to practice one of the methods of the invention.

Following successful treatment, it may be desirable to have the patient undergo maintenance therapy to prevent the recurrence of the disease state, wherein the oligonucleotide is administered in maintenance doses, ranging from 0.01 μg to 100 g per kg of body weight, once or more daily, to once every 20 years. In the case of in individual known or suspected of being prone to an autoimmune or inflammatory condition, prophylactic effects may be achieved by administration of preventative doses, ranging from 0.01 μg to 100 g per kg of body weight, once or more daily, to once every 20 years. In like fashion, an individual may be made less susceptible to an inflammatory condition that is expected to occur as a result of some medical treatment, e.g., graft versus host disease resulting from the transplantation of cells, tissue or an organ into the individual.

The pharmaceutical compositions of the present invention may be administered in a number of ways depending upon whether local or systemic treatment is desired and upon the area to be treated. Administration may be topical (including ophthalmic, vaginal, rectal, intranasal, transdermal), oral or parenteral. Parenteral administration includes intravenous drip, subcutaneous, intraperitoneal or intramuscular injection, or intrathecal or intraventricular administration.

Formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful.

Compositions for oral administration include powders or granules, suspensions or solutions in water or non-aqueous media, capsules, sachets or tablets. Thickeners, flavoring agents, diluents, emulsifiers, dispersing aids or binders may be desirable.

Compositions for parenteral, intrathecal or intraventricular administration may include sterile aqueous solutions which may also contain buffers, diluents and other suitable additives.

Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual oligonucleotides, and can generally be estimated based on $EC_{50}$s found to be effective in in vitro and in vivo animal models. In general, dosage is from 0.01 μg to 100 g per kg of body weight, and may be given once or more daily, weekly, monthly or yearly, or even once every 2 to 20 years.

The following examples illustrate the invention and are not intended to limit the same. Those skilled in the art will recognize, or be able to ascertain through routine experimentation, numerous equivalents to the specific substances and procedures described herein. Such equivalents are considered to be within the scope of the present invention.

The following examples are provided for illustrative purposes only and are not intended to limit the invention.

EXAMPLES

Example 1

Synthesis of Nucleic Acids Oligonucleotides

Oligonucleotides were synthesized on an automated DNA synthesizer using standard phosphoramidite chemistry with oxidation using iodine. b-Cyanoethyldiisopropyl phosphoramidites were purchased from Applied Biosystems (Foster City, Calif.). For phosphorothioate oligonucleotides, the standard oxidation bottle was replaced by a 0.2 M solution of 3H-1,2-benzodithiole-3-one-1,1-dioxide in acetonitrile for the stepwise thiation of the phosphite linkages. The thiation cycle wait step was increased to 68 seconds and was followed by the capping step.

The 2'-fluoro phosphorothioate oligonucleotides of the invention were synthesized using 5'-dimethoxytrityl-3'-phosphoramidites and prepared as disclosed in U.S. patent application Ser. No. 463,358, filed Jan. 11, 1990, and Ser. No. 566,977, filed Aug. 13, 1990, which are assigned to the same assignee as the instant application and which are incorporated by reference herein. The 2'-fluoro oligonucleotides were prepared using phosphoramidite chemistry and a slight modification of the standard DNA synthesis protocol: deprotection was effected using methanolic ammonia at room temperature.

The 2'-methoxy (2'-O-methyl) oligonucleotides of the invention were synthesized using 2'-methoxy β-cyanoethyldiisopropyl-phosphoramidites (Chemgenes, Needham MA) and the standard cycle for unmodified oligonucleotides, except the wait step after pulse delivery of tetrazole and base is increased to 360 seconds. Other 2'-alkoxy oligonucleotides are synthesized by a modification of this method, using appropriate 2'-modified amidites such as those available from Glen Research, Inc., Sterling, Va. The 3'-base used to start the synthesis was a 2'-deoxyribonucleotide. The 2'-O-propyl oligonucleotides of the invention are prepared by a slight modification of this procedure.

The 2' methoxyethoxy (2'-O—CH$_2$CH$_2$OCH$_3$) oligonucleotides of the invention were synthesized according to the method of Martin, *Helv. Chim. Acta* 1995, 78, 486. For ease of synthesis, the last nucleotide was a deoxynucleotide. All 2'-O—CH$_2$CH$_2$OCH$_3$-cytosines were 5-methyl cytosines, which were synthesized according to the following procedures.

Synthesis of 5-Methyl cytosine monomers:

2,2'-Anhydro[1-(β-D-arabinofuranosyl)-5-methyluridine]

5-Methyluridine (ribosylthymine, commercially available through Yamasa, Choshi, Japan) (72.0 g, 0.279 M), diphenyl-carbonate (90.0 g, 0.420 M) and sodium bicarbonate (2.0 g, 0.024 M) were added to DMF (300 mL). The mixture was heated to reflux, with stirring, allowing the evolved carbon dioxide gas to be released in a controlled manner. After 1 hour, the slightly darkened solution was concentrated under reduced pressure. The resulting syrup was poured into diethylether (2.5 L), with stirring. The product formed a gum. The ether was decanted and the residue was dissolved in a minimum amount of methanol (ca. 400 mL). The solution was poured into fresh ether (2.5 L) to yield a stiff gum. The ether was decanted and the gum was dried in a vacuum oven (60° C. at 1 mm Hg for 24 h) to give a solid which was crushed to a light tan powder (57 g, 85% crude yield). The material was used as is for further reactions.

2'-O-Methoxyethyl-5-methyluridine 2,2'-Anhydro-5-methyluridine (195 g, 0.81 M), tris(2-methoxyethyl)borate (231 g, 0.98 M) and 2-methoxyethanol (1.2 L) were added to a 2 L stainless steel pressure vessel and placed in a pre-heated oil bath at 160° C. After heating for 48 hours at 155–160° C., the vessel was opened and the solution evaporated to dryness and triturated with MeOH (200 mL). The residue was suspended in hot acetone (1 L) . The insoluble salts were filtered, washed with acetone (150 mL) and the filtrate evaporated. The residue (280 g) was dissolved in CH$_3$CN (600 mL) and evaporated. A silica gel column (3 kg) was packed in CH$_2$Cl$_2$/acetone/MeOH (20:5:3) containing 0.5% Et$_3$NH. The residue was dissolved in CH$_2$Cl$_2$ (250 mL) and adsorbed onto silica (150 g) prior to loading onto the column. The product was eluted with the packing solvent to give 160 g (63%) of product.

2'-O-Methoxyethyl-5'-O-dimethoxytrityl-5-methyluridine

2'-O-Methoxyethyl-5-methyluridine (160 g, 0.506 M) was co-evaporated with pyridine (250 mL) and the dried residue dissolved in pyridine (1.3 L). A first aliquot of dimethoxytrityl chloride (94.3 g, 0.278 M) was added and the mixture stirred at room temperature for one hour. A second aliquot of dimethoxytrityl chloride (94.3 g, 0.278 M) was added and the reaction stirred for an additional one hour. Methanol (170 mL) was then added to stop the reaction. HPLC showed the presence of approximately 70% product. The solvent was evaporated and triturated with CH$_3$CN (200 mL). The residue was dissolved in CHCl$_3$ (1.5 L) and extracted with 2×500 mL of saturated NaHCO$_3$ and 2×500 mL of saturated NaCl. The organic phase was dried over Na$_2$SO$_4$, filtered and evaporated. 275 g of residue was obtained. The residue was purified on a 3.5 kg silica gel column, packed and eluted with EtOAc/Hexane/Acetone (5:5:1) containing 0.5% Et$_3$NH. The pure fractions were evaporated to give 164 g of product. Approximately 20 g additional was obtained from the impure fractions to give a total yield of 183 g (57%).

3'-O-Acetyl-2'-O-methoxyethyl-5'-O-dimethoxytrityl-5-methyluridine

2'-O-Methoxyethyl-5'-O-dimethoxytrityl-5-methyluridine (106 g, 0.167 M), DMF/pyridine (750 mL of a 3:1 mixture prepared from 562 mL of DMF and 188 mL of pyridine) and acetic anhydride (24.38 mL, 0.258 M) were combined and stirred at room temperature for 24 hours. The reaction was monitored by tlc by first quenching the tlc sample with the addition of MeOH. Upon completion of the reaction, as judged by tlc, MeOH (50 mL) was added and the mixture evaporated at 35° C. The residue was dissolved in CHCl$_3$ (800 mL) and extracted with 2×200 mL of saturated sodium bicarbonate and 2×200 mL of saturated NaCl. The water layers were back extracted with 200 mL of CHCl$_3$. The combined organics were dried with sodium sulfate and evaporated to give 122 g of residue (approx. 90% product). The residue was purified on a 3.5 kg silica gel column and eluted using EtOAc/Hexane(4:1). Pure product fractions were evaporated to yield 96 g (84%).

3'-O-Acetyl-2'-O-methoxyethyl-5'-O-dimethoxytrityl-5-methyl-4-triazoleuridine

A first solution was prepared by dissolving 3'-O-acetyl2'-O-methoxyethyl-5'-O-dimethoxytrityl-5-methyluridine (96 g, 0.144 M) in CH$_3$CN (700 mL) and set aside. Triethylamine (189 mL, 1.44 M) was added to a solution of triazole (90 g, 1.3 M) in CH$_3$CN (1 L), cooled to −5° C. and stirred for 0.5 h using an overhead stirrer. POCl$_3$ was added dropwise, over a 30 minute period, to the stirred solution maintained at 0–10° C., and the resulting mixture stirred for an additional 2 hours. The first solution was added to the later solution dropwise, over a 45 minute period. The resulting reaction mixture was stored overnight in a cold room. Salts were filtered from the reaction mixture and the solution was evaporated. The residue was dissolved in EtOAc (1 L) and the insoluble solids were removed by filtration. The filtrate was washed with 1×300 mL of NaHCO$_3$ and 2×300 mL of saturated NaCl, dried over sodium sulfate and evaporated. The residue was triturated with EtOAc to give the title compound.

2'-O-Methoxyethyl-5'-O-dimethoxytrityl-5-methylcytidine

A solution of 3'-O-acetyl-2'-O-methoxyethyl-5'-O-dimethoxytrityl-5-methyl-4-triazoleuridine (103 g, 0.141 M) in dioxane (500 mL) and NH$_4$OH (30 mL) was stirred at room temperature for 2 hours. The dioxane solution was evaporated and the residue azeotroped with MeOH (2×200 mL). The residue was dissolved in MeOH (300 mL) and transferred to a 2 liter stainless steel pressure vessel. MeOH (400 mL) saturated with NH$_3$ gas was added and the vessel heated to 100° C. for 2 hours (tlc showed complete conversion). The vessel contents were evaporated to dryness and the residue was dissolved in EtOAc (500 mL) and washed once with saturated NaCl (200 mL). The organics were dried over sodium sulfate and the solvent was evaporated to give 85 g (95%) of the title compound.

N$^4$-Benzoyl-2'-O-methoxyethyl-5'-O-dimethoxytrityl-5-methylcytidine

2'-O-Methoxyethyl-5'-O-dimethoxytrityl-5-methylcytidine (85 g, 0.134 M) was dissolved in DMF (800 mL) and benzoic anhydride (37.2 g, 0.165 M) was added with stirring. After stirring for 3 hours, tlc showed the reaction to be approximately 95% complete. The solvent was evaporated and the residue azeotroped with MeOH (200 mL). The residue was dissolved in CHCl$_3$ (700 mL) and extracted with saturated NaHCO$_3$ (2×300 mL) and saturated NaCl (2×300 mL), dried over MgSO$_4$ and evaporated to give a residue (96 g). The residue was chromatographed on a 1.5 kg silica column using EtOAc/Hexane (1:1) containing 0.5% Et$_3$NH as the eluting solvent. The pure product fractions were evaporated to give 90 g (90%) of the title compound.

N$^4$-Benzoyl-2'-O-methoxyethyl-5'-O-dimethoxytrityl-5-methylcytidine-3'-amidite N$^4$-Benzoyl-2'-O-methoxyethyl-5'-O-dimethoxytrityl-5-methylcytidine (74 g, 0.10 M) was dissolved in CH$_2$Cl$_2$ (1 L). Tetrazole diisopropylamine (7.1 g) and 2-cyanoethoxy-tetra-(isopropyl)phosphite (40.5 mL, 0.123 M) were added with stirring, under a nitrogen atmosphere. The resulting mixture was stirred for 20 hours at room temperature (tlc showed the reaction to be 95% complete). The reaction mixture was extracted with saturated NaHCO$_3$ (1×300 mL) and saturated NaCl (3×300 mL). The aqueous washes were back-extracted with CH$_2$Cl$_2$ (300 mL), and the extracts were combined, dried over MgSO$_4$ and concentrated. The residue obtained was chromatographed on a 1.5 kg silica column using EtOAc\Hexane (3:1) as the eluting solvent. The pure fractions were combined to give 90.6 g (87%) of the title compound.

Purification:

After cleavage from the controlled pore glass column (Applied Biosystems) and deblocking in concentrated ammonium hydroxide at 55° C. for 18 hours, the oligonucleotides were purified by precipitation twice out of 0.5 M NaCl with 2.5 volumes ethanol. Analytical gel electrophoresis was accomplished in 20% acrylamide, 8 M urea, 45 mM Tris-borate buffer, pH 7.0. Oligodeoxynucleotides and their phosphorothioate analogs were judged from electrophoresis to be greater than 80% full length material.

A series of oligonucleotides with sequences designed to hybridize to the published human B7-1 (hB7-1) and murine (mB7-1) mRNA sequences (Freeman et al., J. Immunol., 1989, 143, 2714, and Freeman et al., J. Exp. Med., 1991, 174, 625 respectively). The sequences of and modifications to these oligonucleotides, and the location of each of their target sites on the hB7-1 mRNA, are given in Tables 1 and 2. Similarly, a series of oligonucleotides with sequences designed to hybridize to the human B7-2 (hB7-2) and murine B7-2 (mB7-2) mRNA published sequences (respectively, Azuma et al., Nature, 1993, 366, 76; Chen et al., J. Immunol., 1994, 152, 4929) were synthesized. The sequences of and modifications to these oligonucleotides and the location of each of their target sites on the hB7-2 mRNA are described in Tables 3 and 4. Antisense oligonucleotides targeted to ICAM-1, including ISIS 2302 (SEQ ID NO: 17), have been described in U.S. Pat. No. 5,514,788, which issued May 7, 1996, hereby incorporated by reference. ISIS 1082 (SEQ ID NO: 102) and ISIS 3082 (SEQ ID NO: 101) have been previously described (Stepkowski et al., J. Immunol., 1994, 153, 5336).

Subsequent to their initial cloning, alternative splicing events of B7 transcripts have been reported. The reported alternative splicing for B7-1 is relatively simple, in that it results in messages extended 5' relative to the 5' terminus of the human and murine B7-1 cDNA sequences originally reported (Borriello et al., J. Immunol., 1994, 153, 5038; Inobe et al., J. Immunol., 1996, 157, 588). In order to retain the numbering of the B7-1 sequences found in the references initially reporting B7-1 sequences, positions within these 5' extensions of the initially reported sequences have been given negative numbers (beginning with position -1, the most 3' base of the 5' extension) in Tables 1 and 2. The processing of murine B7-2 transcripts is considerably more complex than that so far reported for B7-1; for example, at least five distinct murine B7-2 mRNAs, and at least two distinct human B7-2 mRNAs, can be produced by alternative splicing events (Borriello et al., J. Immunol., 1995, 155, 5490; Freeman et al., WO 95/03408, published Feb. 2, 1995; see also Jellis et al., Immunogenet., 1995, 42, 85). The nature of these splicing events is such that different 5' exons are used to produce distinct B7-2 mRNAs, each of which has a unique 5' sequence but which share a 3' portion consisting of some or all of the B7-2 sequence initially reported. As a result, positions within the 5' extensions of B7-2 messages cannot be uniquely related to a position within the sequence initially reported. Accordingly, in Table 3, a different set of coordinates (corresponding to those of SEQ ID NO: 1 of WO 95/03408) and, in Table 4, the exon number (as given in Borriello et al., J. Immunol., 1995, 155, 5490) is used to specify the location of targeted sequences which are not included in the initially reported B7-2 sequence. Furthermore, although these 5' extended messages contain potential in-frame start codons upstream from the ones indicated in the initially published sequences, for simplicity's sake, such additional potential start codons are not indicated in the description of target sites in Tables 1–4.

In Tables 1–4, the following abbreviations are used: UTR, untranslated region; ORF, open reading frame; tIR, translation initiation region; tTR, translation termination region; FITC, fluorescein isothiocyanate. Chemical modifications are indicated as follows. Residues having 2' fluoro (2'F), 2'-methoxy (2'MO) or 2'-methoxyethoxy (2'ME) modification are emboldened, with the type of modification being indicated by the respective abbreviations. Unless otherwise indicated, interresidue linkages are phosphodiester linkages; phosphorothioate linkages are indicated by an "S" in the superscript position (e.g., T$^S$A). Target positions are numbered according to Freeman et al., J. Immunol., 1989, 143:2714 (human B7-1 cDNA sequence; Table 1), Freeman et al., J. Exp. Med., 1991, 174, 625 (murine B7-1 cDNA sequence; Table 2), Azuma et al., Nature, 1993, 366:76 (human B7-2 cDNA sequence; Table 3) and Chen et al., J. Immunol., 1994, 152:4929 (murine B7-2 cDNA sequence; Table 4). Nucleotide base codes are as given in 37 C.F.R. § 1. 822(b) (1).

TABLE 1

Sequences of Oligonucleotides Targeted to Human B7-1 mRNA

| ISIS # | Target Position; Site (and/or Description) | Oligonucleotide Sequence (5'->3') and Chemical Modifications | SEQ ID NO: |
|---|---|---|---|
| 13797 | 0053-0072; 5'UTR | $G^sG^sG^sT^sA^sA^sG^sA^sC^sT^sC^sC^sA^sC^sT^sT^sC^sT^sG^sA$ | 22 |
| 13798 | 0132-0151; 5'UTR | $G^sG^sG^sT^sC^sT^sC^sC^sA^sA^sA^sG^sG^sT^sT^sG^sT^sG^sA$ | 23 |
| 13799 | 0138-0157; 5'UTR | $G^sT^sT^sC^sC^sT^sG^sG^sG^sT^sC^sT^sC^sC^sA^sA^sA^sG^sG^sT$ | 24 |
| 13800 | 0158-0177; 5'UTR | $A^sC^sA^sC^sA^sC^sA^sG^sA^sA^sG^sA^sT^sT^sG^sG^sA^sG^sG^sT$ | 25 |
| 13801 | 0193-0212; 5'UTR | $G^sC^sT^sC^sA^sC^sG^sT^sA^sG^sA^sA^sG^sA^sC^sC^sC^sT^sC^sC$ | 26 |
| 13802 | 0217-0236; 5'UTR | $G^sG^sC^sA^sG^sG^sG^sC^sT^sG^sA^sT^sG^sA^sC^sA^sA^sT^sC^sC$ | 27 |
| 13803 | 0226-0245; 5'UTR | $T^sG^sC^sA^sA^sA^sA^sC^sA^sG^sG^sG^sC^sA^sG^sG^sG^sC^sT^sG^sA$ | 28 |
| 13804 | 0246-0265; 5'UTR | $A^sG^sA^sC^sC^sA^sG^sG^sG^sC^sA^sC^sT^sT^sC^sC^sC^sA^sG^sG$ | 29 |
| 13805 | 0320-0339; tIR | $C^sC^sT^sG^sC^sC^sT^sC^sC^sG^sT^sG^sG^sT^sG^sT^sG^sG^sC^sC^sC$ | 30 |
| 13806 | 0380-0399; 5'ORF | $G^sA^sC^sA^sA^sG^sC^sC^sA^sG^sC^sA^sC^sC^sA^sA^sG^sA^sG^sC$ | 31 |
| 13807 | 0450-0469; 5'ORF | $C^sC^sA^sC^sA^sG^sG^sA^sC^sA^sG^sC^sG^sT^sT^sG^sC^sC^sA^sC$ | 32 |
| 13808 | 0568-0587; 5'ORF | $C^sC^sG^sG^sT^sT^sC^sT^sT^sG^sT^sA^sC^sT^sC^sG^sG^sG^sC^sC$ | 33 |
| 13809 | 0634-0653; central ORF | $G^sC^sC^sC^sT^sC^sG^sT^sC^sA^sG^sA^sT^sG^sG^sG^sC^sG^sC^sA$ | 51 |
| 13810 | 0829-0848; central ORF | $C^sC^sA^sA^sC^sC^sA^sG^sG^sA^sG^sA^sG^sG^sT^sG^sA^sG^sG^sC$ | 34 |
| 13811 | 1102-1121; 3'ORF | $G^sG^sC^sA^sA^sA^sG^sC^sA^sG^sT^sA^sG^sG^sT^sC^sA^sG^sG^sC$ | 35 |
| 13812 | 1254-1273; 3'-UTR | $G^sC^sC^sT^sC^sA^sT^sG^sA^sT^sC^sC^sC^sC^sA^sC^sG^sA^sT^sC$ | 36 |
| 13872 | (scrambled #13812) | $A^sG^sT^sC^sC^sT^sA^sC^sT^sA^sC^sC^sA^sG^sC^sC^sG^sC^sC^sT$ | 52 |
| 12361 | 0056-0075; 5'UTR | $T^sC^sA^sG^sG^sG^sT^sA^sA^sG^sA^sC^sT^sC^sC^sA^sC^sT^sT^sC$ | 38 |
| 12348 | 0056-0075; 5'UTR | T C A G G $G^sT^sA^sA^sG^sA^sC^sT^sC^sC$ A C T T C (2'ME) | 38 |
| 12473 | 0056-0075; 5'UTR | $T^sC^sA^sG^sG^sG^sT^sA^sA^sG^sA^sC^sT^sC^sC^sC^sA^sC^sT^sT^sC$ (2'Fl) | 38 |
| 12362 | 0143-0162; 5'UTR | $A^sG^sG^sG^sT^sG^sT^sT^sC^sC^sT^sG^sG^sG^sT^sC^sT^sC^sC^sA$ | 39 |
| 12349 | 0143-0162; 5'UTR | A G G G T $G^sT^sT^sC^sC^sC^sT^sG^sG^sG^sT$ C T C C A (2'ME) | 39 |
| 12474 | 0143-0162; 5'UTR | $A^sG^sG^sG^sT^sG^sT^sT^sC^sC^sT^sG^sG^sG^sT^sC^sT^sC^sC^sA$ (2'Fl) | 39 |
| 12363 | 0315-0334; tIR | $C^sT^sC^sC^sG^sT^sG^sT^sG^sT^sG^sG^sC^sC^sC^sA^sT^sG^sG^sC$ | 40 |
| 12350 | 0315-0334; tIR | C T C C G $T^sG^sT^sG^sT^sG^sT^sG^sG^sG^sC$ C C A T G G C (2'ME) | 40 |
| 12475 | 0315-0334; tIR | $C^sT^sC^sC^sG^sT^sG^sT^sG^sT^sG^sT^sG^sG^sC^sC^sC^sA^sT^sG^sG^sC$ (2'Fl) | 40 |
| 12364 | 0334-0353; 5'ORF | $G^sG^sA^sT^sG^sG^sT^sG^sA^sT^sG^sT^sT^sC^sC^sC^sT^sG^sC^sC$ | 41 |
| 12351 | 0334-0353; 5'ORF | G G A T G $G^sT^sG^sA^sT^sG^sT^sT^sC$ C C T G C C (2'ME) | 41 |
| 12476 | 0334-0353; 5'ORF | $G^sG^sA^sT^sG^sG^sT^sG^sA^sT^sG^sT^sT^sC^sC^sC^sT^sG^sC^sC$ (2'Fl) | 41 |
| 12365 | 0387-0406; 5'ORF | $T^sG^sA^sG^sA^sA^sA^sG^sA^sC^sC^sA^sG^sC^sC^sA^sG^sC^sA^sC$ | 42 |
| 12352 | 0387-0406; 5'ORF | T G A G A $A^sG^sA^sC^sC^sA^sG^sC^sC$ A G C A C (2'ME) | 42 |
| 12477 | 0387-0406; 5'ORF | $T^sG^sA^sG^sA^sA^sA^sG^sA^sC^sC^sA^sG^sC^sC^sA^sG^sC^sA^sC$ (2'Fl) | 42 |
| 12366 | 0621-0640; central ORF | $G^sG^sG^sC^sG^sC^sA^sG^sA^sG^sC^sC^sA^sG^sG^sA^sT^sC^sA^sC$ | 43 |
| 12353 | 0621-0640; central ORF | G G G C G $C^sA^sG^sA^sG^sC^sC^sA^sG$ G A T C A C (2'ME) | 43 |
| 12478 | 0621-0640; central ORF | $G^sG^sG^sC^sG^sC^sA^sG^sA^sG^sC^sC^sA^sG^sG^sA^sT^sC^sA^sC$ (2'Fl) | 43 |
| 12367 | 1042-1061; 3'ORF | $G^sG^sC^sC^sC^sA^sG^sG^sA^sT^sG^sG^sG^sA^sG^sC^sA^sG^sG^sT$ | 44 |
| 12354 | 1042-1061; 3'ORF | G G C C C $A^sG^sG^sA^sT^sG^sG^sG^s$ A G C A G G T (2'ME) | 44 |

TABLE 1-continued

Sequences of Oligonucleotides Targeted to Human B7-1 mRNA

| ISIS # | Target Position; Site (and/or Description) | Oligonucleotide Sequence (5'->3') and Chemical Modifications | SEQ ID NO: |
|---|---|---|---|
| 12479 | 1042-1061; 3'ORF | G$^S$G$^S$C$^S$C$^S$C$^S$A$^S$G$^S$G$^S$A$^S$T$^S$G$^S$G$^S$G$^S$A$^S$G$^S$C$^S$A$^S$G$^S$G$^S$T (2'Fl) | 44 |
| 12368 | 1069-1088; tTR | A$^S$G$^S$G$^S$G$^S$C$^S$G$^S$T$^S$A$^S$C$^S$A$^S$C$^S$T$^S$T$^S$T$^S$C$^S$C$^S$C$^S$T$^S$T$^S$C | 45 |
| 12355 | 1069-1088; tTR | A G G G C G$^S$T$^S$A$^S$C$^S$A$^S$C$^S$T$^S$T$^S$T$^S$T C C C T C (2'ME) | 45 |
| 12480 | 1069-1088; tTR | A$^S$G$^S$G$^S$G$^S$C$^S$G$^S$T$^S$A$^S$C$^S$A$^S$C$^S$T$^S$T$^S$T$^S$C$^S$C$^S$C$^S$T$^S$T$^S$C (2'Fl) | 45 |
| 12369 | 1100-1209; tTR | C$^S$A$^S$G$^S$C$^S$C$^S$C$^S$C$^S$T$^S$T$^S$G$^S$C$^S$T$^S$T$^S$T$^S$C$^S$T$^S$G$^S$C$^S$G$^S$G$^S$A | 46 |
| 12356 | 1100-1209; tTR | C A G C C C$^S$C$^S$T$^S$T$^S$G$^S$C$^S$T$^S$T$^S$T$^S$C$^S$T G C G G A(2'ME) | 46 |
| 12481 | 1100-1209; tTR | C$^S$A$^S$G$^S$C$^S$C$^S$C$^S$C$^S$T$^S$T$^S$G$^S$C$^S$T$^S$T$^S$T$^S$C$^S$T$^S$G$^S$C$^S$G$^S$G$^S$A (2'Fl) | 46 |
| 12370 | 1360-1380; 3'UTR | A$^S$A$^S$G$^S$G$^S$A$^S$G$^S$A$^S$G$^S$G$^S$G$^S$A$^S$T$^S$G$^S$C$^S$C$^S$A$^S$G$^S$C$^S$C$^S$A | 47 |
| 12357 | 1360-1380; 3'UTR | A A G G A G$^S$A$^S$G$^S$G$^S$G$^S$A$^S$T$^S$G$^S$C C A G C C A (2'Fl) | 47 |
| 12482 | 1360-1380; 3'UTR | A$^S$A$^S$G$^S$G$^S$A$^S$G$^S$A$^S$G$^S$G$^S$G$^S$A$^S$T$^S$G$^S$C$^S$C$^S$A$^S$G$^S$C$^S$C$^S$A (2'Fl) | 47 |
| 12914 | (-0038 to -0059; 5'UTR of alternative mRNA) | C$^S$T$^S$G$^S$T$^S$T$^S$A$^S$C$^S$T$^S$T$^S$T$^S$A$^S$C$^S$A$^S$G$^S$A$^S$G$^S$G$^S$G$^S$T$^S$T$^S$T$^S$G (2'MO) | 48 |
| 12915 | (-0035 to -0059; 5'UTR of alternative mRNA) | C$^S$T$^S$T$^S$C$^S$T$^S$G$^S$T$^S$T$^S$A$^S$C$^S$T$^S$T$^S$T$^S$A$^S$C$^S$A$^S$G$^S$A$^S$G$^S$G$^S$G$^S$T$^S$T$^S$T$^S$G (2'MO) | 49 |
| 13498 | (-0038 to -0058; 5'UTR of alternative mRNA) | C$^S$T$^S$G$^S$T$^S$T$^S$A$^S$C$^S$T$^S$T$^S$T$^S$T$^S$A$^S$C$^S$A$^S$G$^S$A$^S$G$^S$G$^S$G$^S$T$^S$T$^S$T (2'ME) | 50 |
| 13499 | (-0038 to -0058; 5'UTR of alternative mRNA) | C T G T T A C T T T A C A G A G G G T T T (2'ME) | 50 |

TABLE 2

Sequences of Oligonucleotides Targeted to Murine B7-1 mRNA

| ISIS # | Target Position; Site | Oligonucleotide Sequence (5'->3') and Chemical Modifications | SEQ ID NO: |
|---|---|---|---|
| 14419 | 0009-0028; 5'UTR | A$^S$G$^S$T$^S$A$^S$A$^S$G$^S$A$^S$G$^S$T$^S$C$^S$T$^S$A$^S$T$^S$T$^S$G$^S$A$^S$G$^S$G$^S$T$^S$A | 53 |
| 14420 | 0041-0060; 5'UTR | G$^S$G$^S$T$^S$T$^S$G$^S$A$^S$G$^S$T$^S$T$^S$T$^S$C$^S$A$^S$C$^S$A$^S$A$^S$C$^S$C$^S$T$^S$G$^S$A | 54 |
| 14421 | 0071-0091; 5'UTR | G$^S$T$^S$C$^S$C$^S$A$^S$C$^S$A$^S$G$^S$A$^S$A$^S$T$^S$G$^S$G$^S$A$^S$A$^S$C$^S$A$^S$G$^S$A$^S$G | 55 |
| 14422 | 0109-0128; 5'UTR | G$^S$G$^S$G$^S$C$^S$A$^S$T$^S$C$^S$C$^S$A$^S$C$^S$C$^S$C$^S$G$^S$G$^S$C$^S$A$^S$G$^S$A$^S$T$^S$G$^S$C | 56 |
| 14423 | 0114-0133; 5'UTR | T$^S$G$^S$G$^S$A$^S$T$^S$G$^S$G$^S$C$^S$A$^S$T$^S$C$^S$C$^S$A$^S$C$^S$C$^S$C$^S$G$^S$G$^S$C$^S$A | 57 |
| 14424 | 0168-0187; 5'UTR | A$^S$G$^S$G$^S$C$^S$A$^S$C$^S$C$^S$T$^S$C$^S$C$^S$T$^S$A$^S$G$^S$G$^S$C$^S$T$^S$C$^S$A$^S$C$^S$A | 58 |
| 14425 | 0181-0200; 5'UTR | G$^S$C$^S$C$^S$A$^S$A$^S$T$^S$G$^S$G$^S$A$^S$G$^S$C$^S$T$^S$T$^S$A$^S$G$^S$G$^S$C$^S$A$^S$C$^S$C | 59 |
| 14426 | 0208-0217; 5'UTR | C$^S$A$^S$T$^S$G$^S$A$^S$T$^S$G$^S$G$^S$G$^S$G$^S$A$^S$A$^S$A$^S$G$^S$C$^S$C$^S$A$^S$G$^S$G$^S$A | 60 |
| 14427 | 0242-0261; tIR | A$^S$A$^S$T$^S$T$^S$G$^S$C$^S$A$^S$A$^S$G$^S$C$^S$C$^S$A$^S$T$^S$A$^S$G$^S$C$^S$T$^S$T$^S$C$^S$A | 61 |
| 14428 | 0393-0412; 5'ORF | C$^S$G$^S$G$^S$C$^S$A$^S$A$^S$G$^S$G$^S$C$^S$A$^S$G$^S$C$^S$A$^S$A$^S$T$^S$A$^S$C$^S$C$^S$T$^S$T | 62 |
| 14909 | 0478-0497; 5'ORF | C$^S$C$^S$C$^S$A$^S$G$^S$C$^S$A$^S$A$^S$T$^S$G$^S$A$^S$C$^S$A$^S$G$^S$A$^S$C$^S$A$^S$G$^S$C$^S$A | 63 |
| 14910 | 0569-0588; central ORF | G$^S$G$^S$T$^S$C$^S$T$^S$G$^S$A$^S$A$^S$A$^S$G$^S$G$^S$A$^S$C$^S$C$^S$A$^S$G$^S$G$^S$C$^S$C$^S$C | 64 |
| 14911 | 0745-0764; central ORF | T$^S$G$^S$G$^S$G$^S$A$^S$A$^S$A$^S$C$^S$C$^S$C$^S$C$^S$C$^S$G$^S$G$^S$A$^S$A$^S$G$^S$C$^S$A$^S$A | 65 |
| 14912 | 0750-0769; central ORF | G$^S$G$^S$C$^S$T$^S$T$^S$T$^S$G$^S$G$^S$G$^S$A$^S$A$^S$A$^S$C$^S$C$^S$C$^S$C$^S$C$^S$G$^S$G$^S$A | 66 |
| 14913 | 0825-0844; 3'ORF | T$^S$C$^S$A$^S$G$^S$A$^S$T$^S$T$^S$C$^S$A$^S$G$^S$G$^S$A$^S$T$^S$C$^S$C$^S$T$^S$G$^S$G$^S$G$^S$A | 67 |
| 14914 | 0932-0951; 3'ORF | C$^S$C$^S$C$^S$A$^S$G$^S$G$^S$T$^S$G$^S$A$^S$A$^S$G$^S$T$^S$C$^S$C$^S$T$^S$C$^S$T$^S$G$^S$A$^S$C | 68 |

TABLE 2-continued

Sequences of Oligonucleotides Targeted to Murine B7-1 mRNA

| ISIS # | Target Position; Site | Oligonucleotide Sequence (5'->3') and Chemical Modifications | SEQ ID NO: |
|---|---|---|---|
| 14915 | 1001-1020; 3'ORF | $C^ST^SG^SC^SG^SC^SC^SG^SA^SA^ST^SC^SC^ST^SG^SC^SC^SC^SC^SA$ | 69 |
| 14916 | 1125-1144; tTR | $C^SA^SG^SG^SC^SC^SC^SG^SA^SA^SG^SG^ST^SA^SA^SG^SG^SC^ST^SG$ | 70 |
| 14917 | 1229-1248; 3'UTR | $T^SC^SA^SG^SC^ST^SA^SG^SC^SA^SC^SG^SG^ST^SG^SC^ST^SG^SA^SA$ | 71 |
| 14918 | 1329-1348; 3'UTR | $G^SG^SC^SC^SC^SA^SG^SC^SA^SA^SA^SC^ST^ST^SG^SC^SC^SC^SG^ST$ | 72 |
| 14919 | 1377-1393; 3'UTR | $C^SC^SA^SC^SC^SA^SC^SA^SG^ST^SG^SG^SG^SC^ST^SC^SA^SG^SC^SC$ | 73 |
| 12912 | -0067 to -0049; 5'UTR | $G^SG^SC^SC^SA^ST^SG^SA^SG^SG^SG^SC^SA^SA^ST^SC^ST^SA^SA$ (2'MO) | 74 |
| 12913 | -0067 to -0047; 5'UTR | $G^ST^SG^SG^SC^SC^SA^ST^SG^SA^SG^SG^SG^SC^SA^SA^ST^SC^ST^SA^SA$ (2'MO) | 75 |
| 13496 | -0067 to -0047; 5'UTR | $G^ST^SG^SG^SC^SC^SA^ST^SG^SA^SG^SG^SG^SC^SA^SA^ST^SC^ST^SA^SA$ (2'ME) | 75 |
| 13497 | -0067 to -0047; 5'UTR | GTGGCCATGAGGGCAATCTAA (2'MO) | 75 |

TABLE 3

Sequences of Oligonucleotides Targeted to Human B7-2 mRNA

| ISIS # | Target Position*; Site** | Oligonucleotide Sequence (5'->3') | SEQ ID NO: |
|---|---|---|---|
| 9133 | 1367-1386; 3'-UTR | $T^ST^SC^SC^SA^SG^SG^ST^SC^SA^ST^SG^SA^SG^SC^SC^SA^ST^ST^SA$ | 3 |
| 10715 | scrambled control of #9133 | $G^SA^ST^ST^SA^SA^SC^SA^ST^ST^ST^SG^SG^SC^SG^SC^SC^SA$ | 76 |
| 9134 | 1333-1352; 3'-UTR | $C^SA^ST^SA^SA^SG^SG^ST^SG^ST^SG^SC^ST^SC^ST^SG^SA^SA^SG^ST^SG$ | 4 |
| 9135 | 1211-1230; 3'-UTR | $T^ST^SA^SC^ST^SC^SA^ST^SG^SG^ST^SA^SA^ST^SG^ST^SC^ST^ST^ST^S$ | 5 |
| 9136 | 1101-1120; tTR | $A^ST^ST^SA^SA^SA^SA^SC^SA^ST^SG^ST^SA^ST^SC^SA^SC^ST^ST^S$ | 6 |
| 10716 | (scrambled #9136) | $A^SA^SA^SG^ST^ST^SA^SC^SA^SA^SC^SA^ST^ST^SA^ST^SA^ST^SC^ST$ | 77 |
| 9137 | 0054-0074; 5'-UTR | $G^SG^SA^SA^SC^SA^SC^SA^SG^SA^SA^SG^SC^SA^SA^SG^SG^ST^SG^SG^ST$ | 7 |
| 9138 | 0001-0020; 5'-UTR | $C^SC^SG^ST^SA^SC^SC^ST^SC^SC^ST^SA^SA^SG^SC^ST^SC^SC^ST$ | 8 |
| 9139 | 0133-0152; tIR | $C^SC^SA^ST^SA^SG^ST^SG^SC^ST^SG^ST^SC^SA^SC^SA^SA^SA^ST$ | 9 |
| 10877 | (scrambled #9139) | $A^SG^ST^SG^SC^SG^SA^ST^ST^SC^ST^SC^SA^SA^SA^SC^SC^ST^SA^SC$ | 78 |
| 10367 | 0073-0092; 5'-UTR | $G^SC^SA^SC^SA^SG^SC^SA^SG^SC^SA^ST^ST^SC^SC^SC^SA^SA^SG^SG$ | 10 |
| 10368 | 0240-0259; 5'-ORF | $T^ST^SG^SC^SA^SA^SA^ST^ST^SG^SG^SC^SA^ST^SG^SG^SC^SA^SG^SG$ | 11 |
| 10369 | 1122-1141; 3'-UTR | $T^SG^SG^ST^SA^ST^SG^SG^SG^SC^ST^ST^ST^SA^SC^ST^SC^ST^ST^ST$ | 12 |
| 10370 | 1171-1190; 3'-UTR | $A^SA^SA^SA^SG^SG^ST^ST^SG^SC^SC^SC^SA^SG^SG^SA^SA^SC^SG^SG$ | 13 |
| 10371 | 1233-1252; 3'-UTR | $G^SG^SG^SA^SG^ST^SC^ST^ST^SG^SG^SA^SG^SC^SC^SC^SC^SC^ST^ST$ | 14 |
| 10372 | 1353-1372; 3'-UTR | $C^SC^SA^ST^ST^SA^SA^SG^SC^ST^SG^SG^SG^SC^ST^ST^SG^SG^SC^SC$ | 15 |
| 11149 | 0019-0034; 5'-UTR | $T^SA^ST^ST^ST^SG^SC^SG^SA^SG^SC^ST^SC^SC^SC^SC$ | 79 |
| 11151 | 0020-0034; 5'-UTR | $T^SA^ST^ST^SG^SC^SG^SA^SG^SC^ST^SC^SC^SC$ | 80 |
| 11150 | 0021-0034; 5'-UTR | $T^SA^ST^ST^SG^SC^SG^SA^SG^SC^ST^SC^SC$ | 81 |
| 10373 | 0011-0030; 5'-UTR | $T^SG^SC^SG^SA^SG^SC^ST^SC^SC^SC^SC^SG^ST^SA^SC^SC^ST^SC^SC$ | 16 |
| 10721 | (scrambled #10373) | $C^SG^SA^SC^SA^SG^SC^ST^SC^SC^ST^SG^SC^SG^SC^ST^SC^SC^ST^SC$ | 82 |
| 10729 | (5'FITC #10373) | $T^SG^SC^SG^SA^SG^SC^ST^SC^SC^SC^SC^SG^ST^SA^SC^SC^ST^SC^SC$ | 16 |
| 10782 | (5'cholesterol #10373) | $T^SG^SC^SG^SA^SG^SC^ST^SC^SC^SC^SC^SG^ST^SA^SC^SC^ST^SC^SC$ | 16 |

TABLE 3-continued

Sequences of Oligonucleotides Targeted to Human B7-2 mRNA

| ISIS # | Target Position*; Site** | Oligonucleotide Sequence (5'->3') | SEQ ID NO: |
|---|---|---|---|
| # 10373 Deletion Derivatives: | | | |
| 10373 | 0011-0030; 5'-UTR | T$^s$G$^s$C$^s$G$^s$A$^s$G$^s$C$^s$T$^s$C$^s$C$^s$C$^s$C$^s$G$^s$T$^s$A$^s$C$^s$C$^s$T$^s$C$^s$C | 16 |
| 10888 | 0011-0026; 5'-UTR | A$^s$G$^s$C$^s$T$^s$C$^s$C$^s$C$^s$C$^s$G$^s$T$^s$A$^s$C$^s$C$^s$T$^s$C$^s$C | 83 |
| 10889 | 0015-0030; 5'-UTR | T$^s$G$^s$C$^s$G$^s$A$^s$G$^s$C$^s$T$^s$C$^s$C$^s$C$^s$C$^s$G$^s$T$^s$A$^s$C | 84 |
| 10991 | 0015-0024; 5'-UTR | C$^s$T$^s$C$^s$C$^s$C$^s$C$^s$G$^s$T$^s$A$^s$C | 85 |
| 10992 | 0015-0025; 5'-UTR | G$^s$C$^s$T$^s$C$^s$C$^s$C$^s$C$^s$G$^s$T$^s$A$^s$C | 86 |
| 10993 | 0015-0026; 5'-UTR | A$^s$G$^s$C$^s$T$^s$C$^s$C$^s$C$^s$C$^s$G$^s$T$^s$A$^s$C | 87 |
| 10994 | 0015-0027; 5'-UTR | G$^s$A$^s$G$^s$C$^s$T$^s$C$^s$C$^s$C$^s$C$^s$G$^s$T$^s$A$^s$C | 88 |
| 10995 | 0015-0028; 5'-UTR | C$^s$G$^s$A$^s$G$^s$C$^s$T$^s$C$^s$C$^s$C$^s$C$^s$G$^s$T$^s$A$^s$C | 89 |
| 10996 | 0015-0029; 5'-UTR | G$^s$C$^s$G$^s$A$^s$G$^s$C$^s$T$^s$C$^s$C$^s$C$^s$C$^s$G$^s$T$^s$A$^s$C | 90 |
| 11232 | 0017-0029; 5'UTR | G$^s$C$^s$G$^s$A$^s$G$^s$C$^s$T$^s$C$^s$C$^s$C$^s$C$^s$G$^s$T | 91 |
| #10996 Derivatives: | | | |
| 10996 | 0015-0029; 5'UTR | G$^s$C$^s$G$^s$A$^s$G$^s$C$^s$T$^s$C$^s$C$^s$C$^s$C$^s$G$^s$T$^s$A$^s$C | 90 |
| 11806 | (scrambled #10996) | G$^s$C$^s$C$^s$G$^s$C$^s$C$^s$G$^s$C$^s$C$^s$A$^s$A$^s$G$^s$T$^s$C$^s$T | 92 |
| 11539 | (fully 2'MO #10996) | G$^s$C$^s$G$^s$A$^s$G$^s$C$^s$T$^s$C$^s$C$^s$C$^s$C$^s$G$^s$T$^s$A$^s$C (2' MO) | 90 |
| 11540 | (control for #11539) | G$^s$C$^s$C$^s$G$^s$C$^s$C$^s$G$^s$C$^s$C$^s$A$^s$A$^s$G$^s$T$^s$C$^s$T (2' MO) | 92 |
| 11541 | (#10996 7-base "gapmer") | G$^s$C$^s$G$^s$A$^s$G$^s$C$^s$T$^s$C$^s$C$^s$C$^s$C$^s$G$^s$T$^s$A$^s$C (2' MO) | 90 |
| 11542 | (control for #11541) | G$^s$C$^s$C$^s$G$^s$C$^s$C$^s$G$^s$C$^s$C$^s$A$^s$A$^s$G$^s$T$^s$C$^s$T (2' MO) | 92 |
| 11543 | (#10996 9-base "gapmer") | G$^s$C$^s$G$^s$A$^s$G$^s$C$^s$T$^s$C$^s$C$^s$C$^s$C$^s$G$^s$T$^s$A$^s$C (2' MO) | 90 |
| 11544 | (control for #11543) | G$^s$C$^s$C$^s$G$^s$C$^s$C$^s$G$^s$C$^s$C$^s$A$^s$A$^s$G$^s$T$^s$C$^s$T (2' MO) | 92 |
| 11545 | (#10996 5' "wingmer") | G$^s$C$^s$G$^s$A$^s$G$^s$C$^s$T$^s$C$^s$C$^s$C$^s$C$^s$G$^s$T$^s$A$^s$C (2' MO) | 90 |
| 11546 | (control for #11545) | G$^s$C$^s$C$^s$G$^s$C$^s$C$^s$G$^s$C$^s$C$^s$A$^s$A$^s$G$^s$T$^s$C$^s$T (2' MO) | 92 |
| 11547 | (#10996 3' "wingmer") | G$^s$C$^s$G$^s$A$^s$G$^s$C$^s$T$^s$C$^s$C$^s$C$^s$C$^s$G$^s$T$^s$A$^s$C (2' MO) | 90 |
| 11548 | (control for #11547) | G$^s$C$^s$C$^s$G$^s$C$^s$C$^s$G$^s$C$^s$C$^s$A$^s$A$^s$G$^s$T$^s$C$^s$T (2' MO) | 92 |
| 12496 | ((2'-5')A$_4$#10996) | G C G A G C T C C C C G T A C | 90 |
| 13107 | ((2'-5')A$_4$#10996) | G$^s$C$^s$G$^s$A$^s$G$^s$C$^s$T$^s$C$^s$C$^s$C$^s$C$^s$G$^s$T$^s$A$^s$C | 90 |
| 12492 | ((2'-5')A$_4$#10996) | G$^s$C$^s$G$^s$A$^s$G$^s$C$^s$T$^s$C$^s$C$^s$C$^s$C$^s$G$^s$T$^s$A$^s$C (2' MO) | 90 |
| 12495 | ((2'-5')A$_4$#10996) | G$^s$C$^s$G$^s$A$^s$G$^s$C$^s$T$^s$C$^s$C$^s$C$^s$C$^s$G$^s$T$^s$A$^s$C (2' MO) | 90 |
| 12887 | (1-24 of SEQ ID NO: 1 of WO 95/03408; alternative mRNA) | G$^s$A$^s$G$^s$A$^s$A$^s$G$^s$C$^s$A$^s$A$^s$A$^s$G$^s$C$^s$T$^s$T$^s$T$^s$C$^s$A$^s$C$^s$C$^s$C$^s$-$^s$T$^s$G$^s$T$^s$G (2' MO) | 93 |
| 12888 | (1-22 of SEQ ID NO: 1 of WO 95/03408; alternative mRNA) | G$^s$A$^s$A$^s$G$^s$C$^s$A$^s$A$^s$A$^s$G$^s$C$^s$T$^s$T$^s$T$^s$C$^s$A$^s$C$^s$C$^s$C$^s$T$^s$G$^s$T$^s$G (2' MO) | 94 |
| 12889 | (1-19 of SEQ ID NO: 1 of WO 95/03408; alternative mRNA) | G$^s$C$^s$A$^s$A$^s$A$^s$G$^s$C$^s$T$^s$T$^s$T$^s$C$^s$A$^s$C$^s$C$^s$C$^s$T$^s$G$^s$T$^s$G (2' MO) | 95 |
| 12890 | 0001-0024 | C$^s$T$^s$C$^s$C$^s$C$^s$C$^s$G$^s$T$^s$A$^s$C$^s$C$^s$T$^s$C$^s$C$^s$T$^s$A$^s$A$^s$G$^s$G$^s$C$^s$-$^s$T$^s$C$^s$C$^s$T (2' MO) | 96 |

TABLE 3-continued

Sequences of Oligonucleotides Targeted to Human B7-2 mRNA

| ISIS # | Target Position*; Site** | Oligonucleotide Sequence (5'->3') | SEQ ID NO: |
|---|---|---|---|
| 12891 | 0001-0022 | $C^sC^sC^sC^sG^sT^sA^sC^sC^sT^sC^sC^sT^sA^sA^sG^sG^sC^sT^sC^sC^sT$ (2' MO) | 97 |
| 12892 | 0001-0020 | $C^sC^sG^sT^sA^sC^sC^sT^sC^sC^sT^sA^sA^sG^sG^sC^sT^sC^sC$ (2' MO) | 98 |

TABLE 4

Sequences of Oligonucleotides Targeted to Murine B7-2 mRNA

| ISIS # | Target Position; Site | Oligonucleotide Sequence (5'->3') | SEQ ID NO: |
|---|---|---|---|
| 11347 | 1094-1113; 3'UTR | $A^sG^sA^sA^sT^sT^sC^sC^sA^sA^sT^sC^sA^sG^sC^sT^sG^sA^sG^sA$ | 121 |
| 11348 | 1062-1081; 3'UTR | $T^sC^sT^sG^sA^sG^sA^sA^sA^sC^sT^sC^sT^sG^sC^sA^sC^sT^sT^sC$ | 122 |
| 11349 | 1012-1031; 3'UTR | $T^sC^sC^sT^sC^sA^sG^sG^sC^sT^sC^sT^sC^sA^sC^sT^sG^sC^sC^sT$ | 123 |
| 11350 | 0019-1138; 5'UTR | $G^sG^sT^sT^sG^sT^sT^sC^sA^sA^sG^sT^sC^sC^sG^sT^sG^sC^sT^sG$ | 124 |
| 11351 | 0037-0056; 5'UTR | $A^sC^sA^sC^sG^sT^sC^sT^sA^sC^sA^sG^sG^sA^sG^sT^sC^sT^sG^sG$ | 103 |
| 11352 | 0089-0108; tIR | $C^sA^sA^sG^sC^sC^sC^sA^sT^sG^sG^sT^sG^sC^sA^sT^sC^sT^sG^sG$ | 104 |
| 11353 | 0073-0092; tIR | $C^sT^sG^sG^sG^sG^sT^sC^sC^sA^sT^sC^sG^sT^sG^sG^sG^sT^sG^sC$ | 105 |
| 11354 | 0007-0026; 5'UTR | $C^sC^sG^sT^sG^sC^sT^sG^sC^sC^sT^sA^sC^sA^sG^sG^sA^sG^sC^sC$ | 106 |
| 11695 | 0058-0077; 5'UTR | $G^sG^sT^sG^sC^sT^sT^sC^sC^sG^sT^sA^sA^sG^sT^sT^sC^sT^sG^sG$ | 107 |
| 11696 | 0096-0117; tIR | $G^sG^sA^sT^sT^sG^sC^sC^sA^sA^sG^sC^sC^sC^sA^sT^sG^sG^sT^sG$ | 108 |
| 11866 | (scrambled #11696) | $C^sT^sA^sA^sG^sT^sA^sG^sT^sG^sC^sT^sA^sG^sC^sC^sG^sG^sG^sA$ | 109 |
| 11697 | 0148-0167; 5'ORF | $T^sG^sC^sG^sT^sC^sT^sC^sC^sA^sC^sG^sG^sA^sA^sA^sC^sA^sG^sC$ | 110 |
| 11698 | 0319-0338; 5'ORF | $G^sT^sG^sC^sG^sG^sC^sC^sC^sA^sG^sG^sT^sA^sC^sT^sT^sG^sG^sC$ | 111 |
| 11699 | 0832-0851; 3'ORF | $A^sC^sA^sG^sG^sA^sG^sG^sA^sG^sG^sG^sC^sC^sA^sC^sA^sG^sT$ | 112 |
| 11700 | 0753-0772; 3'ORF | $T^sG^sA^sG^sA^sG^sG^sT^sT^sT^sG^sG^sA^sG^sG^sA^sA^sA^sT^sC$ | 113 |
| 11701 | 0938-0957; 3'ORF | $G^sA^sT^sA^sG^sT^sC^sT^sC^sT^sC^sT^sG^sT^sC^sA^sG^sC^sG^sT$ | 114 |
| 11702 | 0890-0909; 3'ORF | $G^sT^sT^sG^sC^sT^sG^sG^sG^sC^sC^sT^sG^sC^sT^sA^sG^sG^sC^sT$ | 115 | cDNA clones:

A cDNA encoding the sequence for human B7-1 was isolated by using the reverse transcription/polymerase chain reaction (RT-PCR). Poly A+ RNA from Daudi cells (ATCC accession No. CCL 213) was reverse transcribed using oligo-dT primer under standard conditions. Following a 30 minute reaction at 42° C. and heat inactivation, the reaction mixture (20 μL) was brought to 100 μL with water. A 10 μL aliquot from the RT reaction was then amplified in a 50 μL PCR reaction using the 5' primer, 5'-GAT-CAG-GGT-ACC-CCA-AAG-AAA-AAG-TGA-TTT-GTC-ATT-GC-3' (sense, SEQ ID NO: 20), and the 3' primer, 5'-GAT-AGC-CTC-GAG-GAT-AAT-GAA-TTG-GCT-GAC-AAG-AC-3' (antisense, SEQ ID NO: 21).

The primers included unique restriction sites for subcloning of the PCR product into the vector pcDNA-3 (Invitrogen, San Diego, Calif.). The 5' primer was designed to have identity with bases 1 to 26 of the published human B7-1 sequence (Freeman et al., J. Immunol., 1989, 143, 2714; positions 13–38 of the primer) and includes a Kpn I restriction site (positions 7–12 of the primer) for use in cloning. The 3' primer was designed to be complementary to bases 1450 to 1471 of the published sequence for B7-1 (positions 14–35 of the primer) and includes a Xho I restriction site (positions 7-12 of the primer). Following PCR, the reaction was extracted with phenol and precipitated using ethanol. The product was digested with the appropriate restriction enzymes and the full-length fragment purified by agarose gel and ligated into the vector pcDNA-3 (Invitrogen, San Diego, Calif.) prepared by digesting with the same enzymes. The resultant construct, pcB7-1, was confirmed by restriction mapping and DNA sequence analysis using standard procedures. A mouse B7-1 clone, pcmB7-1, was isolated in a similar manner by RT-PCR of RNA isolated from a murine B-lymphocyte cell line, 70Z3.

A cDNA encoding the sequence for human B7-2, position 1 to 1391, was also isolated by RT-PCR. Poly A+ RNA from Daudi cells (ATCC accession No. CCL 213) was reverse transcribed using oligo-dT primer under standard conditions. Following a 30 minute reaction at 42° C. and heat inactivation, the reaction mixture (20 μL) was brought to 100 μL with water. A 10 μL aliquot from the RT reaction was then amplified in a 50 μL PCR reaction using the 5' primer, 5'-GAT-CAG-GGT-ACC-AGG-AGC-CTT-AGG-AGG-TAC-GG-3' (sense, SEQ ID NO: 1), and the 3' primer, 5'-GAT-AGC-CTC-GAG-TTA-TTT-CCA-GGT-CAT-GAG-CCA-3' (antisense, SEQ ID NO: 2).

The 5' primer was designed to have identity with bases 1–20 of the published B7-2 sequence (Azuma et al., *Nature*, 1993, 366, 76 and Genbank Accession No. L25259; positions 13–32 of the primer) and includes a Kpn I site (positions 7–12 of the primer) for use in cloning. The 3' primer was designed to have complementarity to bases 1370–1391 of the published sequence for B7-2 (positions 13–33 of the primer) and includes an Xho I restriction site (positions 7–12 of the primer). Following PCR, the reaction was extracted with phenol and precipitated using ethanol. The product was digested with Xho I and Kpn I, and the full-length fragment purified by agarose gel and ligated into the vector pcDNA-3 (Invitrogen, San Diego, Calif.) prepared by digesting with the same enzymes. The resultant construct, pcB7-2, was confirmed by restriction mapping and DNA sequence analysis using standard procedures.

A mouse B7-2 clone, pcmB7-2, was isolated in a similar manner by RT-PCR of RNA isolated from P388D1 cells using the 5' primer, 5'-GAT-CAG-GGT-ACC-AAG-AGT-GGC-TCC-TGT-AGG-CA (sense, SEQ ID NO: 99), and the 3' primer, 5'-GAT-AGC-CTC-GAG-GTA-GAA-TTC-CAA-TCA-GCT-GA (antisense, SEQ ID NO: 100).

The 5' primer has identity with bases 1–20, whereas the 3' primer is complementary to bases 1096–1115, of the published murine B7-2 sequence (Chen et al., *J. Immun.*, 1994, 152, 4929). Both primers incorporate the respective restriction enzyme sites found in the other 5' and 3' primers used to prepare cDNA clones. The RT-PCR product was restricted with Xho I and Kpn I and ligated into pcDNA-3 (Invitrogen, San Diego, Calif.).

Other cDNA clones, corresponding to mRNAs resulting from alternative splicing events, are cloned in like fashion, using primers containing the appropriate restriction sites and having identity with (5' primers), or complementarity to (3' primers), the selected B7 mRNA.

Example 2

Modulation of hB7-1 Expression by Oligonucleotides

The ability of oligonucleotides to inhibit B7-1 expression was evaluated by measuring the cell surface expression of B7-1 in transfected COS-7 cells by flow cytometry.
Methods:

A T-175 flask was seeded at 75% confluency with COS-7 cells (ATCC accession No. CRL 1651). The plasmid pcB7-1 was introduced into cells by standard calcium phosphate transfection. Following a 4 hour transfection, the cells were trypsinized and seeded in 12-well dishes at 80% confluency. The cells were allowed to adhere to the plastic for 1 hour and were then washed with phosphate-buffered saline (PBS). OptiMEM™ (GIBCO-BRL, Gaithersburg, Md.) medium was added along with 15 μg/mL of Lipofectin™ (GIBCO-BRL, Gaithersburg, Md.) and oligonucleotide at the indicated concentrations. After four additional hours, the cells were washed with phosphate buffered saline (PBS) and incubated with fresh oligonucleotide at the same concentration in DMEM (Dulbecco et al., *Virol.*, 1959, 8, 396; Smith et al., *Virol.*, 1960, 12, 185) with 10% fetal calf sera (FCS).

In order to monitor the effects of oligonucleotides on cell surface expression of B7-1, treated COS-7 cells were harvested by brief trypsinization 24–48 hours after oligonucleotide treatment. The cells were washed with PBS, then resuspended in 100 μL of staining buffer (PBS, 0.2% BSA, 0.1% azide) with 5 μL conjugated anti-B7-1-antibody (i.e., anti-hCD80-FITC, Ancell, Bayport, Minn; FITC: fluorescein isothiocyanate). The cells were stained for 30 minutes at 4° C., washed with PBS, resuspended in 300 μL containing 0.5% paraformaldehyde. Cells were harvested and the fluorescence profiles were determined using a flow cytometer.
Results:

The oligonucleotides shown in Table 1 were evaluated, in COS-7 cells transiently expressing B7-1 cDNA, for their ability to inhibit B7-1 expression. The results (FIG. 1) identified ISIS 13805, targeted to the translation initiation codon region, and ISIS 13812, targeted to the 3' untranslated region (UTR), as the most active oligonucleotides with greater than 50% inhibition of B7-1 expression. These oligonucleotides are thus highly preferred. ISIS 13799 (targeted to the 5' untranslated region), ISIS 13802 (targeted to the 5' untranslated region), ISIS 13806 and 13807 (both targeted to the 5' region of the ORF), and ISIS 13810 (targeted to the central portion of the ORF) demonstrated 35% to 50% inhibition of B7-1 expression. These sequences are therefore also preferred.

Figure 2:
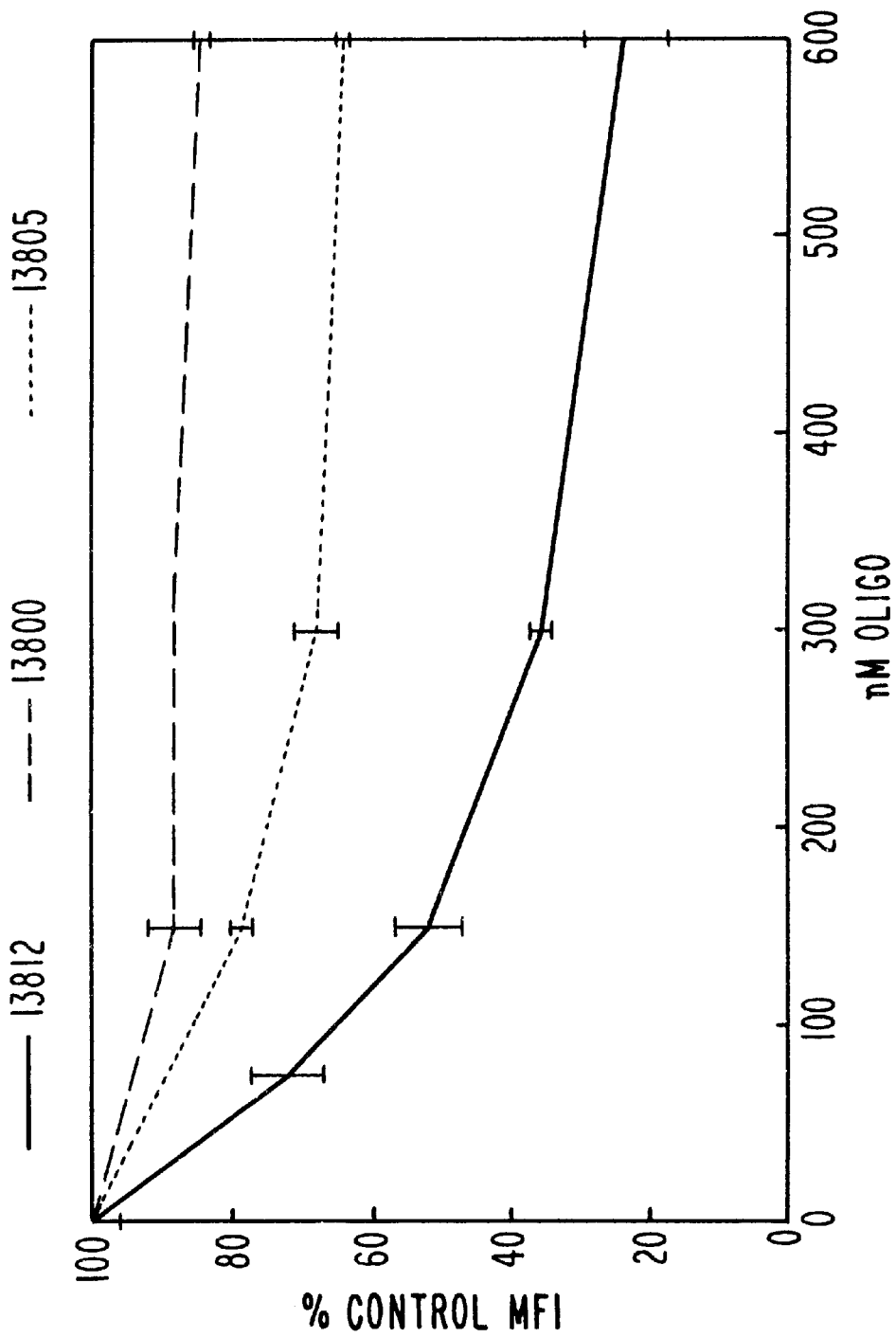
FIG. 2 is a dose-response curve showing the inhibitory effect of oligonucleotides on cell surface expression of B7-1 protein. Solid line, ISIS 13812; dashed line, ISIS 13800; dotted line, ISIS 13805.

Oligonucleotide ISIS 13800, which showed essentially no inhibition of B7-1 expression in the flow cytometry assay, and ISIS Nos. 13805 and 13812 were then evaluated for their ability to inhibit cell surface expression of B7-1 at various concentrations of oligonucleotide. The results of these assays are shown in FIG. 2. ISIS 13812 was a superior inhibitor of B7-1 expression with an $IC_{50}$ of approximately 150 nM. ISIS 13800, targeted to the 5' UTR, was essentially inactive.

Example 3

Modulation of hB7-2 Protein by Oligonucleotides

Figure 3:
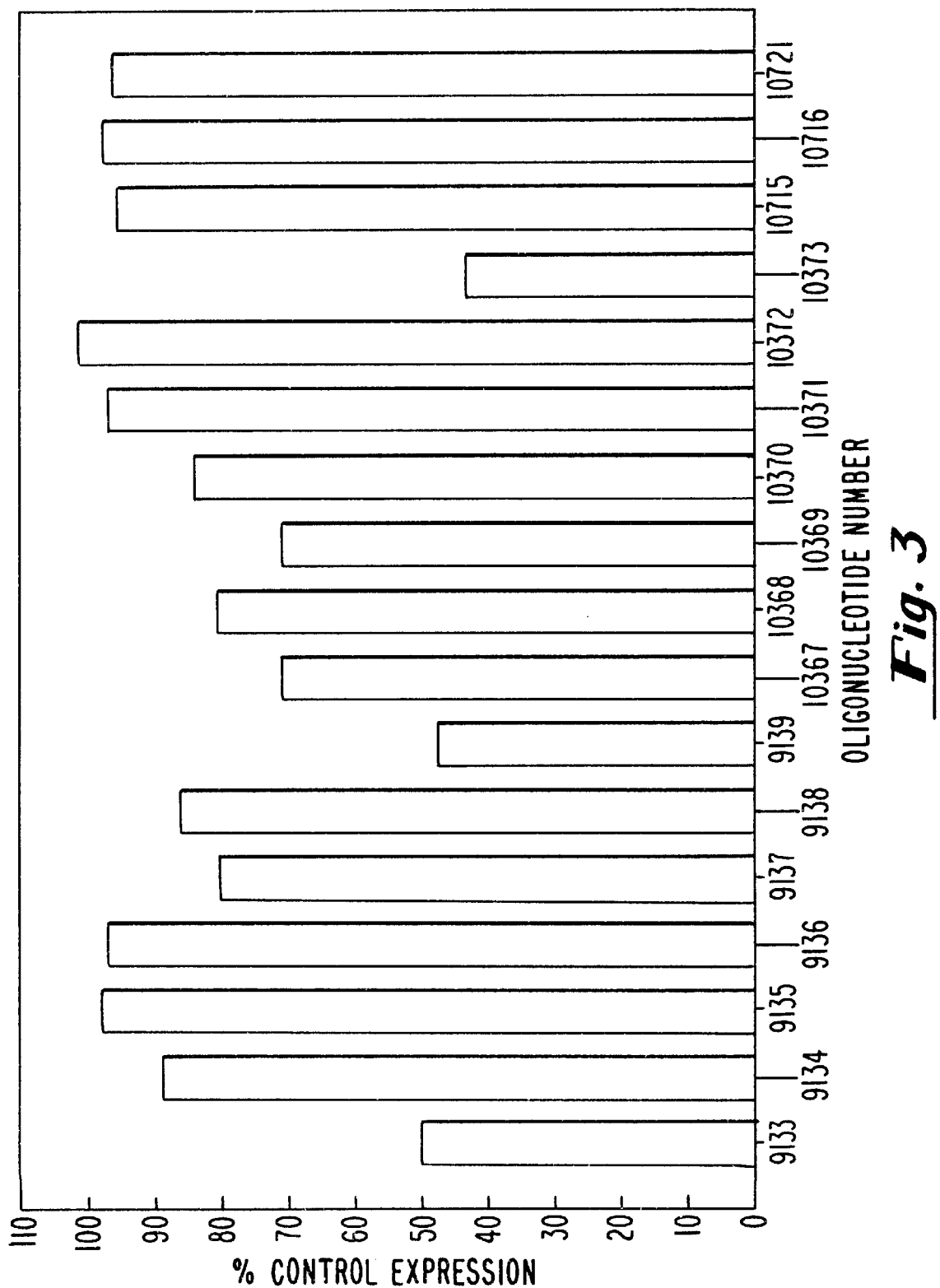
FIG. 3 is a bar graph showing the inhibitory effect of the indicated oligonucleotides on cell surface expression of B7-2 in COS-7 cells.

In an initial screen, the ability of hB7-2 oligonucleotides to inhibit B7-2 expression was evaluated by measuring the cell surface expression of B7-2 in transfected COS-7 cells by flow cytometry. The methods used were similar to those given in Example 2, with the exceptions that (1) COS-7 cells were transfected with the plasmids pbcB7-2 or BBG-58, a human ICAM-1 (CD54) expression vector (R&D Systems, Minneapolis, Minn.) introduced into cells by standard calcium phosphate transfection, (2) the oligonucleotides used were those described in Table 2, and (3) a conjugated anti-B7-2 antibody (i.e., anti-hCD86-FITC or anti-CD86-PE, PharMingen, San Diego, Calif.; PE: phycoerythrin) was used during flow cytometry.
Results:

The results are shown in FIG. 3. At a concentration of 200 nM, ISIS 9133, ISIS 9139 and ISIS 10373 exhibited inhibitory activity of 50% or better and are therefore highly preferred. These oligonucleotides are targeted to the 3' untranslated region (ISIS 9133), the translation initiation codon region (ISIS 9139) and the 5' untranslated region (ISIS 10373). At the same concentration, ISIS 10715, ISIS 10716 and ISIS 10721, which are scrambled controls for ISIS 9133, ISIS 9139 and ISIS 10373, respectively, showed no inhibitory activity. Treatment with ISIS 10367 and ISIS 10369 resulted in greater than 25% inhibition, and these oligonucleotides are thus also preferred. These oligonucleotides are targeted to the 5' (ISIS 10367) and 3' (ISIS 10369) untranslated regions.

Example 4

Modulation of hB7-2 mRNA by Oligonucleotides
Methods:

For ribonuclease protection assays, cells were harvested 18 hours after completion of oligonucleotide treatment using a Totally RNA™ kit (Ambion, Austin, Tex.). The probes for the assay were generated from plasmids pcB7-2 (linearized by digestion with Bgl II) and pTRI-b-actin (Ambion Inc., Austin, Tex.). In vitro transcription of the linearized plasmid from the SP6 promoter was performed in the presence of α-$^{32}$P-UTP (800 Ci/mmole) yielding an antisense RNA complementary to the 3' end of B7-2 (position 1044–1391). The probe was gel-purified after treatment with DNase I to remove DNA template. Ribonuclease protection assays were carried out using an RPA II™ kit (Ambion) according to the manufacturer's directions. Total RNA (5 µg) was hybridized overnight, at 42° C., with $10^5$ cpm of the B7-2 probe or a control beta-actin probe. The hybridization reaction was then treated, at 37° C. for 30 minutes, with 0.4 units of RNase A and 2 units of RNase T1. Protected RNA was precipitated, resuspended in 10 µL of gel loading buffer and electrophoresed on a 6% acrylamide gel with 50% w/v urea at 20 W. The gel was then exposed and the lanes quantitated using a PhosphorImager (Molecular Dynamics, Sunnyvale, Calif.) essentially according to the manufacturer's instructions.

Results:

The extent of oligonucleotide-mediated hB7-2 mRNA modulation generally paralleled the effects seen for hB7-2 protein (Table 5). As with the protein expression (flow cytometry) assays, the most active oligonucleotides were ISIS 9133, ISIS 9139 and 10373. None of the oligonucleotides tested had an inhibitory effect on the expression of b-actin mRNA in the same cells.

TABLE 5

Activities of Oligonucleotides Targeted to hB7-2 mRNA

| ISIS NO. | SEQ ID NO. | % Control Protein | % Control RNA Expression |
| --- | --- | --- | --- |
| 9133 | 3 | 70.2 | 46.0 |
| 9134 | 4 | 88.8 | 94.5 |
| 9135 | 5 | 98.2 | 83.4 |
| 9136 | 6 | 97.1 | 103.1 |
| 9137 | 7 | 80.5 | 78.1 |
| 9138 | 8 | 86.4 | 65.9 |
| 9139 | 9 | 47.9 | 32.6 |
| 10367 | 10 | 71.3 | 52.5 |
| 10368 | 11 | 81.0 | 84.5 |
| 10369 | 12 | 71.3 | 81.5 |
| 10370 | 13 | 84.3 | 83.2 |
| 10371 | 14 | 97.3 | 92.9 |
| 10372 | 15 | 101.7 | 82.5 |
| 10373 | 16 | 43.5 | 32.7 |

Example 5

Additional hB7-1 and hB7-2 Oligonucleotides

Oligonucleotides having structures and/or sequences that were modified relative to the oligonucleotides identified during the initial screening were prepared. These oligonucleotides were evaluated for their ability to modulate human B7-2 expression using the methods described in the previous Examples.

Figure 4:
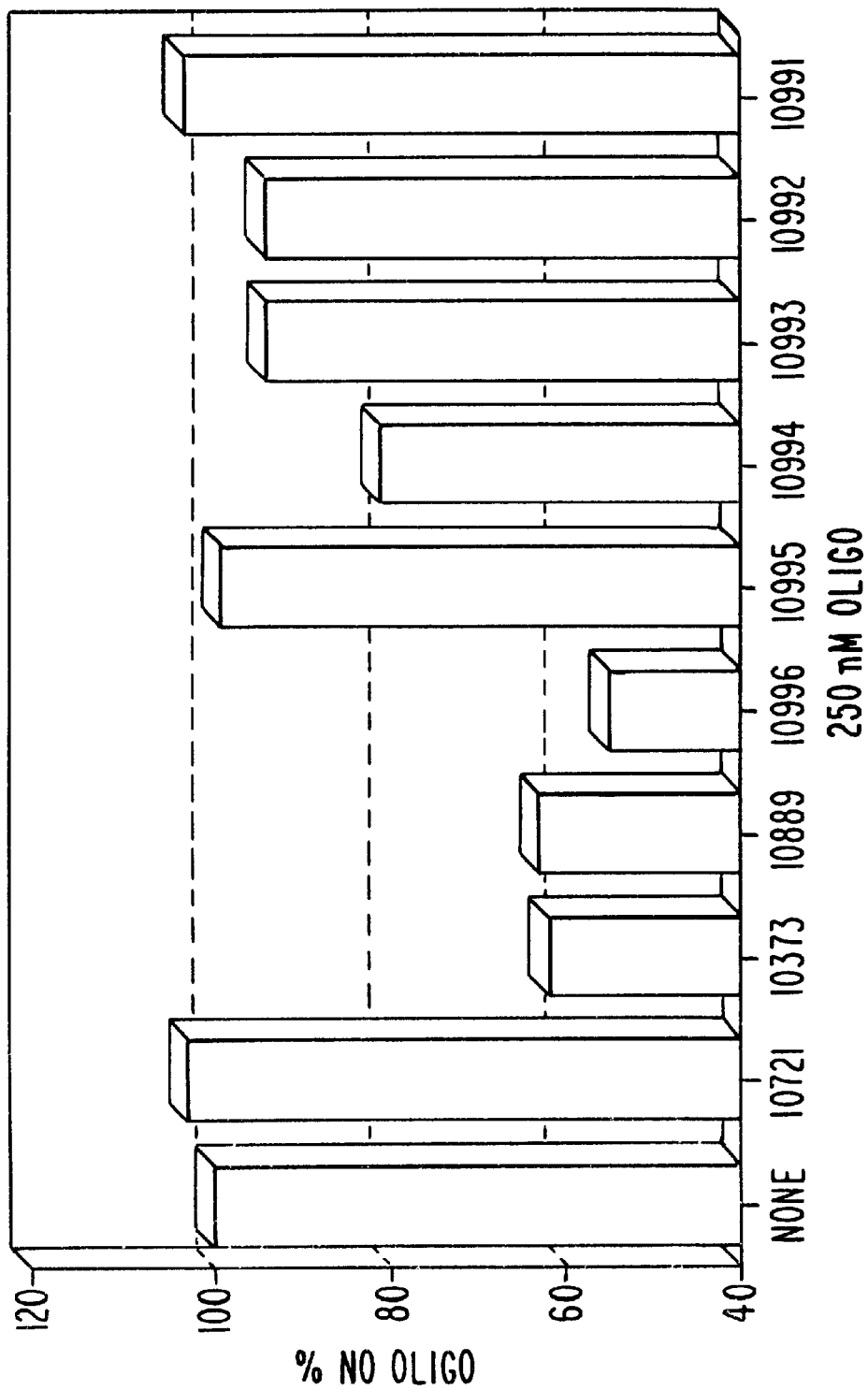
FIG. 4 is a bar graph showing the inhibitory effect of the indicated oligonucleotides, including ISIS 10373 (a 20-mer) and ISIS 10996 (a 15-mer) on cell surface expression of B7-2 in COS-7 cells.

ISIS 10996, an oligonucleotide having a 15 nucleotide sequence derived from the 20 nucleotide sequence of ISIS 10373, was also prepared and evaluated. ISIS 10996 comprises 15 nucleotides, 5'-GCG-AGC-TCC-CCG-TAC (SEQ ID NO: 90) contained within the sequence of ISIS 10373. Both ISIS 10373 and 10996 overlap a potential stem-loop structure located within the B7-2 message comprising bases 1–67 of the sequence of hB7-2 presented by Azuma et al. (Nature, 1993, 366, 76). While not intending to be bound by any particular theory regarding their mode(s) of action, ISIS 10373 and ISIS 10996 have the potential to bind as loop 1 pseudo-half-knots at a secondary structure within the target RNA. U.S. Pat. No. 5,5152,438, which issued Apr. 30, 1996, the contents of which are hereby incorporated by reference, describes methods for modulating gene expression by the formation of pseudo-half-knots. Regardless of their mode(s) of action, despite having a shorter length than ISIS 10373, the 15-mer ISIS 10996 is as (or more) active in the B7-2 protein expression assay than the 20-mer from which it is derived (FIG. 4; ISIS 10721 is a scrambled control for ISIS 10373). A related 16-mer, ISIS 10889, was also active in the B7-2 protein expression assay. However, a structurally related 14-mer (ISIS 10995), 13-mer (ISIS 10994), 12-mer (ISIS 10993), 11-mer (ISIS 10992) and 10-mer (ISIS 10991) exhibited little or no activity in this assay. ISIS 10996 was further derivatized in the following ways.

ISIS 10996 derivatives having 2' methoxethoxy substitutions were prepared, including a fully substituted derivative (ISIS 11539), "gapmers" (ISIS 11541 and 11543) and "wingmers" (ISIS 11545 and 11547). As explained in Example 5, the 2' methoxyethoxy substitution prevents the action of some nucleases (e.g., RNase H) but enhances the affinity of the modified oligonucleotide for its target RNA molecule. These oligonucleotides are tested for their ability to modulate hB7-2 message or function according to the methods of Examples 3, 4, 7 and 8.

ISIS 10996 derivatives were prepared in order to be evaluated for their ability to recruit RNase L to a target RNA molecule, e.g., hB7-2 message. RNase L binds to, and is activated by, $(2'-5')(A)_n$, which is in turn produced from ATP by $(2'-5')(A)_n$ synthetase upon activation by, e.g., interferon. RNase L has been implicated in antiviral mechanisms and in the regulation of cell growth as well (Sawai, Chemica Scripta, 1986, 21, 169; Charachon et al., Biochemistry, 1990, 29, 2550). The combination of anti-B7 oligonucleotides conjugated to $(2'-5')(A)_n$ is expected to result in the activation of RNase L and its targeting to the B7 message complementary to the oligonucleotide sequence. The following oligonucleotides have identical sequences (i.e., that of ISIS 10996) and identical $(2'-5')(A)_4$ "caps" on their 5' termini: ISIS 12492, 12495, 12496 and 13107. The adenosyl residues have 3' hydroxyl groups and are linked to each other by phosphorothioate linkages. The (3'-5') portion of the oligonucleotide, which has a sequence complementary to a portion of the human B7-2 RNA, is conjugated to the (2'-5') $(A)_4$ "cap" via a phosphorothioate linkage from the 5' residue of the (3'-5') portion of the oligonucleotide to an n-aminohexyl linker which is bonded to the "cap" via another phosphorothioate linkage. In order to test a variety of chemically diverse oligonucleotides of this type for their ability to recruit RNase L to a specific message, different chemical modifications were made to this set of four oligonucleotides as follows. ISIS 12496 consists of unmodified oligonucleotides in the (3'-5') portion of the oligonucleotide.

In ISIS 13107, phosphorothioate linkages replace the phosphate linkages found in naturally occurring nucleic acids. Phosphorothioate linkages are also employed in ISIS 12492 and 12495, which additionally have 2'-methoxyethoxy substitutions. These oligonucleotides are tested for their ability to modulate hB7-2 message or function according to the methods of Examples 3, 4, 7 and 8.

Derivatives of ISIS 10996 having modifications at the 2' position were prepared and evaluated. The modified oligonucleotides included ISIS 11539 (fully 2'-O-methyl), ISIS 11541 (having 2'-O-methyl "wings" and a central 7-base "gap"), ISIS 11543 (2'-O-methyl wings with a 9-base gap), ISIS 11545 (having a 5' 2'-O-methyl wing) and ISIS 11547 (having a 3' 2'-O-methyl wing). The results of assays of 2'-O-methyl oligonucleotides were as follows. ISIS 11539, the fully 2' O-methyl version of ISIS 10996, was not active at all in the protein expression assay. The gapped and winged oligonucleotides (ISIS 11541, 11543, 11545 and 11547) each showed some activity at 200 nM (i.e., from 60 to 70% expression relative to untreated cells), but less than that demonstrated by the parent compound, ISIS 10996 (i.e., about 50% expression). Similar results were seen in RNA expression assays.

ISIS 10782, a derivative of ISIS 10373 to which cholesterol has been conjugated via a 5' n-aminohexyl linker, was prepared. Lipophilic moieties such as cholesterol have been reported to enhance the uptake by cells of oligonucleotides in some instances, although the extent to which uptake is enhanced, if any, remains unpredictable. ISIS 10782, and other oligonucleotides comprising lipophilic moieties, are tested for their ability to modulate B7-2 message or function according to the methods of Examples 3, 4, 7 and 8.

A series of 2'-methoxyethoxy (herein, "2'ME") and 2'-fluoride (herein, "2'F") "gapmer" derivatives of the hB7-1 oligonucleotides ISIS 12361 (ISIS Nos. 12348 and 12473, respectively), ISIS 12362 (ISIS Nos. 12349 and 12474), ISIS 12363 (ISIS Nos. 12350 and 12475), ISIS 12364 (ISIS Nos. 12351 and 12476), ISIS 12365 (ISIS Nos. 12352 and 12477), ISIS 12366 (ISIS Nos. 12353 and 12478), ISIS 12367 (ISIS Nos. 12354 and 12479), ISIS 12368 (ISIS Nos. 12355 and 12480), ISIS 12369 (ISIS Nos. 12356 and 12481) and ISIS 12370 (ISIS Nos. 12357 and 12482) were prepared. The central, non-2'-modified portions ("gaps") of these derivatives support RNase H activity when the oligonucleotide is bound to its target RNA, even though the 2'-modified portions do not. However, the 2'-modified "wings" of these oligonucleotides enhance their affinity to their target RNA molecules (Cook, Chapter 9 In: *Antisense Research and Applications*, Crooke et al., eds., CRC Press, Boca Raton, 1993, pp. 171–172).

Another 2' modification is the introduction of a methoxy (MO) group at this position. Like 2'ME- and 2'F-modified oligonucleotides, this modification prevents the action of RNase H on duplexes formed from such oligonucleotides and their target RNA molecules, but enhances the affinity of an oligonucleotide for its target RNA molecule. ISIS 12914 and 12915 comprise sequences complementary to the 5' untranslated region of alternative hB7-1 mRNA molecules, which arise from alternative splicing events of the primary hB7-1 transcript. These oligonucleotides include 2' methoxy modifications, and the enhanced target affinity resulting therefrom may allow for greater activity against alternatively spliced B7-1 mRNA molecules which may be present in low abundance in some tissues (Inobe et al., *J. Immun.*, 1996, 157, 582). Similarly, ISIS 13498 and 13499, which comprise antisense sequences to other alternative hB7-1 mRNAs, include 2' methoxyethoxy modifications in order to enhance their affinity for their target molecules, and 2' methoxyethoxy or 2' methoxy substitutions are incorporated into the hB7-2 oligonucleotides ISIS 12912, 12913, 13496 and 13497. These oligonucleotides are tested for their ability to modulate hB7-1 essentially according to the methods of Example 2 or hB7-2 according to the methods of Examples 3, 4, 7 and 8, with the exception that, when necessary, the target cells are transfected with a cDNA clone corresponding to the appropriate alternatively spliced B7 transcript.

Example 6

Specificity of Antisense Modulation

Figure 5:
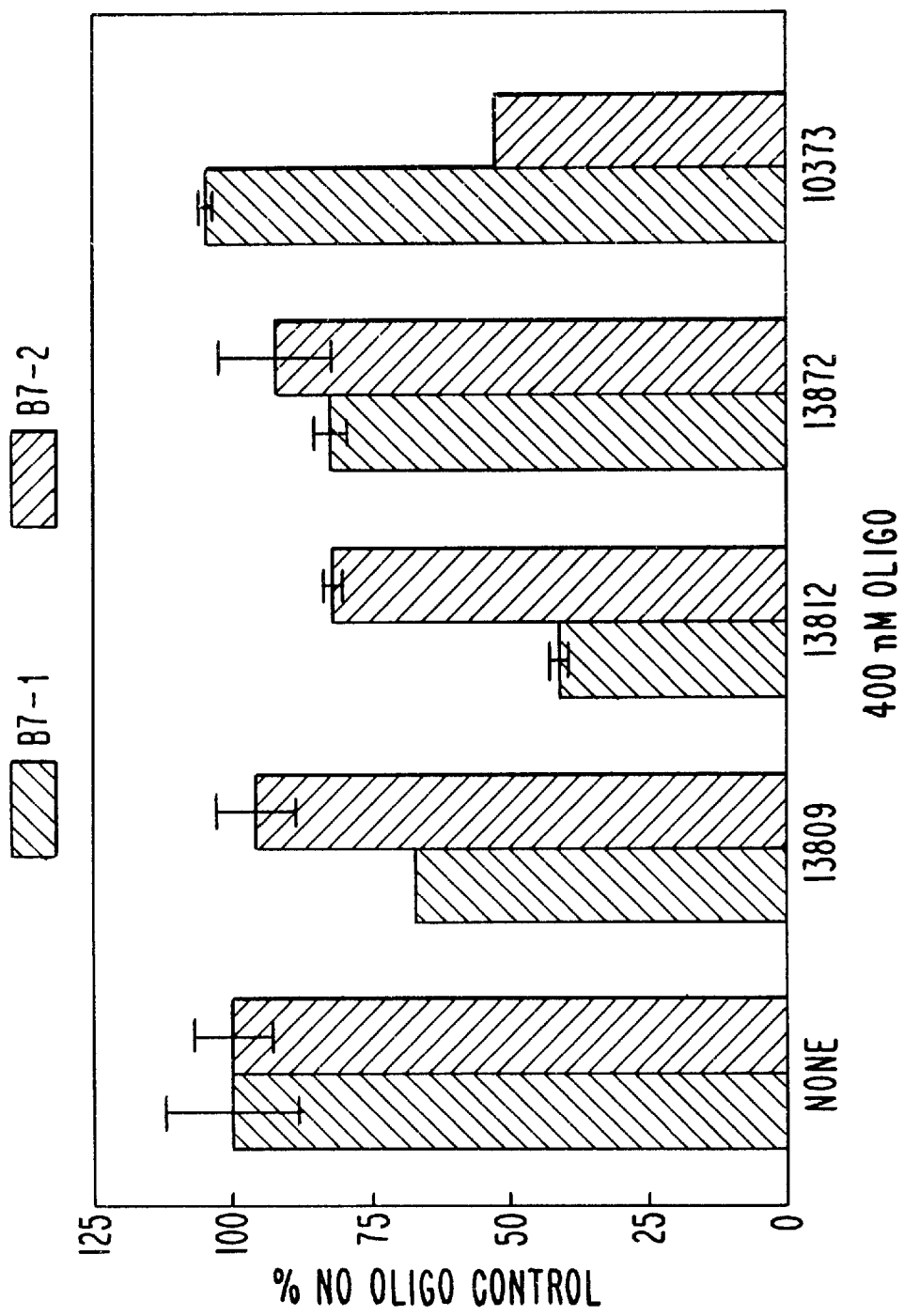
FIG. 5 is a bar graph showing the specificity of inhibition of B7-1 or B7-2 protein expression by oligonucleotides. Cross-hatched bars, B7-1 levels; striped bars, B7-2 levels.

Several oligonucleotides of the invention were evaluated in a cell surface expression flow cytometry assay to determine the specificity of the oligonucleotides for B7-1 as contrasted with activity against B7-2. The oligonucleotides tested in this assay included ISIS 13812, an inhibitor of B7-1 expression (FIG. 1; Example 2) and ISIS 10373, an inhibitor of B7-2 expression (FIG. 3; Example 3). The results of this assay are shown in FIG. 5. ISIS 13812 inhibits B7-1 expression with little or no effect on B7-2 expression. As is also seen in FIG. 5, ISIS 10373 inhibits B7-2 expression with little or no effect on B7-1 expression. ISIS 13872 (SEQ ID NO: 37, AGT-CCT-ACT-ACC-AGC-CGC-CT), a scrambled control of ISIS 13812, and ISIS 13809 (SEQ ID NO: 51) were included in these assays and demonstrated essentially no activity against either B7-1 or B7-2.

Example 7

Modulation of hB7-2 Expression by Oligonucleotides in Antigen Presenting Cells

The ability of ISIS 10373 to inhibit expression from the native B7-2 gene in antigen presenting cells (APCs) was evaluated as follows.

Methods:

Monocytes were cultured and treated with oligonucleotides as follows. For dendritic cells, EDTA-treated blood was layered onto Polymorphprep™ (1.113 g/mL; Nycomed, Oslo, Norway) and sedimented at 500× g for 30 minutes at 20° C. Mononuclear cells were harvested from the interface. Cells were washed with PBS, with serum-free RPMI media (Moore et al., *N.Y. J. Med.*, 1968, 68, 2054) and then with RPMI containing 5% fetal bovine serum (FBS). Monocytes were selected by adherence to plastic cell culture cell culture dishes for 1 h at 37° C. After adherence, cells were treated with oligonucleotides in serum-free RPMI containing Lipofectin™ (8 µg/mL). After 4 hours, the cells were washed. Then RPMI containing 5% FBS and oligonucleotide was added to cells along with interleukin-4 (IL-4; R&D Systems, Minneapolis, Minn.) (66 ng/mL) and granulocyte-macrophage colony-stimulating factor (GM-CSF; R&D Systems, Minneapolis, Minn.) (66 ng/mL) to stimulate differentiation (Romani et al., *J. Exp. Med.*, 1994, 180, 83, 1994). Cells were incubated for 48 hours, after which cell surface expression of various molecules was measured by flow cytometry.

Mononuclear cells isolated from fresh blood were treated with oligonucleotide in the presence of cationic lipid to promote cellular uptake. As a control oligonucleotide, ISIS 2302 (an inhibitor of ICAM-1 expression; SEQ ID NO: 17) was also administered to the cells. Expression of B7-2 protein was measured by flow cytometry according to the methods of Example 2. Monoclonal antibodies not described in the previous Examples included anti-hCD3 (Ancell, Bayport, Minn.) and anti-HLADR (Becton Dickinson, San Jose, Calif.).

Figure 6:
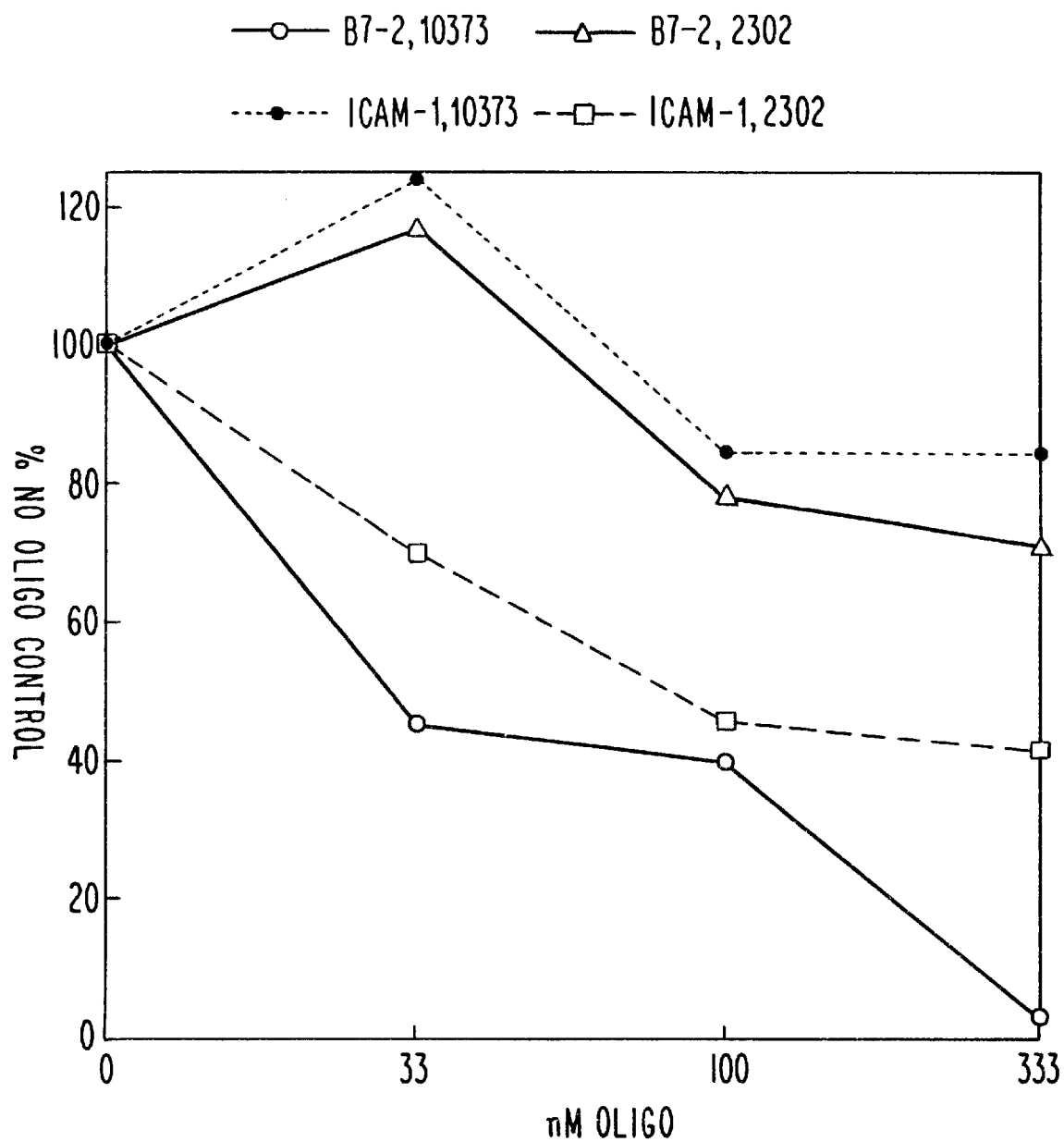
FIG. 6 is a dose-response curve showing the inhibitory effect of oligonucleotides having antisense sequences to ICAM-1 (ISIS 2302) or B7-2 (ISIS 10373) on cell surface expression of the ICAM-1 and B7-2 proteins. Solid line with X's, levels of B7-1 protein on cells treated with ISIS 10373; dashed line with asterisks, levels of ICAM-1 protein on cells treated with ISIS 10373; solid line with triangles, levels of B7-1 protein on cells treated with ISIS 2302; solid line with squares, levels of ICAM-1 protein on cells treated with ISIS 10373.

Results:

As shown in FIG. 6, ISIS 10373 has a significant inhibitory effect on B7-2 expression with an $IC_{50}$ of approximately 250 nM. ISIS 10373 had only a slight effect on ICAM-1 expression even at a dose of 1 µM. ISIS 2302 (SEQ ID NO: 17), a control oligonucleotide which has been shown to inhibit ICAM-1 expression, had no effect on B7-2 expression, but significantly decreased ICAM-1 levels with an $IC_{50}$ of approximately 250 nM. Under similar conditions, ISIS 10373 did not affect the cell surface expression of B7-1, HLA-DR or CD3 as measured by flow cytometry.

Example 8

Modulation of T Cell Proliferation by Oligonucleotides

The ability of ISIS 2302 and ISIS 10373 to inhibit T cell proliferation was evaluated as follows. Monocytes treated with oligonucleotide and cytokines (as in Example 6) were used as antigen presenting cells in a T cell proliferation assay. The differentiated monocytes were combined with CD4+ T cells from a separate donor. After 48 hours, proliferation was measured by [$^3$H] thymidine incorporation.
Methods:

For T cell proliferation assays, cells were isolated from EDTA-treated whole blood as described above, except that a faster migrating band containing the lymphocytes was harvested from just below the interface. Cells were washed as described in Example 6 after which erythrocytes were removed by $NH_4Cl$ lysis. T cells were purified using a T cell enrichment column (R&D Systems, Minneapolis, Minn.) essentially according to the manufacturer's directions. CD4+ T cells were further enriched from the entire T cell population by depletion of CD8+ cells with anti-CD8-conjugated magnetic beads (AMAC, Inc., Westbrook, Me.) according to the manufacturer's directions. T cells were determined to be >80% CD4+ by flow cytometry using Cy-chrome-conjugated anti-CD4 mAb (PharMingen, San Diego, Calif.).

Figure 7:
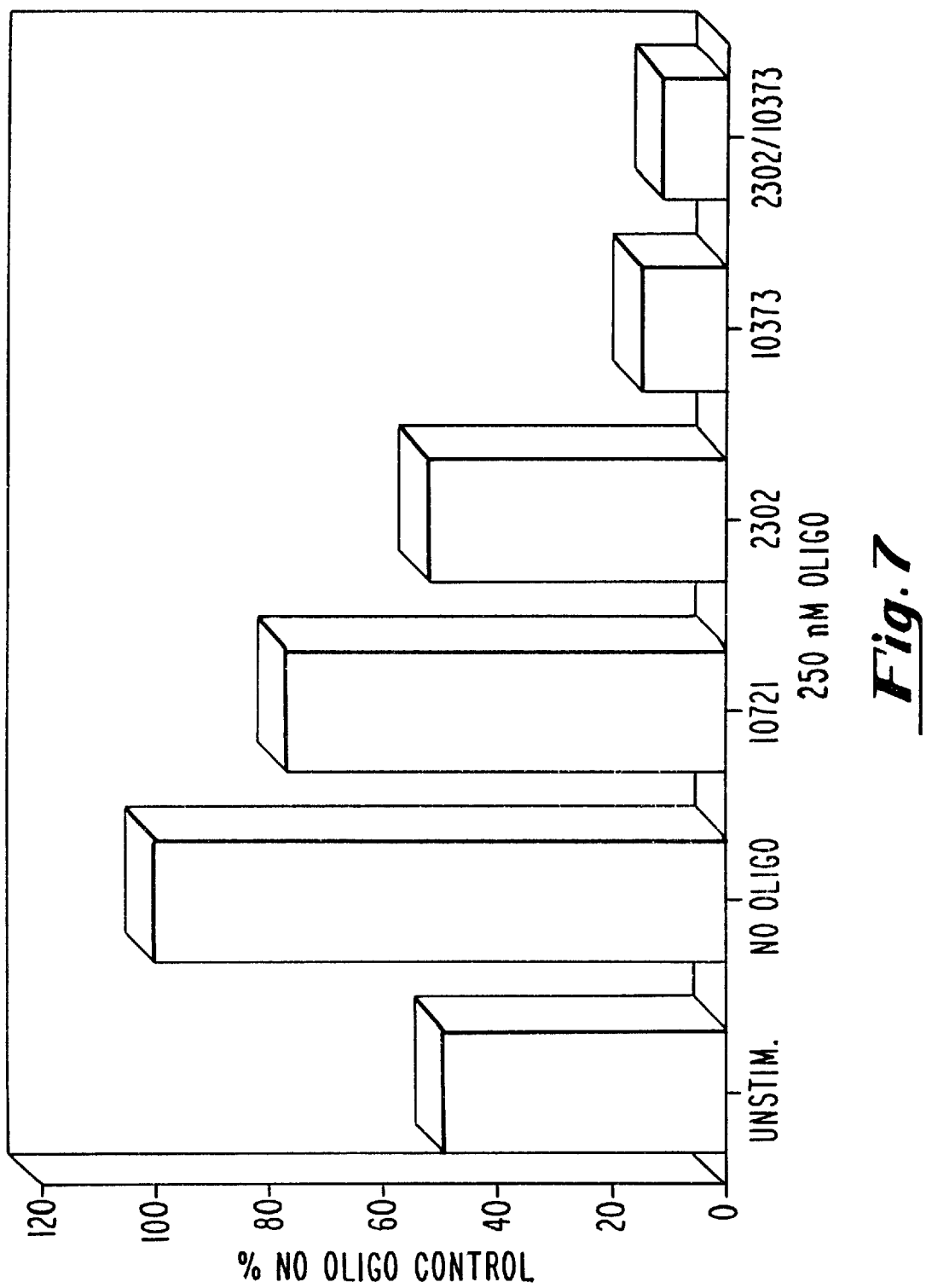
FIG. 7 is a bar graph showing the effect of the indicated oligonucleotides on T cell proliferation.

Antigen presenting cells (APCs) were isolated as described in Example 6 and treated with mitomycin C (25 µg/mL) for 1 hour then washed 3 times with PBS. APCs ($10^5$ cells) were then combined with $4 \times 10^4$ CD4+ T cells in 350 µL of culture media. Where indicated, purified CD3 mAb was also added at a concentration of 1 µg/mL. During the last 6 hours of the 48 hour incubation period, proliferation was measured by determining uptake of 1.5 uCi of [$^3$H]-thymidine per well. The cells were harvested onto filters and the radioactivity measured by scintillation counting.
Results:

As shown in FIG. 7, mononuclear cells which were not cytokine-treated slightly induced T cell proliferation, presumably due to low levels of costimulatory molecules expressed on the cells. However, when the cells were treated with cytokines and induced to differentiate to dendritic-like cells, expression of both ICAM-1 and B7-2 was strongly upregulated. This resulted in a strong T cell proliferative response which could be blocked with either anti-ICAM-1 (ISIS 2302) or anti-B7-2 (ISIS 10373) oligonucleotides prior to induction of the mononuclear cells. The control oligonucleotide (ISIS 10721) had an insignificant effect on T cell proliferation. A combination treatment with both the anti-ICAM-1 (ISIS 2302) and anti-B7-2 (ISIS 10373) oligonucleotides resulted in a further decrease in T cell response.

Example 9

Modulation of Murine B7 Genes by Oligonucleotides

Oligonucleotides (see Table 4) capable of inhibiting expression of murine B7-2 transiently expressed in COS-7 cells were identified in the following manner. A series of phosphorothioate oligonucleotides complementary to murine B7-2 (mB7-2) cDNA were screened for their ability to reduce mB7-2 levels (measured by flow cytometry as in Example 2, except that a conjugated anti-mB7-2 antibody (i.e., anti-mCD86-PE, PharMingen, San Diego, Calif.) in COS-7 cells transfected with an mB7-2 cDNA clone. Anti-mB7-2 antibody may also be obtained from the hybridoma deposited at the ATCC under accession No. HE-253. Oligonucleotides (see Table 2) capable of modulating murine B7-1 expression are isolated in like fashion, except that a conjugated anti-mB7-1 antibody is used in conjunction with COS-7 cells transfected with an mB7-1 cDNA clone.

Figure 8:
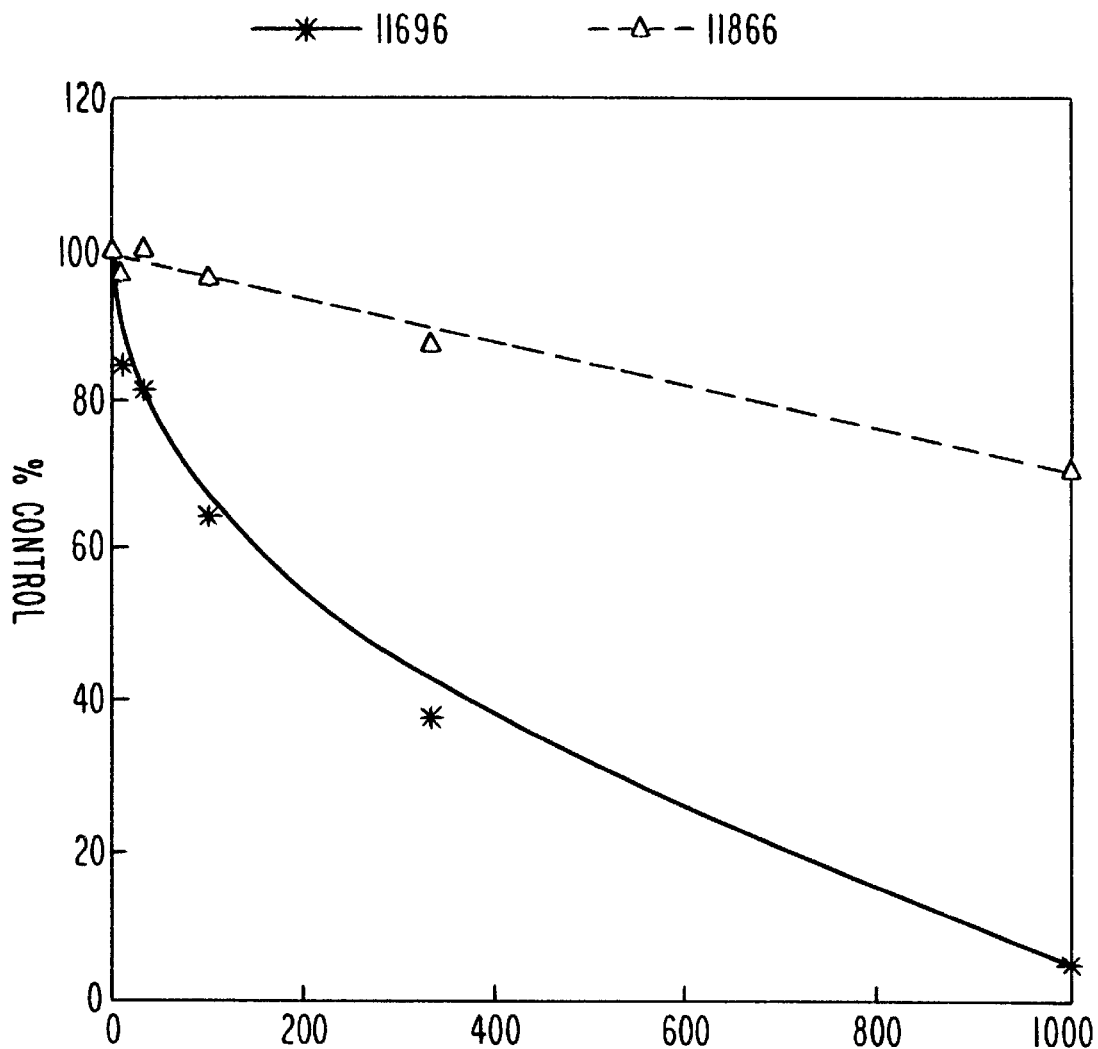
FIG. 8 is a dose-response curve showing the inhibitory effect of oligonucleotides on murine B7-2 protein expression in COS-7 cells. Solid line with asterisks, ISIS 11696; dashed line with triangles, ISIS 11866.

For murine B7-2, the most active oligonucleotide identified was ISIS 11696 (GGA-TTG-CCA-AGC-CCA-TGG-TG, SEQ ID NO: 18), which is complementary to position 96-115 of the cDNA, a site which includes the translation initiation (AUG) codon. FIG. 8 shows a dose-response curve for ISIS 11696 and a scrambled control, ISIS 11866 (CTA-AGT-AGT-GCT-AGC-CGG-GA, SEQ ID NO: 19). ISIS 11696 inhibited cell surface expression of B7-2 in COS-7 cells with an $IC_{50}$ in the range of 200–300 nM, while ISIS 11866 exhibited less than 20% inhibition at the highest concentration tested (1000 nM).

In order to further evaluate the murine B7-2 antisense oligonucleotides, the IC-21 cell line was used. IC-21 monocyte/macrophage cell line expresses both B7-1 and murine B7-2 (mB7-2) constitutively. A 2-fold induction of expression can be achieved by incubating the cells in the presence of lipopolysaccharide (LPS; GIBCO-BRL, Gaithersburg, Md.) (Hathcock et al., Science, 1993, 262, 905).

IC-21 cells (ATCC; accession No. TIB 186) were seeded at 80% confluency in 12-well plates in DMEM media with 10% FCS. The cells were allowed to adhere to the plate overnight. The following day, the medium was removed and the cells were washed with PBS. Then 500 µL of Opti-MEM™ (GIBCO-BRL, Gaithersburg, Md.) supplemented with 15 µg/mL of Lipofectin™ (GIBCO-BRL, Gaithersburg, Md.) was added to each well. Oligonucleotides were then added directly to the medium at the indicated concentrations. After incubation for 4 hours, the cells were washed with PBS and incubated overnight in culture medium supplemented with 15 µg/mL of LPS. The following day, cells were harvested by scraping, then analyzed for cell surface expression by flow cytometry.

Figure 9:
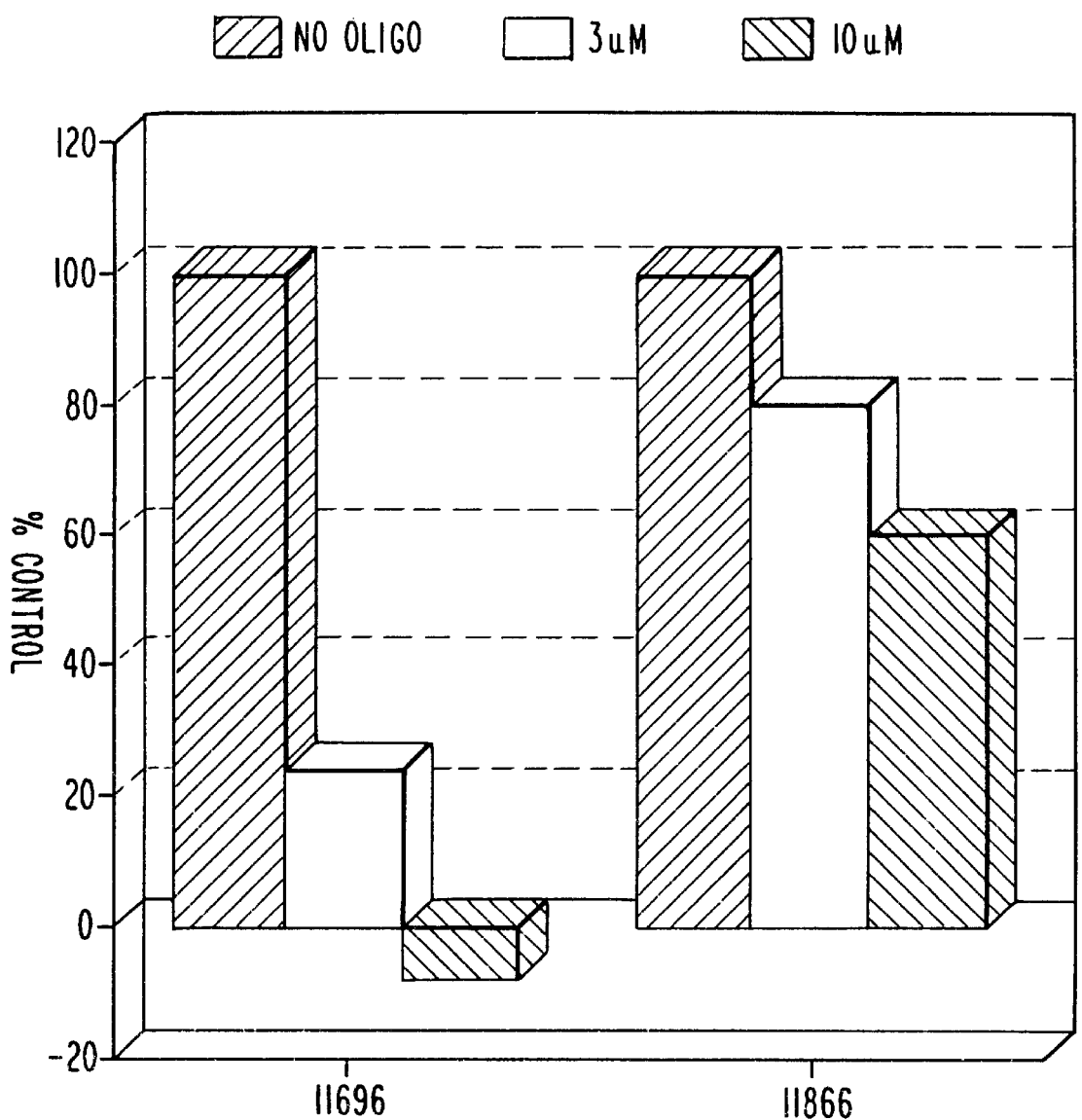
FIG. 9 is a bar graph showing the effect of oligonucleotides ISIS 11696 and ISIS 11866 on cell surface expression of murine B7-2 protein in IC-21 cells. Left (black) bars, no oligonucleotide; middle bars, 3 $\mu$M indicated oligonucleotide; right bars, 10 $\mu$M indicated oligonucleotide.

ISIS 11696 and ISIS 11866 were administered to IC-21 cells in the presence of Lipofectin™ (GIBCO-BRL, Gaithersburg, Md.). The results are shown in FIG. 9. At a concentration of 10 µM, ISIS 11696 inhibited mB7-2 expression completely (and decreased mB7-2 levels below the constitutive level of expression), while the scrambled control oligonucleotide, ISIS 11866, produced only a 40% reduction in the level of induced expression. At a concentration of 3 uM, levels of induced expression were greatly reduced by ISIS 11696, while ISIS 11866 had little effect.

Modified oligonucleotides, comprising 2' substitutions (e.g., 2' methoxy, 2' methoxyethoxy) and targeted to alternative transcripts of murine B7-1 (ISIS 12914, 12915, 13498, 13499) or murine B7-2 (ISIS 13100, 13100 and 13102) were prepared. These oligonucleotides are tested for their ability to modulate murine B7 essentially according to the above methods using IC-21 cells or COS-7 transfected with a cDNA clone corresponding to the appropriate alternatively spliced B7 transcript.

Example 10

Modulation of Allograft Rejection by Oligonucleotides

A murine model for evaluating compounds for their ability to inhibit heart allograft rejection has been previously described (Stepkowski et al., *J. Immunol.*, 1994, 153, 5336). This model was used to evaluate the immunosuppressive capacity of antisense oligonucleotides to B7 proteins alone or in combination with antisense oligonucleotides to intercellular dhesion molecule-1 (ICAM-1).

Methods:

Heart allograft rejection studies and oligonucleotide treatments of BALE/c mice were performed essentially as previously described (Stepkowski et al., *J. Immunol.*, 1994, 153, 5336). Antisense oligonucleotides used included ISIS 11696, ISIS 3082 (targeted to ICAM-1) and ISIS 1082 (a control oligonucleotide targeted to the herpes virus UL-13 gene sequence). Dosages used were 1, 2, 2.5, 5 or 10 mg/kg of individual oligonucleotide (as indicated below); when combinations of oligonucleotides were administered, each oligonucleotide was given at a dosage of 1, 5 or 10 mg/kg (total oligonucleotide dosages of 2, 10 and 20 mg/kg, respectively). The survival times of the transplanted hearts and their hosts were monitored and recorded.

Results:

The mean survival time for untreated mice was 8.2±0.8 days (7,8,8,8,9,9 days). Treatment of the mice for 7 days with ISIS 1082 (SEQ ID NO: 125, unrelated control oligonucleotide) slightly reduced the mean survival times to 7.1±0.7 days (5 mg/kg/day; 6,7,7,7,8,8) or 7.0±0.8 days(10 mg/kg/day; 6,7,7,8). Treatment of the mice for seven days with the murine B7-2 oligonucleotide ISIS 11696 (SEQ ID NO: 108) increased the mean survival time to 9.3 days at two doses (2 mg/kg/day, 9.3±0.6 days, 9,9,10; 10 mg/kg/day, 9.3±1.3 days, 8,9,9,11). Treatment of mice for seven days with an ICAM-1 oligonucleotide, ISIS 3082, also increased the mean survival of the mice over several doses. Specifically, at 1 mg/kg/day, the mean survival time (MSD) was 11.0±0.0 (11,11,11); at 2.5 mg/kg/day, the MSD was 12.0±2.7 (10,12,13,16); at 5 mg/kg/day, the MSD was 14.1±2.7 (10,12,12,13,16,16,17,17); and, at 10 mg/kg/day, the MSD was 15.3±5.8 (12,12,13,24). Some synergistic effect was seen when the mice were treated for seven days with 1 mg/kg/day each of ISIS 3082 and 11696: the MSD was 13.8±1.0 (13,13,14,15).

Example 11

Detection of Nucleic Acids Encoding B7 Proteins

Oligonucleotides are radiolabeled after synthesis by $^{32}$P-labeling at the 5' end with polynucleotide kinase. Sambrook et al., "Molecular Cloning. A Laboratory Manual," Cold Spring Harbor Laboratory Press, 1989, Volume 2, pg. 11.31. Radiolabeled oligonucleotide capable of hybridizing to a nucleic acid encoding a B7 protein is contacted with a tissue or cell sample suspected of B7 protein expression under conditions in which specific hybridization can occur, and the sample is washed to remove unbound oligonucleotide. A similar control is maintained wherein the radiolabeled oligonucleotide is contacted with a normal tissue or cell sample under conditions that allow specific hybridization, and the sample is washed to remove unbound oligonucleotide. Radioactivity remaining in the samples indicates bound oligonucleotide and is quantitated using a scintillation counter or other routine means. A greater amount of radioactivity remaining in the samples, as compared to control tissues or cells, indicates increased expression of a B7 gene, whereas a lesser amount of radioactivity in the samples relative to the controls indicates decreased expression of a B7 gene.

Radiolabeled oligonucleotides of the invention are also useful in autoradiography. A section of tissues suspected of expressing a B7 gene is treated with radiolabeled oligonucleotide and washed as described above, then exposed to photographic emulsion according to standard autoradiography procedures. A control of a normal tissue section is also maintained. The emulsion, when developed, yields an image of silver grains over the regions expressing a B7 gene, which is quantitated. The extent of B7 expression is determined by comparison of the silver grains observed with control and test samples.

Analogous assays for fluorescent detection of expression of a B7 gene use oligonucleotides of the invention which are labeled with fluorescein or other fluorescent tags. Labeled oligonucleotides are synthesized on an automated DNA synthesizer (Applied Biosystems, Foster City, Calif.) using standard phosphoramidite chemistry. b-Cyanoethyldiisopropyl phosphoramidites are purchased from Applied Biosystems (Foster City, Calif.). Fluorescein-labeled amidites are purchased from Glen Research (Sterling, Va.). Incubation of oligonucleotide and biological sample is carried out as described above for radiolabeled oligonucleotides except that, instead of a scintillation counter, a fluorescence microscope is used to detect the fluorescence. A greater amount of fluorescence in the samples, as compared to control tissues or cells, indicates increased expression of a B7 gene, whereas a lesser amount of fluorescence in the samples relative to the controls indicates decreased expression of a B7 gene.

What is claimed is:

1. An oligonucleotide comprising a nucleotide sequence set forth in SEQ ID NO: 24, 27, 30, 31, 32, 34 or 36, wherein said oligonucleotide inhibits expression of a human B7-1 protein.

2. The oligonucleotide of claim 1, wherein at least one covalent linkage of said oligonucleotide is a modified covalent linkage.

3. The oligonucleotide of claim 2, wherein said modified covalent linkage is selected from the group consisting of a phosphorothioate linkage, a phosphotriester linkage, a methyl phosphonate linkage, a methylene(methylimino) linkage, a morpholino linkage, an amide linkage, a polyamide linkage, a short chain alkyl intersugar linkage, a cycloalkyl intersugar linkage, a short chain heteroatomic intersugar linkage and a heterocyclic intersugar linkage.

4. The oligonucleotide of claim 1, wherein at least one nucleotide of said oligonuclootide has a modified sugar moiety.

5. The oligonucleotide of claim 4, wherein said modified sugar moiety is a modification at the 2' position of any nucleotide, the 3' position of the 3' terminal nucleotide or the 5' position of the 5' terminal nucleotide.

6. The oligonucleotide of claim 5, wherein said modification is selected from the group consisting of a substitution of an azido group for a 3' hydroxyl group and a substitution of a hydrogen atom for a 3' or 5' hydroxyl group.

7. The oligonucleotide of claim 5, wherein said modification is a substitution or addition at the 2' position of a moiety selected from the group consisting of —OH, —SH, —SCH$_3$, —F, —OCN, —OCH$_3$OCH$_3$, —OCH$_3$O(CH$_2$)$_n$CH$_3$, —O(CH$_2$)$_n$NH$_2$ or —O(CH$_2$)$_n$CH$_3$ where n is from 1 to about 10, a C$_1$ to C$_{10}$ lower alkyl group, an alkoxyalkoxy group, a substituted lower alkyl group, a substituted alkaryl group, a substituted aralkyl group, —Cl, —Br, —CN, —CF$_3$, —OCF$_3$, an —O-alkyl group, an —S-alkyl group, an N-alkyl group, an O-alkenyl group, an S-alkenyl group, an N-alkenyl group, —SOCH$_3$, —SO$_2$CH$_3$, —ONO$_2$, —NO$_2$, —N$_3$, —NH$_2$, a heterocycloalkyl group, a heterocycloalkaryl group, an aminoalkylamino group, a polyalkylamino group, a substituted silyl group, an RNA cleaving group, a reporter group, a DNA intercalating group, a methoxyethoxy group and a methoxy group.

8. The oligonucleotide of claim 1, wherein at least one nucleotide of said oligonucleotide has a modified nucleobase.

9. The oligonucleotide of claim 8, wherein said modified nucleobase is selected from the group consisting of hypoxanthine, 5-methylcytosine, 5-hydroxymethylcytosine, glycosyl 5-hydroxymethylcytosine, gentiobiosyl 5-hydroxymethylcytosine, 5-bromouracil, 5-hydroxymethyluracil, 6-methyladenine, N$^6$-(6-aminohexyl)adenine, 8-azaguanine, 7-deazaguanine and 2,6-diaminopurine.

10. A pharmaceutical composition comprising the oligonucleotide of claim 1 and a pharmaceutically acceptable carrier.

11. An oligonucleotide of claim 1 wherein said oligonucleotide comprises at least one lipophilic moiety which enhances the cellular uptake of said oligonucleotide.

12. The oligonucleotide of claim 11 wherein said lipophilic moiety is selected from the group consisting of a cholesterol moiety, a cholesteryl moiety, cholic acid, a thioether, a thiocholesterol, an aliphatic chain, a phospholipid, a polyamine chain, a polyethylene glycol chain, adamantane acetic acid, a palmityl moiety, an octadecylamine moiety and a hexylamino-carbonyl-oxycholesterol moiety.

13. A pharmaceutical composition comprising an oligonucleotide of claim 11 and a pharmaceutically acceptable carrier.

14. A pharmaceutical composition comprising
(a) an anti-inflammatory or immunosuppressive agent selected from the group consisting of a soluble ICAM protein, prednisone, methylprednisone, azathioprine, cyclophosphamide, cyclosporine, an interferon, a sympathomimetic, a histamine H$_1$ receptor antagonist, and a histamine H$_2$ receptor antagonist;
(b) an oligonucleotide of claim 1; and
(c) a pharmaceutically acceptable carrier.

15. A pharmaceutical composition comprising
(a) an oligonucleotide comprising 8 to 30 nucleotides connected by covalent linkages, wherein at least one of said covalent linkages is a linkage other than a phosphodiester linkage, wherein said oligonucleotide has a sequence hybridizable with a nucleic acid encoding an ICAM protein and said oligonucleotide modulates the expression of said ICAM protein;
(b) an oligonucleotide of claim 1; and
(c) a pharmaceutically acceptable carrier.

16. A pharmaceutical composition comprising
(a) an oligonucleotide of claim 1;
(b) an oligonucleotide comprising a nucleotide sequence set forth in SEQ ID NO: 3, 9, 10, 12, 16, 84 or 90, wherein said oligonucleotide modulates the expression of said B7-2 protein; and
(c) a pharmaceutically acceptable carrier.

17. A pharmaceutical composition comprising
(a) an anti-inflammatory or immunosuppressive agent selected from the group consisting of a soluble ICAM protein, prednisone, methylprednisone, azathioprine, cyclophosphamide, cyclosporine, an interferon, a sympathomimetic, a histamine H$_1$ receptor antagonist, a histamine H$_2$ receptor antagonist, and an oligonucleotide which modulates the expression of an ICAM protein;
(b) an oligonucleotide of claim 1; and
(c) an oligonucleotide comprising a nucleotide sequence set forth in SEQ ID NO: 3, 9, 10, 12, 16, 84, or 90, wherein said oligonucleotide modulates the expression of said B7-2 protein; and
(d) a pharmaceutically acceptable carrier.

18. A method of modulating the expression of a human B7-1 protein in cells or tissues comprising contacting said cells or tissues with an oligonucleotide of claim 1 under conditions where said oligonucleotide inhibits expression of said human B7-1 protein.

19. A method of inhibiting allograft rejection in an animal comprising administering to said animal an oligonucleotide of claim 1 under conditions where said oligonucleotide inhibits expression of said human B7-1 protein.

20. An oligonucleotide comprising a nucleotide sequence set forth in SEQ ID NO: 3, 9, 10, 12, 16, 84 or 90, wherein said oligonucleotide inhibits expression of a human B7-2 protein.

21. The oligonucleotide of claim 20, wherein at least one covalent linkage of said oligonucleotide is modified.

22. The oligonucleotide of claim 21, wherein said modified covalent linkage is selected from the group consisting of a phosphorothioate linkage, a phosphotriester linkage, a methyl phosphonate linkage, a methylene(methylimino) linkage, a morpholino linkage, an amide linkage, a polyamide linkage, a short chain alkyl intersugar linkage, a cycloalkyl intersugar linkage, a short chain heteroatomic intersugar linkage and a hoterocyclic intersugar linkage.

23. The oligonucleotide of claim 20, wherein at least one nucleotide of said oligonucleotide has a modified sugar moiety.

24. The oligonucleotide of claim 23, wherein said modified sugar moiety is a modification at the 2' position of any nucleotide, the 3' position of the 3' terminal nucleotide or the 5' position of the 5' terminal.

25. The oligonucleotide of claim 24, wherein said modification is selected from the group consisting of a substitution of an azido group for a 3' hydroxyl group and a substitution of a hydrogen atom for a 3' or 5' hydroxyl group.

26. The oligonucleotide of claim 24, wherein said modification is a substitution or addition at the 2' position of a moiety selected from the group consisting of —OH, —SH, —SCH$_3$, —F, —OCN, —OCH$_3$OCH$_3$, —OCH$_3$O(CH$_2$)$_n$CH$_3$, —O(CH$_2$)$_n$NH$_2$ or —O(CH$_2$)$_n$CH$_3$ where n is from 1 to about 10, a C$_1$ to C$_{10}$ lower alkyl group, an alkoxyalkoxy group, a substituted lower alkyl group, a substituted alkaryl group, a substituted aralkyl group, —Cl, —Br, —CN, —CF$_3$, —OCF$_3$, an —O-alkyl group, an —S-alkyl group, an N-alkyl group, an O-alkenyl group, an S-alkenyl group, an N-alkenyl group, —SOCH$_3$, —SO$_2$CH$_3$, —ONO$_2$, —NO$_2$, —N$_3$, —NH$_2$, a heterocycloalkyl group, a heterocycloalkaryl group, an aminoalkylamino group, a polyalkylamino group, a substituted silyl group, an RNA cleaving group, a reporter group, a DNA intercalating group, a methoxyethoxy group and a methoxy group.

27. The oligonucleotide of claim 20, wherein at least one nucleotide of said oligonucleotide has a modified nucleobase.

28. The oligonucleotide of claim 27, wherein said modified nucleobase is selected from the group consisting of hypoxanthine, 5-methylcytosine, 5-hydroxymethylcytosine, glycosyl 5-hydroxymethylcytosine, gentiobiosyl 5-hydroxymethylcytosine, 5-bromouracil, 5-hydroxymethyluracil, 6-methyladenine, $N^6$-(6-aminohexyl)adenine, 8-azaguanine, 7-deazaguanine and 2,6-diaminopurine.

29. A pharmaceutical composition comprising the oligonucleotide of claim 20 and a pharmaceutically acceptable carrier.

30. An oligonucleotide of claim 20 wherein said oligonucleotide comprises at least one lipophilic moiety which enhances the cellular uptake of said oligonucleotide.

31. The oligonucleotide of claim 30 wherein said lipophilic moiety is selected from the group consisting of a cholesterol moiety, a cholesteryl moiety, cholic acid, a thioether, a thiocholesterol, an aliphatic chain, a phospholipid, a polyamine chain, a polyethylene glycol chain, adamantane acetic acid, a palmityl moiety, an octadecylamine moiety and a hexylamino-carbonyl-oxycholesterol moiety.

32. A pharmaceutical composition comprising an oligonucleotide of claim 30 and a pharmaceutically acceptable carrier.

33. A pharmaceutical composition comprising
   (a) an anti-inflammatory or immunosuppressive agent selected from the group consisting of a soluble ICAM protein, prednisone, methylprednisone, azathioprine, cyclophosphamide, cyclosporine, an interferon, a sympathomimetic, a histamine $H_1$ receptor antagonist, and a histamine $H_2$ receptor antagonist;
   (b) an oligonucleotide of claim 20; and
   (c) a pharmaceutically acceptable carrier.

34. A pharmaceutical composition comprising
   (a) an oligonucleotide comprising 8 to 30 nucleotides connected by covalent linkages, wherein at least one of said covalent linkages is a linkage other than a phosphodiester linkage, wherein said oligonucleotide has a sequence hybridizable with a nucleic acid encoding an ICAM protein and said oligonucleotide modulates the expression of said ICAM protein;
   (b) an oligonucleotide of claim 20; and
   (c) a pharmaceutically acceptable carrier.

35. A method of modulating the expression of a human B7-2 protein in cells or tissues comprising contacting said cells or tissues with an oligonucleotide of claim 20 under conditions wherein said oligonucleotide inhibits expression of said human B7-2 protein.

36. The method of claim 35 wherein said cells are antigen presenting cells.

37. The method of claim 18 wherein said cells are antigen presenting cells.

38. A method of inhibiting a T cell response comprising contacting antigen presenting cells with an oligonucleotide of claim 1 under conditions where said oligonucleotide inhibits expression of said human B7-1 protein.

39. A method of inhibiting a T cell response comprising contacting antigen presenting cells with an oligonucleotide of claim 20 under conditions where said oligonucleotide inhibits expression of said human B7-2 protein.

40. A method of inhibiting allograft rejection in an animal comprising administering to said animal an oligonucleotide of claim 20 under conditions where said oligonucleotide inhibits expression of said human B7-2 protein.

41. A method of inhibiting allograft rejection in an animal comprising:
   (a) administering to an animal an anti-inflammatory or immunosuppressive agent selected from the group consisting of a soluble ICAM protein, an antibody-toxin conjugate, prednisone, methylprednisolone, azathioprine, cyclophosphamide, cyclosporine, an interferon, a sympathomimetic, a histamine $H_1$ receptor antagonist, and a histamine $H_2$ receptor antagonist; and
   (b) administering to the animal an oligonucleotide of claim 1 under conditions where said oligonucleotide inhibits expression of said human B7-1 protein.

42. A method of inhibiting allograft rejection in an animal comprising:
   (a) administering to an animal an anti-inflammatory or immunosuppressive agent selected from the group consisting of a soluble ICAM protein, an antibody-toxin conjugate, prednisone, methylprednisolone, azathioprine, cyclophosphamide, cyciosporine, an interferon, a sympathomimetic, a histamine $H_1$ receptor antagonist, and a histamine $H_2$ receptor antagonist; and
   (b) administering to the animal an oligonucleotide of claim 20 under conditions where said oligonucleotide inhibits expression of said human B7-2 protein.

43. A method of inhibiting allograft rejection in an animal comprising:
   (a) administering to an animal an oligonucleotide comprising 8 to 30 nucleotides connected by covalent linkages, wherein at least one of said covalent linkages is a linkage other than a phosphodiester linkage, wherein said oligonucleotide has a sequence hybridizable with a nucleic acid encoding an ICAM protein and said oligonucleotide modulates the expression of said ICAM protein; and
   (b) administering to the animal an oligonucleotide of claim 1 under conditions where said oligonucleotide inhibits expression of said human B7-1 protein.

44. A method of inhibiting allograft rejection in an animal comprising:
   (a) administering to an animal an oligonucleotide comprising 8 to 30 nucleotides connected by covalent linkages, wherein at least one of said covalent linkages is a linkage other than a phosphodiester linkage, wherein said oligonucleotide has a sequence hybridizable with a nucloic acid encoding an ICAM protein and said oligonucleotide modulates the expression of said ICAM protein; and
   (b) administering to the animal an oligonucleotide of claim 1 under conditions where said oligonuclootide inhibits expression of said human B7-2 protein.

45. A method of inhibiting allograft rejection in an animal comprising:
   (a) administering to an animal an oligonucleotide of claim 1 under conditions where said oligonucleotide inhibits expression of said human B7-1 protein; and
   (b) administering to the animal an oligonucleotide comprising a nucleotide sequence set forth in SEQ ID NO: 3, 9, 10, 12, 16, 84 or 90, under conditions where said oligonucleotide modulates the expression of said B7-2 protein.

46. The method of claim 45 further comprising administering to the animal an anti-inflammatory or immunosuppressive agent selected from the group consisting of a soluble ICAM protein, an antibody-toxin conjugate, prednisone, methylprednisolone, azathioprine, cyclophosphamide, cyclosporine, an interferon, a sympathomimetic, a histamine $H_1$ receptor antagonist, a histamine $H_2$ receptor antagonist and an oligonucleotide which modulates the expression of an ICAM protein.

* * * * *

UNITED STATES PATENT AND TRADEMARK OFFICE
CERTIFICATE OF CORRECTION

PATENT NO.   : 6,077,833
DATED        : June 20, 2000
INVENTOR(S)  : Bennett et al.

Page 1 of 2

It is certified that error appears in the above-identified patent and that said Letters Patent is hereby corrected as shown below:

Column 8,
Line 12, please delete "1302" and insert therefor -- 1303 --

Column 16,
Line 50, please delete "acetyl2'" and insert therefor -- acetyl-2' --

Column 21,
Table 1, line 12355, please delete "$T^S T$ C" and insert therefore $T^S T$ C --

Columns 27 and 28,
Table 4, please insert the missing portion of the Table provided below:

| 11865 | (scrambled # 11702) | $C^S T^S A^S G^S G^S T^S C^S T^S C^S G^S T^S C^S G^S T^S C^S G^S T^S G^S G$ | 116 |
|---|---|---|---|
| 11703 | 1003-1022; tTR | $T^S C^S T^S C^S A^S C^S T^S G^S C^S C^S T^S T^S C^S A^S C^S T^S C^S T^S G^S C$ | 117 |
| 13100 | Exon 1 (Borriello et al., J. Immun., 1995, 155, 5490; 5' UTR of alternative mRNA) | $G^S T^S A^S C^S C^S A^S G^S A^S T^S G^S A^S A^S G^S G^S T^S T^S A^S T^S C^S A^S A$ (2' MO) | 118 |
| 13101 | Exon 4 (Borriello et al.; 5' UTR of alternative mRNA) | $C^S T^S T^S T^S G^S G^S A^S G^S A^S T^S T^S A^S T^S T^S C^S G^S A^S G^S T^S T$ (2' MO) | 119 |
| 13102 | Exon 5 (Borriello et al.; 5' UTR of alternative mRNA) | $G^S C^S A^S A^S G^S T^S G^S T^S A^S A^S A^S G^S C^S C^S C^S T^S G^S A^S G^S T$ (2' MO) | 120 |

Column 37,
Line 8, please delete "BALE/c" and insert therefor -- BALB/c --

Column 85,
Line 66, please delete "oligonuclootide" and insert therefor -- oligonucleotide --

UNITED STATES PATENT AND TRADEMARK OFFICE
CERTIFICATE OF CORRECTION

PATENT NO.    : 6,077,833
DATED         : June 20, 2000
INVENTOR(S)   : Bennett et al.

It is certified that error appears in the above-identified patent and that said Letters Patent is hereby corrected as shown below:

Column 88,
Line 40, please delete "terminal." and insert therefor -- terminal nucleotide. --

Column 89,
Line 25, please delete "methylprednisone" and insert therefor -- methylprednisolone --

Column 90,
Line 45, please delete "1" and insert therefor -- 20 --

Signed and Sealed this

Tenth Day of September, 2002

Attest:

Attesting Officer

JAMES E. ROGAN
*Director of the United States Patent and Trademark Office*

SEQUENCE LISTING (1) GENERAL INFORMATION:

(iii) NUMBER OF SEQUENCES: 125

(2) INFORMATION FOR SEQ ID NO:1:

(i) SEQUENCE CHARACTERISTICS:
      (A) LENGTH: 32
      (B) TYPE: Nucleic Acid
      (C) STRANDEDNESS: Single
      (D) TOPOLOGY: Linear (iv) ANTI-SENSE: No (xi) SEQUENCE DESCRIPTION: SEQ ID NO: 1:

```
GATCAGGGTA CCAGGAGCCT TAGGAGGTAC GG                              32

(2) INFORMATION FOR SEQ ID NO: 2:

(i) SEQUENCE CHARACTERISTICS:
        (A) LENGTH: 33
        (B) TYPE: Nucleic Acid
        (C) STRANDEDNESS: Single
        (D) TOPOLOGY: Linear (iv) ANTI-SENSE: Yes (xi) SEQUENCE DESCRIPTION:  SEQ ID NO: 2:

GATAGCCTCG AGTTATTTCC AGGTCATGAG CCA                             33

(2) INFORMATION FOR SEQ ID NO: 3:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION:  SEQ ID NO: 3:

TTCCAGGTCA TGAGCCATTA                                            20

(2) INFORMATION FOR SEQ ID NO: 4:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION:  SEQ ID NO: 4:

CATAAGGTGT GCTCTGAAGT                                            20

(2) INFORMATION FOR SEQ ID NO: 5:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION:  SEQ ID NO: 5:

TTACTCATGG TAATGTCTTT                                            20

(2) INFORMATION FOR SEQ ID NO: 6:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION:  SEQ ID NO: 6:

ATTAAAAACA TGTATCACTT                                            20

(2) INFORMATION FOR SEQ ID NO: 7:
```

(i) SEQUENCE CHARACTERISTICS:
              (A) LENGTH: 20
              (B) TYPE: Nucleic Acid
              (C) STRANDEDNESS: Single
              (D) TOPOLOGY: Linear (iv) ANTI-SENSE: Yes (xi) SEQUENCE DESCRIPTION: SEQ ID NO: 7:

GGAACACAGA AGCAAGGTGG                                                    20

(2) INFORMATION FOR SEQ ID NO: 8:

(i) SEQUENCE CHARACTERISTICS:
              (A) LENGTH: 20
              (B) TYPE: Nucleic Acid
              (C) STRANDEDNESS: Single
              (D) TOPOLOGY: Linear (iv) ANTI-SENSE: Yes (xi) SEQUENCE DESCRIPTION: SEQ ID NO: 8:

CCGTACCTCC TAAGGCTCCT                                                    20

(2) INFORMATION FOR SEQ ID NO: 9:

(i) SEQUENCE CHARACTERISTICS:
              (A) LENGTH: 20
              (B) TYPE: Nucleic Acid
              (C) STRANDEDNESS: Single
              (D) TOPOLOGY: Linear (iv) ANTI-SENSE: Yes (xi) SEQUENCE DESCRIPTION: SEQ ID NO: 9:

CCCATAGTGC GTTCACAAAT                                                    20

(2) INFORMATION FOR SEQ ID NO: 10:

(i) SEQUENCE CHARACTERISTICS:
              (A) LENGTH: 20
              (B) TYPE: Nucleic Acid
              (C) STRANDEDNESS: Single
              (D) TOPOLOGY: Linear (iv) ANTI-SENSE: Yes (xi) SEQUENCE DESCRIPTION: SEQ ID NO: 10:

GCACAGCAGC ATTCCCAAGG                                                    20

(2) INFORMATION FOR SEQ ID NO: 11:

(i) SEQUENCE CHARACTERISTICS:
              (A) LENGTH: 20
              (B) TYPE: Nucleic Acid
              (C) STRANDEDNESS: Single
              (D) TOPOLOGY: Linear (iv) ANTI-SENSE: Yes (xi) SEQUENCE DESCRIPTION: SEQ ID NO: 11:

TTGCAAATTG GCATGGCAGG                                                    20

(2) INFORMATION FOR SEQ ID NO: 12:

(i) SEQUENCE CHARACTERISTICS:
              (A) LENGTH: 20
              (B) TYPE: Nucleic Acid
              (C) STRANDEDNESS: Single
              (D) TOPOLOGY: Linear (iv) ANTI-SENSE: Yes (xi) SEQUENCE DESCRIPTION: SEQ ID NO: 12:

TGGTATGGGC TTTACTCTTT					20

(2) INFORMATION FOR SEQ ID NO: 13:

(i) SEQUENCE CHARACTERISTICS:
            (A) LENGTH: 20
            (B) TYPE: Nucleic Acid
            (C) STRANDEDNESS: Single
            (D) TOPOLOGY: Linear (iv) ANTI-SENSE: Yes (xi) SEQUENCE DESCRIPTION: SEQ ID NO: 13:

AAAAGGTTGC CCAGGAACGG					20

(2) INFORMATION FOR SEQ ID NO: 14:

(i) SEQUENCE CHARACTERISTICS:
            (A) LENGTH: 20
            (B) TYPE: Nucleic Acid
            (C) STRANDEDNESS: Single
            (D) TOPOLOGY: Linear (iv) ANTI-SENSE: Yes (xi) SEQUENCE DESCRIPTION: SEQ ID NO: 14:

GGGAGTCCTG GAGCCCCCTT					20

(2) INFORMATION FOR SEQ ID NO: 15:

(i) SEQUENCE CHARACTERISTICS:
            (A) LENGTH: 20
            (B) TYPE: Nucleic Acid
            (C) STRANDEDNESS: Single
            (D) TOPOLOGY: Linear (iv) ANTI-SENSE: Yes (xi) SEQUENCE DESCRIPTION: SEQ ID NO: 15:

CCATTAAGCT GGGCTTGGCC					20

(2) INFORMATION FOR SEQ ID NO: 16:

(i) SEQUENCE CHARACTERISTICS:
            (A) LENGTH: 20
            (B) TYPE: Nucleic Acid
            (C) STRANDEDNESS: Single
            (D) TOPOLOGY: Linear (iv) ANTI-SENSE: Yes (xi) SEQUENCE DESCRIPTION: SEQ ID NO: 16:

TGCGAGCTCC CCGTACCTCC					20

(2) INFORMATION FOR SEQ ID NO: 17:

(i) SEQUENCE CHARACTERISTICS:
            (A) LENGTH: 20
            (B) TYPE: Nucleic Acid
            (C) STRANDEDNESS: Single
            (D) TOPOLOGY: Linear (x) PUBLICATION INFORMATION:
            (H) DOCUMENT NUMBER: US 5514788
            (I) FILING DATE: 17-MAY-1993
            (J) PUBLICATION DATE: 07-MAY-1996

(iv) ANTI-SENSE: Yes (xi) SEQUENCE DESCRIPTION: SEQ ID NO: 17:

GCCCAAGCTG GCATCCGTCA                                                    20

(2) INFORMATION FOR SEQ ID NO: 18:

(i) SEQUENCE CHARACTERISTICS:
                (A) LENGTH: 20
                (B) TYPE: Nucleic Acid
                (C) STRANDEDNESS: Single
                (D) TOPOLOGY: Linear (iv) ANTI-SENSE: Yes (xi) SEQUENCE DESCRIPTION: SEQ ID NO: 18:

GGATTGCCAA GCCCATGGTG                                                    20

(2) INFORMATION FOR SEQ ID NO: 19:

(i) SEQUENCE CHARACTERISTICS:
                (A) LENGTH: 20
                (B) TYPE: Nucleic Acid
                (C) STRANDEDNESS: Single
                (D) TOPOLOGY: Linear (iv) ANTI-SENSE: Yes (xi) SEQUENCE DESCRIPTION: SEQ ID NO: 19:

CTAAGTAGTG CTAGCCGGGA                                                    20

(2) INFORMATION FOR SEQ ID NO: 20:

(i) SEQUENCE CHARACTERISTICS:
                (A) LENGTH: 38
                (B) TYPE: Nucleic Acid
                (C) STRANDEDNESS: Single
                (D) TOPOLOGY: Linear (iv) ANTI-SENSE: No (xi) SEQUENCE DESCRIPTION: SEQ ID NO: 20:

GATCAGGGTA CCCCAAAGAA AAAGTGATTT GTCATTGC                                 38

(2) INFORMATION FOR SEQ ID NO: 21:

(i) SEQUENCE CHARACTERISTICS:
                (A) LENGTH: 35
                (B) TYPE: Nucleic Acid
                (C) STRANDEDNESS: Single
                (D) TOPOLOGY: Linear (iv) ANTI-SENSE: Yes (xi) SEQUENCE DESCRIPTION: SEQ ID NO: 21:

GATAGCCTCG AGGATAATGA ATTGGCTGAC AAGAC                                    35

(2) INFORMATION FOR SEQ ID NO: 22:

(i) SEQUENCE CHARACTERISTICS:
                (A) LENGTH: 20
                (B) TYPE: Nucleic Acid
                (C) STRANDEDNESS: Single
                (D) TOPOLOGY: Linear (iv) ANTI-SENSE: Yes (xi) SEQUENCE DESCRIPTION: SEQ ID NO: 22:

GGGTAAGACT CCACTTCTGA                                          20

(2) INFORMATION FOR SEQ ID NO: 23:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 23:

GGGTCTCCAA AGGTTGTGGA                                          20

(2) INFORMATION FOR SEQ ID NO: 24:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 24:

GTTCCTGGGT CTCCAAAGGT                                          20

(2) INFORMATION FOR SEQ ID NO: 25:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 25:

ACACACAGAG ATTGGAGGGT                                          20

(2) INFORMATION FOR SEQ ID NO: 26:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 26:

GCTCACGTAG AAGACCCTCC                                          20

(2) INFORMATION FOR SEQ ID NO: 27:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 27:

GGCAGGGCTG ATGACAATCC                                          20

(2) INFORMATION FOR SEQ ID NO: 28:

(i) SEQUENCE CHARACTERISTICS:
            (A) LENGTH: 20
            (B) TYPE: Nucleic Acid
            (C) STRANDEDNESS: Single
            (D) TOPOLOGY: Linear (iv) ANTI-SENSE: Yes (xi) SEQUENCE DESCRIPTION: SEQ ID NO: 28:

TGCAAAACAG GCAGGGCTGA                                           20

(2) INFORMATION FOR SEQ ID NO: 29:

(i) SEQUENCE CHARACTERISTICS:
            (A) LENGTH: 20
            (B) TYPE: Nucleic Acid
            (C) STRANDEDNESS: Single
            (D) TOPOLOGY: Linear (iv) ANTI-SENSE: Yes (xi) SEQUENCE DESCRIPTION: SEQ ID NO: 29:

AGACCAGGGC ACTTCCCAGG                                           20

(2) INFORMATION FOR SEQ ID NO: 30:

(i) SEQUENCE CHARACTERISTICS:
            (A) LENGTH: 20
            (B) TYPE: Nucleic Acid
            (C) STRANDEDNESS: Single
            (D) TOPOLOGY: Linear (iv) ANTI-SENSE: Yes (xi) SEQUENCE DESCRIPTION: SEQ ID NO: 30:

CCTGCCTCCG TGTGTGGCCC                                           20

(2) INFORMATION FOR SEQ ID NO: 31:

(i) SEQUENCE CHARACTERISTICS:
            (A) LENGTH: 20
            (B) TYPE: Nucleic Acid
            (C) STRANDEDNESS: Single
            (D) TOPOLOGY: Linear (iv) ANTI-SENSE: Yes (xi) SEQUENCE DESCRIPTION: SEQ ID NO: 31:

GACCAGCCAG CACCAAGAGC                                           20

(2) INFORMATION FOR SEQ ID NO: 32:

(i) SEQUENCE CHARACTERISTICS:
            (A) LENGTH: 20
            (B) TYPE: Nucleic Acid
            (C) STRANDEDNESS: Single
            (D) TOPOLOGY: Linear (iv) ANTI-SENSE: Yes (xi) SEQUENCE DESCRIPTION: SEQ ID NO: 32:

CCACAGGACA GCGTTGCCAC                                           20

(2) INFORMATION FOR SEQ ID NO: 33:

(i) SEQUENCE CHARACTERISTICS:
            (A) LENGTH: 20
            (B) TYPE: Nucleic Acid
            (C) STRANDEDNESS: Single
            (D) TOPOLOGY: Linear (iv) ANTI-SENSE: Yes (xi) SEQUENCE DESCRIPTION: SEQ ID NO: 33:

CCGGTTCTTG TACTCGGGCC    20

(2) INFORMATION FOR SEQ ID NO: 34:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 34:

CCAACCAGGA GAGGTGAGGC    20

(2) INFORMATION FOR SEQ ID NO: 35:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 35:

GGCAAAGCAG TAGGTCAGGC    20

(2) INFORMATION FOR SEQ ID NO: 36:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 36:

GCCTCATGAT CCCCACGATC    20

(2) INFORMATION FOR SEQ ID NO: 37:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 37:

AGTCCTACTA CCAGCCGCCT    20

(2) INFORMATION FOR SEQ ID NO: 38:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 38:

TCAGGGTAAG ACTCCACTTC                                                    20

(2) INFORMATION FOR SEQ ID NO: 39:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 39:

AGGGTGTTCC TGGGTCTCCA                                                    20

(2) INFORMATION FOR SEQ ID NO: 40:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 40:

CTCCGTGTGT GGCCCATGGC                                                    20

(2) INFORMATION FOR SEQ ID NO: 41:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 41:

GGATGGTGAT GTTCCCTGCC                                                    20

(2) INFORMATION FOR SEQ ID NO: 42:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 42:

TGAGAAAGAC CAGCCAGCAC                                                    20

(2) INFORMATION FOR SEQ ID NO: 43:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 43:

GGGCGCAGAG CCAGGATCAC                                                    20

(2) INFORMATION FOR SEQ ID NO: 44:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 44:

GGCCCAGGAT GGGAGCAGGT                                       20

(2) INFORMATION FOR SEQ ID NO: 45:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 45:

AGGGCGTACA CTTTCCCTTC                                       20

(2) INFORMATION FOR SEQ ID NO: 46:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 46:

CAGCCCCTTG CTTCTGCGGA                                       20

(2) INFORMATION FOR SEQ ID NO: 47:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 47:

AAGGAGAGGG ATGCCAGCCA                                       20

(2) INFORMATION FOR SEQ ID NO: 48:

(i) SEQUENCE CHARACTERISTICS:
        (A) LENGTH: 22
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 48:

CTGTTACTTT ACAGAGGGTT TG                                    22

(2) INFORMATION FOR SEQ ID NO: 49:

(i) SEQUENCE CHARACTERISTICS:
        (A) LENGTH: 25
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 49:

CTTCTGTTAC TTTACAGAGG GTTTG          25

(2) INFORMATION FOR SEQ ID NO: 50:

(i) SEQUENCE CHARACTERISTICS:
        (A) LENGTH: 21
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 50:

CTGTTACTTT ACAGAGGGTT T          21

(2) INFORMATION FOR SEQ ID NO: 51:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 51:

GCCCTCGTCA GATGGGCGCA          20

(2) INFORMATION FOR SEQ ID NO: 52:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 52:

AGTCCTACTA CCAGCCGCCT          20

(2) INFORMATION FOR SEQ ID NO: 53:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 53:

AGTAAGAGTC TATTGAGGTA          20

(2) INFORMATION FOR SEQ ID NO: 54:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 54:

```
GGTTGAGTTT CACAACCTGA                                           20

(2) INFORMATION FOR SEQ ID NO: 55:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION:  SEQ ID NO: 55:

GTCCACAGAA TGGAACAGAG                                           20

(2) INFORMATION FOR SEQ ID NO: 56:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION:  SEQ ID NO: 56:

GGCATCCACC CGGCAGATGC                                           20

(2) INFORMATION FOR SEQ ID NO: 57:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION:  SEQ ID NO: 57:

TGGATGGCAT CCACCCGGCA                                           20

(2) INFORMATION FOR SEQ ID NO: 58:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION:  SEQ ID NO: 58:

AGGCACCTCC TAGGCTCACA                                           20

(2) INFORMATION FOR SEQ ID NO: 59:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION:  SEQ ID NO: 59:

GCCAATGGAG CTTAGGCACC                                           20

(2) INFORMATION FOR SEQ ID NO: 60:
```

(i) SEQUENCE CHARACTERISTICS:
            (A) LENGTH: 20
            (B) TYPE: Nucleic Acid
            (C) STRANDEDNESS: Single
            (D) TOPOLOGY: Linear (iv) ANTI-SENSE: Yes (xi) SEQUENCE DESCRIPTION: SEQ ID NO: 60:

CATGATGGGG AAAGCCAGGA                                                      20

(2) INFORMATION FOR SEQ ID NO: 61:

(i) SEQUENCE CHARACTERISTICS:
            (A) LENGTH: 20
            (B) TYPE: Nucleic Acid
            (C) STRANDEDNESS: Single
            (D) TOPOLOGY: Linear (iv) ANTI-SENSE: Yes (xi) SEQUENCE DESCRIPTION: SEQ ID NO: 61:

AATTGCAAGC CATAGCTTCA                                                      20

(2) INFORMATION FOR SEQ ID NO: 62:

(i) SEQUENCE CHARACTERISTICS:
            (A) LENGTH: 20
            (B) TYPE: Nucleic Acid
            (C) STRANDEDNESS: Single
            (D) TOPOLOGY: Linear (iv) ANTI-SENSE: Yes (xi) SEQUENCE DESCRIPTION: SEQ ID NO: 62:

CGGCAAGGCA GCAATACCTT                                                      20

(2) INFORMATION FOR SEQ ID NO: 63:

(i) SEQUENCE CHARACTERISTICS:
            (A) LENGTH: 20
            (B) TYPE: Nucleic Acid
            (C) STRANDEDNESS: Single
            (D) TOPOLOGY: Linear (iv) ANTI-SENSE: Yes (xi) SEQUENCE DESCRIPTION: SEQ ID NO: 63:

CCCAGCAATG ACAGACAGCA                                                      20

(2) INFORMATION FOR SEQ ID NO: 64:

(i) SEQUENCE CHARACTERISTICS:
            (A) LENGTH: 20
            (B) TYPE: Nucleic Acid
            (C) STRANDEDNESS: Single
            (D) TOPOLOGY: Linear (iv) ANTI-SENSE: Yes (xi) SEQUENCE DESCRIPTION: SEQ ID NO: 64:

GGTCTGAAAG GACCAGGCCC                                                      20

(2) INFORMATION FOR SEQ ID NO: 65:

(i) SEQUENCE CHARACTERISTICS:
            (A) LENGTH: 20
            (B) TYPE: Nucleic Acid
            (C) STRANDEDNESS: Single
            (D) TOPOLOGY: Linear (iv) ANTI-SENSE: Yes (xi) SEQUENCE DESCRIPTION: SEQ ID NO: 65:

TGGGAAACCC CCGGAAGCAA                          20

(2) INFORMATION FOR SEQ ID NO: 66:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 66:

GGCTTTGGGA AACCCCCGGA                          20

(2) INFORMATION FOR SEQ ID NO: 67:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 67:

TCAGATTCAG GATCCTGGGA                          20

(2) INFORMATION FOR SEQ ID NO: 68:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 68:

CCCAGGTGAA GTCCTCTGAC                          20

(2) INFORMATION FOR SEQ ID NO: 69:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 69:

CTGCGCCGAA TCCTGCCCCA                          20

(2) INFORMATION FOR SEQ ID NO: 70:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 70:

| CAGGCCCGAA GGTAAGGCTG | 20 |

(2) INFORMATION FOR SEQ ID NO: 71:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 71:

| TCAGCTAGCA CGGTGCTGAA | 20 |

(2) INFORMATION FOR SEQ ID NO: 72:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 72:

| GGCCCAGCAA ACTTGCCCGT | 20 |

(2) INFORMATION FOR SEQ ID NO: 73:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 73:

| CCACCACAGT GGGCTCAGCC | 20 |

(2) INFORMATION FOR SEQ ID NO: 74:

(i) SEQUENCE CHARACTERISTICS:
        (A) LENGTH: 19
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 74:

| GGCCATGAGG GCAATCTAA | 19 |

(2) INFORMATION FOR SEQ ID NO: 75:

(i) SEQUENCE CHARACTERISTICS:
        (A) LENGTH: 21
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 75:

| GTGGCCATGA GGGCAATCTA A | 21 |

(2) INFORMATION FOR SEQ ID NO: 76:

(i) SEQUENCE CHARACTERISTICS:
            (A) LENGTH: 20
            (B) TYPE: Nucleic Acid
            (C) STRANDEDNESS: Single
            (D) TOPOLOGY: Linear (iv) ANTI-SENSE: Yes (xi) SEQUENCE DESCRIPTION: SEQ ID NO: 76:

GATTTAACAT TTGGCGCCCA                                               20

(2) INFORMATION FOR SEQ ID NO: 77:

(i) SEQUENCE CHARACTERISTICS:
            (A) LENGTH: 20
            (B) TYPE: Nucleic Acid
            (C) STRANDEDNESS: Single
            (D) TOPOLOGY: Linear (iv) ANTI-SENSE: Yes (xi) SEQUENCE DESCRIPTION: SEQ ID NO: 77:

AAAGTTACAA CATTATATCT                                               20

(2) INFORMATION FOR SEQ ID NO: 78:

(i) SEQUENCE CHARACTERISTICS:
            (A) LENGTH: 20
            (B) TYPE: Nucleic Acid
            (C) STRANDEDNESS: Single
            (D) TOPOLOGY: Linear (iv) ANTI-SENSE: Yes (xi) SEQUENCE DESCRIPTION: SEQ ID NO: 78:

AGTGCGATTC TCAAACCTAC                                               20

(2) INFORMATION FOR SEQ ID NO: 79:

(i) SEQUENCE CHARACTERISTICS:
            (A) LENGTH: 16
            (B) TYPE: Nucleic Acid
            (C) STRANDEDNESS: Single
            (D) TOPOLOGY: Linear (iv) ANTI-SENSE: Yes (xi) SEQUENCE DESCRIPTION: SEQ ID NO: 79:

TATTTGCGAG CTCCCC                                                   16

(2) INFORMATION FOR SEQ ID NO: 80:

(i) SEQUENCE CHARACTERISTICS:
            (A) LENGTH: 15
            (B) TYPE: Nucleic Acid
            (C) STRANDEDNESS: Single
            (D) TOPOLOGY: Linear (iv) ANTI-SENSE: Yes (xi) SEQUENCE DESCRIPTION: SEQ ID NO: 80:

TATTTGCGAG CTCCC                                                    15

(2) INFORMATION FOR SEQ ID NO: 81:

(i) SEQUENCE CHARACTERISTICS:
            (A) LENGTH: 14
            (B) TYPE: Nucleic Acid
            (C) STRANDEDNESS: Single
            (D) TOPOLOGY: Linear (iv) ANTI-SENSE: Yes (xi) SEQUENCE DESCRIPTION: SEQ ID NO: 81:

TATTTGCGAG CTCC                                                                14

(2) INFORMATION FOR SEQ ID NO: 82:

(i) SEQUENCE CHARACTERISTICS:
       (A) LENGTH: 20
       (B) TYPE: Nucleic Acid
       (C) STRANDEDNESS: Single
       (D) TOPOLOGY: Linear (iv) ANTI-SENSE: Yes (xi) SEQUENCE DESCRIPTION: SEQ ID NO: 82:

CGACAGCTCC TGCGCTCCTC                                                          20

(2) INFORMATION FOR SEQ ID NO: 83:

(i) SEQUENCE CHARACTERISTICS:
       (A) LENGTH: 16
       (B) TYPE: Nucleic Acid
       (C) STRANDEDNESS: Single
       (D) TOPOLOGY: Linear (iv) ANTI-SENSE: Yes (xi) SEQUENCE DESCRIPTION: SEQ ID NO: 83:

AGCTCCCCGT ACCTCC                                                              16

(2) INFORMATION FOR SEQ ID NO: 84:

(i) SEQUENCE CHARACTERISTICS:
       (A) LENGTH: 16
       (B) TYPE: Nucleic Acid
       (C) STRANDEDNESS: Single
       (D) TOPOLOGY: Linear (iv) ANTI-SENSE: Yes (xi) SEQUENCE DESCRIPTION: SEQ ID NO: 84:

TGCGAGCTCC CCGTAC                                                              16

(2) INFORMATION FOR SEQ ID NO: 85:

(i) SEQUENCE CHARACTERISTICS:
       (A) LENGTH: 10
       (B) TYPE: Nucleic Acid
       (C) STRANDEDNESS: Single
       (D) TOPOLOGY: Linear (iv) ANTI-SENSE: Yes (xi) SEQUENCE DESCRIPTION: SEQ ID NO: 85:

CTCCCCGTAC                                                                     10

(2) INFORMATION FOR SEQ ID NO: 86:

(i) SEQUENCE CHARACTERISTICS:
       (A) LENGTH: 11
       (B) TYPE: Nucleic Acid
       (C) STRANDEDNESS: Single
       (D) TOPOLOGY: Linear (iv) ANTI-SENSE: Yes (xi) SEQUENCE DESCRIPTION: SEQ ID NO: 86:

GCTCCCCGTA C                                                                  11

(2) INFORMATION FOR SEQ ID NO: 87:

(i) SEQUENCE CHARACTERISTICS:
        (A) LENGTH: 12
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 87:

AGCTCCCCGT AC                                                                 12

(2) INFORMATION FOR SEQ ID NO: 88:

(i) SEQUENCE CHARACTERISTICS:
        (A) LENGTH: 13
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 88:

GAGCTCCCCG TAC                                                                13

(2) INFORMATION FOR SEQ ID NO: 89:

(i) SEQUENCE CHARACTERISTICS:
        (A) LENGTH: 14
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 89:

CGAGCTCCCC GTAC                                                               14

(2) INFORMATION FOR SEQ ID NO: 90:

(i) SEQUENCE CHARACTERISTICS:
        (A) LENGTH: 15
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 90:

GCGAGCTCCC CGTAC                                                              15

(2) INFORMATION FOR SEQ ID NO: 91:

(i) SEQUENCE CHARACTERISTICS:
        (A) LENGTH: 13
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 91:

GCGAGCTCCC CGT                                                                13

(2) INFORMATION FOR SEQ ID NO: 92:

(i) SEQUENCE CHARACTERISTICS:
            (A) LENGTH: 15
            (B) TYPE: Nucleic Acid
            (C) STRANDEDNESS: Single
            (D) TOPOLOGY: Linear (iv) ANTI-SENSE: Yes (xi) SEQUENCE DESCRIPTION: SEQ ID NO: 92:

GCCGCCGCCA AGTCT                                                              15

(2) INFORMATION FOR SEQ ID NO: 93:

(i) SEQUENCE CHARACTERISTICS:
            (A) LENGTH: 24
            (B) TYPE: Nucleic Acid
            (C) STRANDEDNESS: Single
            (D) TOPOLOGY: Linear (iv) ANTI-SENSE: Yes (xi) SEQUENCE DESCRIPTION: SEQ ID NO: 93:

GAGAAGCAAA GCTTTCACCC TGTG                                                    24

(2) INFORMATION FOR SEQ ID NO: 94:

(i) SEQUENCE CHARACTERISTICS:
            (A) LENGTH: 22
            (B) TYPE: Nucleic Acid
            (C) STRANDEDNESS: Single
            (D) TOPOLOGY: Linear (iv) ANTI-SENSE: Yes (xi) SEQUENCE DESCRIPTION: SEQ ID NO: 94:

GAAGCAAAGC TTTCACCCTG TG                                                      22

(2) INFORMATION FOR SEQ ID NO: 95:

(i) SEQUENCE CHARACTERISTICS:
            (A) LENGTH: 19
            (B) TYPE: Nucleic Acid
            (C) STRANDEDNESS: Single
            (D) TOPOLOGY: Linear (iv) ANTI-SENSE: Yes (xi) SEQUENCE DESCRIPTION: SEQ ID NO: 95:

GCAAAGCTTT CACCCTGTG                                                          19

(2) INFORMATION FOR SEQ ID NO: 96:

(i) SEQUENCE CHARACTERISTICS:
            (A) LENGTH: 24
            (B) TYPE: Nucleic Acid
            (C) STRANDEDNESS: Single
            (D) TOPOLOGY: Linear (iv) ANTI-SENSE: Yes (xi) SEQUENCE DESCRIPTION: SEQ ID NO: 96:

CTCCCCGTAC CTCCTAAGGC TCCT                                                    24

(2) INFORMATION FOR SEQ ID NO: 97:

(i) SEQUENCE CHARACTERISTICS:
            (A) LENGTH: 22
            (B) TYPE: Nucleic Acid
            (C) STRANDEDNESS: Single
            (D) TOPOLOGY: Linear (iv) ANTI-SENSE: Yes (xi) SEQUENCE DESCRIPTION: SEQ ID NO: 97:

CCCCGTACCT CCTAAGGCTC CT                                                  22

(2) INFORMATION FOR SEQ ID NO: 98:

(i) SEQUENCE CHARACTERISTICS:
        (A) LENGTH: 19
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 98:

CGTACCTCCT AAGGCTCCT                                                      19

(2) INFORMATION FOR SEQ ID NO: 99:

(i) SEQUENCE CHARACTERISTICS:
        (A) LENGTH: 32
        (B) TYPE: Nucleic Acid
        (C) STRANDEDNESS: Single
        (D) TOPOLOGY: Linear (iv) ANTI-SENSE: No (xi) SEQUENCE DESCRIPTION: SEQ ID NO: 99:

GATCAGGGTA CCAAGAGTGG CTCCTGTAGG CA                                       32

(2) INFORMATION FOR SEQ ID NO: 100:

(i) SEQUENCE CHARACTERISTICS:
        (A) LENGTH: 32
        (B) TYPE: Nucleic Acid
        (C) STRANDEDNESS: Single
        (D) TOPOLOGY: Linear (iv) ANTI-SENSE: No (xi) SEQUENCE DESCRIPTION: SEQ ID NO: 100:

GATAGCCTCG AGGTAGAATT CCAATCAGCT GA                                       32

(2) INFORMATION FOR SEQ ID NO: 101:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (x) PUBLICATION INFORMATION:
        (A) AUTHORS: Stepkowski, Stanislaw M.
            Tu, Zizheng
            Condon, Thomas P.
            Bennett, C. Frank
        (B) TITLE: Blocking of Heart Allograft Rejection by
            Intercellular Adhesion Molecule-1 Antisense
            Oligonucleotide Alone or in Combination with Other
            Immunosuppressive Modalities
        (C) JOURNAL: The Journal of Immunology
        (D) VOLUME: 153
        (F) PAGES: 5336-5346
        (G) DATE: 01-DEC-1994

(xi) SEQUENCE DESCRIPTION: SEQ ID NO: 101:

TGCATCCCCC AGGCCACCAT                                                     20

(2) INFORMATION FOR SEQ ID NO: 102:

(i) SEQUENCE CHARACTERISTICS:
        (A) LENGTH: 21
        (B) TYPE: Nucleic Acid
        (C) STRANDEDNESS: Single
        (D) TOPOLOGY: Linear (iv) ANTI-SENSE: Yes (iv) ANTI-SENSE: Yes (x) PUBLICATION INFORMATION:
        (A) AUTHORS: Stepkowski, Stanislaw M.
            Tu, Zizheng
            Condon, Thomas P.
            Bennett, C. Frank
        (B) TITLE: Blocking of Heart Allograft Rejection by
            Intercellular Adhesion Molecule-1 Antisense
            Oligonucleotide Alone or in Combination with Other
            Immunosuppressive Modalities
        (C) JOURNAL: The Journal of Immunology
        (D) VOLUME: 153
        (F) PAGES: 5336-5346
        (G) DATE: 01-DEC-1994

(xi) SEQUENCE DESCRIPTION: SEQ ID NO: 102:

GCCGAGGTCC ATGTCGTACG C                                          21

(2) INFORMATION FOR SEQ ID NO: 103:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 103:

ACACGTCTACA GGAGTCTGG                                           20

(2) INFORMATION FOR SEQ ID NO: 104:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 104:

CAAGCCCATG GTGCATCTGG                                           20

(2) INFORMATION FOR SEQ ID NO: 105:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 105:

CTGGGGTCCA TCGTGGGTGC                                           20

(2) INFORMATION FOR SEQ ID NO: 106:

(i) SEQUENCE CHARACTERISTICS:
    (A) LENGTH: 20
    (B) TYPE: Nucleic Acid
    (C) STRANDEDNESS: Single
    (D) TOPOLOGY: Linear (iv) ANTI-SENSE: Yes (xi) SEQUENCE DESCRIPTION: SEQ ID NO: 106:

CCGTGCTGCC TACAGGAGCC                                         20

(2) INFORMATION FOR SEQ ID NO: 107:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 107:

GGTGCTTCCG TAAGTTCTGG                                         20

(2) INFORMATION FOR SEQ ID NO: 108:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 108:

GGATTGCCAA GCCCATGGTG                                         20

(2) INFORMATION FOR SEQ ID NO: 109:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 109:

CTAAGTAGTG CTAGCCGGGA                                         20

(2) INFORMATION FOR SEQ ID NO: 110:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 110:

TGCGTCTCCA CGGAAACAGC                                         20

(2) INFORMATION FOR SEQ ID NO: 111:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 111:

GTGCGGCCCA GGTACTTGGC          20

(2) INFORMATION FOR SEQ ID NO: 112:

(i) SEQUENCE CHARACTERISTICS:
            (A) LENGTH: 20
            (B) TYPE: Nucleic Acid
            (C) STRANDEDNESS: Single
            (D) TOPOLOGY: Linear (iv) ANTI-SENSE: Yes (xi) SEQUENCE DESCRIPTION: SEQ ID NO: 112:

ACAAGGAGGA GGGCCACAGT          20

(2) INFORMATION FOR SEQ ID NO: 113:

(i) SEQUENCE CHARACTERISTICS:
            (A) LENGTH: 20
            (B) TYPE: Nucleic Acid
            (C) STRANDEDNESS: Single
            (D) TOPOLOGY: Linear (iv) ANTI-SENSE: Yes (xi) SEQUENCE DESCRIPTION: SEQ ID NO: 113:

TGAGAGGTTT GGAGGAAATC          20

(2) INFORMATION FOR SEQ ID NO: 114:

(i) SEQUENCE CHARACTERISTICS:
            (A) LENGTH: 20
            (B) TYPE: Nucleic Acid
            (C) STRANDEDNESS: Single
            (D) TOPOLOGY: Linear (iv) ANTI-SENSE: Yes (xi) SEQUENCE DESCRIPTION: SEQ ID NO: 114:

GATAGTCTCT CTGTCAGCGT          20

(2) INFORMATION FOR SEQ ID NO: 115:

(i) SEQUENCE CHARACTERISTICS:
            (A) LENGTH: 20
            (B) TYPE: Nucleic Acid
            (C) STRANDEDNESS: Single
            (D) TOPOLOGY: Linear (iv) ANTI-SENSE: Yes (xi) SEQUENCE DESCRIPTION: SEQ ID NO: 115:

GTTGCTGGGC CTGCTAGGCT          20

(2) INFORMATION FOR SEQ ID NO: 116:

(i) SEQUENCE CHARACTERISTICS:
            (A) LENGTH: 20
            (B) TYPE: Nucleic Acid
            (C) STRANDEDNESS: Single
            (D) TOPOLOGY: Linear (iv) ANTI-SENSE: Yes (xi) SEQUENCE DESCRIPTION: SEQ ID NO: 116:

CTAGGTCTCG TCGTCGGTGG 20

(2) INFORMATION FOR SEQ ID NO: 117:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 117:

TCTCACTGCC TTCACTCTGC 20

(2) INFORMATION FOR SEQ ID NO: 118:

(i) SEQUENCE CHARACTERISTICS:
        (A) LENGTH: 21
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 118:

GTACCAGATG AAGGTTATCA A 21

(2) INFORMATION FOR SEQ ID NO: 119:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 119:

CTTTGGAGAT TATTCGAGTT 20

(2) INFORMATION FOR SEQ ID NO: 120:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 120:

GCAAGTGTAA AGCCCTGAGT 20

(2) INFORMATION FOR SEQ ID NO: 121:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 121:

AGAATTCCAA TCAGCTGAGA 20

(2) INFORMATION FOR SEQ ID NO: 122:

-continued

```
        (i) SEQUENCE CHARACTERISTICS:
            (A) LENGTH: 20
            (B) TYPE: Nucleic Acid
            (C) STRANDEDNESS: Single
            (D) TOPOLOGY: Linear (iv) ANTI-SENSE: Yes (xi) SEQUENCE DESCRIPTION: SEQ ID NO: 122:

TCTGAGAAAC TCTGCACTTC                                                        20

(2) INFORMATION FOR SEQ ID NO: 123:

(i) SEQUENCE CHARACTERISTICS:
            (A) LENGTH: 20
            (B) TYPE: Nucleic Acid
            (C) STRANDEDNESS: Single
            (D) TOPOLOGY: Linear (iv) ANTI-SENSE: Yes (xi) SEQUENCE DESCRIPTION: SEQ ID NO: 123:

TCCTCAGGCT CTCACTGCCT                                                        20

(2) INFORMATION FOR SEQ ID NO: 124:

(i) SEQUENCE CHARACTERISTICS:
            (A) LENGTH: 20
            (B) TYPE: Nucleic Acid
            (C) STRANDEDNESS: Single
            (D) TOPOLOGY: Linear (iv) ANTI-SENSE: Yes (xi) SEQUENCE DESCRIPTION: SEQ ID NO: 124:

GGTTGTTCAA GTCCGTGCTG                                                        20

(2) INFORMATION FOR SEQ ID NO: 125:

(i) SEQUENCE CHARACTERISTICS:
            (A) LENGTH: 21
            (B) TYPE: Nucleic Acid
            (C) STRANDEDNESS: Single
            (D) TOPOLOGY: Linear (iv) ANTI-SENSE: Yes (xi) SEQUENCE DESCRIPTION: SEQ ID NO: 125:

GCCGAGGTCC ATGTCGTAGC C                                                      21
```